(12) United States Patent
Enever et al.

(10) Patent No.: US 8,685,895 B2
(45) Date of Patent: *Apr. 1, 2014

(54) METHODS FOR SELECTING PROTEASE RESISTANT POLYPEPTIDES

(76) Inventors: Carolyn Enever, Cambridge (GB);
Laurent Jespers, Cambridge (GB);
Malgorzata Pupecka, Cambridge (GB);
Ian M Tomlinson, Stevenage (GB)

( * ) Notice: Subject to any disclaimer, the term of this patent is extended or adjusted under 35 U.S.C. 154(b) by 69 days.

This patent is subject to a terminal disclaimer.

(21) Appl. No.: 13/131,640

(22) PCT Filed: Dec. 4, 2009

(86) PCT No.: PCT/EP2009/066395
§ 371 (c)(1),
(2), (4) Date: May 27, 2011

(87) PCT Pub. No.: WO2010/063818
PCT Pub. Date: Jun. 10, 2010

(65) Prior Publication Data
US 2011/0229458 A1      Sep. 22, 2011

Related U.S. Application Data

(60) Provisional application No. 61/120,135, filed on Dec. 5, 2008.

(51) Int. Cl.
*C40B 40/10*      (2006.01)

(52) U.S. Cl.
USPC .......................................................... 506/18

(58) Field of Classification Search
None
See application file for complete search history.

(56) References Cited

U.S. PATENT DOCUMENTS

2007/0003549 A1 *   1/2007   Ignatovich et al. ........ 424/145.1

OTHER PUBLICATIONS

Harmsen et al. (Feb. 1, 2006) Applied Microbiology and Biotechnology vol. 73 pp. 544 to 551.*

* cited by examiner

*Primary Examiner* — Christian Boesen
(74) *Attorney, Agent, or Firm* — Jason C. Fedon; William T. Han

(57) ABSTRACT

The disclosure relates to a method for selecting, isolating and/or recovering a peptide or polypeptide from a library or a repertoire of peptides and polypeptides (e.g., a display system) that is resistant to degradation by a protease such as a protease found in the serum. Generally, the method comprises providing a library or repertoire of peptides or polypeptides, incubating the library or repertoire with a protease under conditions suitable for protease activity, and selecting, isolating and/or recovering a peptide or polypeptide that is resistant to degradation by the protease and has a desired biological activity. The selected peptides and polypeptides have utility as therapeutics, e.g., for treating disease in humans.

3 Claims, 13 Drawing Sheets

DMS7161           Control M
A     B

FIGURE 1

Sequence 1 (SEQ ID NO: 11);
DMS7190
HGEGTFTSDVSSYSEEAAAKEFIAWLVKGRGKEAAAKELAADIQMTQSPS
SLSASVGDRVTITCRASQWIGSQLSWYQQKPGKAPKLLIMWRSSLQSGVP
SRFSGSGSGTDFTLTISSLQPEDFATYYCAQGAALPRTFGQGTKVEIKW

Sequence 2 (SEQ ID NO: 12);
DMS7191
HGEGTFTSDGADLLEGQAAKEFIAWLVKGRGKEAAAKELAADIQMTQSPS
SLSASVGDRVTITCRASQWIGSQLSWYQQKPGKAPKLLIMWRSSLQSGVP
SRFSGSGSGTDFTLTISSLQPEDFATYYCAQGAALPRTFGQGTKVEIKR

Sequence 3 (SEQ ID NO: 13);
DMS7192
HGEGTFTSDVATACEGQAAKEFIACLVKGRGKEAAAKEAAAKEAAAKELA
ADIQMTQSPSSLSASVGDRVTITCRASQWIGSQLSWYQQKPGKAPKLLIM
WRSSLQSGVPSRFSGSGSGTDFTLTISSLQPEDFATYYCAQGAALPRTFG
QGTKVEIKR

Sequence 4 (SEQ ID NO: 14);
DMS7193
HGEGTFTSDVSSYLEGQAAKEFIAWLVTGLEREAAAKEAAAKELAADIQM
TQSPSSLSASVGDRVTITCRASQWIGSQLSWYQQKPGKAPKLLIMWRSSL
QSGVPSRFSGSGSGTDFTLTISSLQPEDFATYYCAQGAALPRTFGQGTKV
EIKR

FIGURE 1 cont.

Sequence 5 (SEQ ID NO: 15);

DMS7194

HGEGTFTSEFVTYLEGQAAKEFIAWLVKGKEAAAKELAADIQMTQSPSSL
SASVGDRVTITCRASQWIGSQLSWYQQKPGKAPKLLIMWRSSLQSGVPSR
FSGSGSGTDFTLTISSLQPEDFATYYCAQGAALPRTFGQGTKVEIKW

Sequence 6 (SEQ ID NO: 16);.

DMS7148

HGEGTFTSDVSSYLEGQAAKEFIADLVEGRGPSSDIQMTQSPSSLSASVG
DRVTITCRASQWIGSQLSWYQQKPGKAPKLLIMWRSSLQSGVPSRFSGSG
SGTDFTLTISSLQPEDFATYYCAQGAALPRTFGQGTKVEIKR1

Sequence 7 (SEQ ID NO: 17);

DMS7149

HGEGTFTSEFVTYLEGQAAKEFIAWLVKGRGPSSDIQMTQSPSSLSASVG
DRVTITCRASQWIGSQLSWYQQKPGKAPKLLIMWRSSLQSGVPSRFSGSG
SGTDFTLTISSLQPEDFATYYCAQGAALPRTFGQGTKVEIKR1

Sequence 8 (SEQ ID NO: 18);

DMS7150

HGEGTFTSDVSSYLEGMTSREFIAWLVKGRGPSSDIQMTQSPSSLSASVG
DRVTITCRASQWIGSQLSWYQQKPGKAPKLLIMWRSSLQSGVPSRFSGSG
SGTDFTLTISSLQPEDFATYYCAQGAALPRTFGQGTKVEIKR1

Sequence 9 (SEQ ID NO: 19);

DMS7151

HGEGTFTSDVSSYLEGQAAKEFIAWLVTGLEPSSDIQMTQSPSSLSASVG
DRVTITCRASQWIGSQLSWYQQKPGKAPKLLIMWRSSLQSGVPSRFSGSG
SGTDFTLTISSLQPEDFATYYCAQGAALPRTFGQGTKVEIKR1

FIGURE 1 cont.

Sequence 10 (SEQ ID NO: 20);

DMS7152

HGEGTFTSDVSSYLEGQAASEFIAWLVVDGGPSSDIQMTQSPSSLSASVG
DRVTITCRASQWIGSQLSWYQQKPGKAPKLLIMWRSSLQSGVPSRFSGSG
SGTDFTLTISSLQPEDFATYYCAQGAALPRTFGQGTKVEIKRl

Sequence 11 (SEQ ID NO: 21);

DMS7161

HGEGTFTSDVSSYLEGQAAKEFIADLVEGRGPSSDIQMTQSPSSLSASVGDRVTIT
CRASQWIGSQLSWYQQKPGKAPKLLIMWRSSLQSGVPSRFSGSGSGTDFTLTISS
LQPEDFATYYCAQGLRHPKTFGQGTKVEIKR a) DMS7148 (Variant 6)

b) DMS7149 (Variant 7)

c) DMS7150 (Variant 8)

d) DMS7151 (Variant 9)

e) DMS7152 (Variant 10)

f) DMS7161 (Variant 11)

METHODS FOR SELECTING PROTEASE RESISTANT POLYPEPTIDES

This application is a 371 of International Application No. PCT/EP2009/066395, filed Dec. 4, 2009, which claims the benefit of U.S. Provisional Application No. 61/120,135, filed Dec. 5, 2008, which is incorporated herein in its entirety.

BACKGROUND OF THE DISCLOSURE

Polypeptides and peptides have become increasingly important agents in a variety of applications, including industrial applications and use as medical, therapeutic and diagnostic agents. However, many therapeutic peptides, polypeptides and proteins are particularly susceptible to degradation in vivo by naturally occurring proteases. Moreover, in certain physiological states, such as inflammatory states (e.g., COPD) and cancer, the amount of proteases present in a tissue, organ or animal (e.g., in the lung, in or adjacent to a tumor) can increase. This increase in proteases can result in accelerated degradation and inactivation of endogenous proteins and of therapeutic peptides, polypeptides and proteins that are administered to treat disease. Accordingly, some agents that have potential for in vivo use (e.g., use in treating, diagnosing or preventing disease in mammals such as humans) have only limited efficacy because they are rapidly degraded and inactivated by proteases.

Protease resistant polypeptides provide several advantages. For example, protease resistant polypeptides remain active in vivo longer than protease sensitive agents and, accordingly, remain functional for a period of time that is sufficient to produce biological effects. A need exists for improved methods to select polypeptides that are resistant to protease degradation and also have desirable biological activity.

Glucagon-like peptide (GLP)-1 is an incretin hormone with potent glucose-dependent insulinotropic and glucagonostatic actions, trophic effects on the pancreatic β cells, and inhibitory effects on gastrointestinal secretion and motility, which combine to lower plasma glucose and reduce glycemic excursions. GLP-1 is an agonist of the GLP-1 receptor. Furthermore, via its ability to enhance satiety, GLP-1 reduces food intake, thereby limiting weight gain, and may even cause weight loss. Taken together, these actions give GLP-1 a unique profile, considered highly desirable for an antidiabetic agent, particularly since the glucose dependency of its antihyperglycemic effects should minimize any risk of severe hypoglycemia. However, its pharmacokinetic/pharmacodynamic profile is such that native GLP-1 is not therapeutically useful. Thus, while GLP-1 is most effective when administered continuously, single subcutaneous injections have short-lasting effects. GLP-1 is highly susceptible to enzymatic degradation in vivo, and cleavage by dipeptidyl peptidase IV (DPP-IV) is probably the most relevant, since this occurs rapidly and generates a noninsulinotropic metabolite. Strategies for harnessing GLP-1's therapeutic potential, based on an understanding of factors influencing its metabolic stability and pharmacokinetic/pharmacodynamic profile, have therefore been the focus of intense research.

Extensive work has been done to attempt to inhibit the peptidase or to modify GLP-1 in such a way that its degradation is slowed down while still maintaining biological activity. WO05/027978 discloses GLP-1 derivatives having a protracted profile of action (and incorporated herein by reference as examples of GLP-1 derivatives and analogues that can be used in the present disclosure). WO 02/46227 discloses heterologous fusion proteins comprising a polypeptide (for example, albumin) fused to GLP-1 or analogues (the disclosure of these analogues is incorporated herein by reference as examples of GLP-1 analogues that can be used in the present disclosure). WO05/003296, WO03/060071, WO03/059934 disclose amino fusion protein wherein GLP-1 has fused with albumin to attempt to increase the half-life of the hormone.

However, despite these efforts a long lasting active GLP-1 has not been produced.

SUMMARY OF THE DISCLOSURE

The disclosure relates to methods for selecting protease resistant peptides or polypeptides and methods for selecting peptides or polypeptides that bind a target ligand with high affinity. The disclosure further relates to a method of producing a repertoire of protease resistant peptides or polypeptides.

In one aspect, the invention is a method for selecting a protease resistant peptide or polypeptide. The method comprises providing a repertoire of peptides or polypeptides, incubating the repertoire and a protease under conditions suitable for protease activity, and recovering a peptide or polypeptide that has a desired biological activity, whereby a protease resistant peptide or polypeptide is selected.

In one embodiment, the repertoire of peptides or polypeptides is expressed in a display system and the protease is a protease which is expressed in the display system or expression host. For example, in one embodiment, the repertoire of peptides or polypeptides is expressed in bacterial cells and the protease is a protease endogenous to a bacteria. Suitably, the conditions for repertoire expression maximize expression and activity of the endogenous protease, such as bacterial protease. Protease expression and activity is maximized, for example, by increasing the time and/or temperature for protein expression of the repertoire in bacteria. For example the incubation time may be from 1 hour to overnight (e.g., from 12 up to 24 hours) or longer (e.g. from 24 up to 48 hours, or longer). In one embodiment, temperature may be from 30 to 37 degrees C. or more. In addition, protease expression may be enhanced by using different bacterial strains and/or modification of media ingredients. Density of the bacterial culture may also be varied. In another embodiment, the display system may be modified e.g. by genetic modification to enhance protease expression.

In one embodiment, the repertoire is provided as a bacteriophage display system wherein the bacteriophage repertoire is expressed and/or amplified in *E. Coli* bacterial cells, such as *E. Coli* TB1 cells, TC1 cells or cells from *E. Coli* strain HB2151. Accordingly, in this embodiment, the bacterial protease is a protease expressed endogenously in *E. coli* cells. In one embodiment, the bacterial protease may be a protease which is expressed in the bacterial periplasm. In one embodiment, protease expression may be during phage production, secretion or in the bacterial supernatant.

Thus, in one embodiment of the disclosure, there is provided a method comprising the steps of taking a bacteriophage library; expressing said library in bacteria under conditions suitable for bacterial protease activity; incubating said expressed library with a target ligand whereby a protease resistant target binding peptide is selected. Optionally, said incubation with a target ligand includes the presence of a further protease.

In another embodiment, the display system is a yeast display system such as *Pichia* and the protease is an endogenous protease which is expressed in yeast cells.

In one embodiment, the method in accordance with the disclosure further comprises combining the repertoire and a further protease under conditions suitable for said further protease activity, and recovering a peptide or polypeptide that has a desired biological activity, whereby a protease resistant peptide or polypeptide is selected. In one embodiment, the protease is combined with the repertoire in solution (ie, the protease is not immobilized on a support). Suitably the further protease is found in one or more of serum, sputum, mucus (e.g., gastric mucus, nasal mucus, bronchial mucus), bronchoalveolar lavage, lung homogenate, lung extract, pancreatic extract, gastric fluid, saliva or tears.

In another aspect, there is provided a method for selecting a protease resistant peptide or polypeptide. The method comprises providing a repertoire of peptides or polypeptides, incubating the repertoire and a first protease under conditions suitable for protease activity and further comprising combining the repertoire with a second protease under conditions suitable for protease activity and recovering a peptide or polypeptide that has a desired biological activity, whereby a protease resistant peptide or polypeptide is selected. In one embodiment of this aspect, the first protease is a protease endogenous to the repertoire display system and the second protease is selected from a protease found in serum, sputum, mucus (e.g., gastric mucus, nasal mucus, bronchial mucus), bronchoalveolar lavage, lung homogenate, lung extract, pancreatic extract, gastric fluid, saliva or tears. It will be appreciated, however, that the "first" and "second" protease steps can be carried out in any order. In addition, it will be appreciated that multiple repeats of any such steps may be encompassed within the method of the disclosure.

In one embodiment of any aspect of the disclosure, said conditions for said further or second protease activity are (i) about 10 μg/ml to about 3 mg/ml protease, (ii) about 20° C. to about 40° C. and (iii) for at least about 30 minutes. In one embodiment, these stringent conditions enable the selection of peptides or polypeptides with high affinity and/or improved Tm. In such case, the peptides and polypeptides may display high affinity in monomeric form.

In one embodiment, in the methods of the disclosure in accordance with any aspect, for said conditions suitable for protease activity about 10 to about 100 μg/ml protease is used. For said conditions suitable for protease activity a temperature of about 30 to about 37° C. (eg, at about 37° C. or about room temperature) may be used. In one embodiment, the repertoire and protease may be combined for at least about one hour (eg, about 1 hour, about two hours, overnight e.g. 18 to 24 hours). In the methods of the disclosure, the repertoire and the protease are in one embodiment incubated for a period of at least about 30 minutes. In one embodiment, the protease is used at about 100 μg/ml, and the combined repertoire and protease are incubated at about 37° C. for at least about hour.

In one embodiment of any aspect of the disclosure, the ratio (on a mole/mole basis) of protease, eg trypsin, to polypeptide or variable domain is 8,000 to 80,000 protease:variable domain. In one embodiment the ratio (on a weight/weight, eg microgram/microgram basis) of protease (eg, trypsin) to polypeptide or variable domain is 16,000 to 160,000 protease:variable domain. In one embodiment, the protease is used at a concentration of at least 100 or 1000 micrograms/ml protease.

Any desired protease can be used in a method in accordance with any aspect of the disclosure, such as one or more of the following, serine protease, cysteine protease, aspartate proteases, thiol proteases, matrix metalloprotease, carboxypeptidase (e.g., carboxypeptidase A, carboxypeptidase B), trypsin, chymotrypsin, pepsin, papain, elastase, leucozyme, pancreatin, thrombin, plasmin, cathepsins (e.g., cathepsin G), proteinase (e.g., proteinase 1, proteinase 2, proteinase 3), thermolysin, chymosin, enteropeptidase, caspase (e.g., caspase 1, caspase 2, caspase 4, caspase 5, caspase 9, caspase 12, caspase 13), calpain, ficain, clostripain, actinidain, bromelain, separase and dipeptidyl peptidase IV (DPP-IV). In particular embodiments, the protease is trypsin, elastase or leucozyme. The protease can also be provided by a biological extract, biological homogenate or biological preparation, eg whole cells in vitro. If desired, the method further comprises adding a protease inhibitor to the combination of the repertoire and the protease after incubation is complete.

In one embodiment of the any of methods of the disclosure, the protease(s) is in solution when combined with the repertoire.

In one embodiment of any aspect of the disclosure, the desired biological activity is binding activity, eg to a ligand, eg a target ligand or a generic ligand.

In some embodiments, a peptide or polypeptide that has a desired biological activity is recovered based on a binding activity. For example, the peptide or polypeptide can be recovered based on binding a generic ligand, such as protein A, protein G or protein L. The binding activity can also be specific binding to a target ligand. Exemplary target ligands include ApoE, Apo-SAA, BDNF, Cardiotrophin-1, CEA, CD40, CD40 Ligand, CD56, CD38, CD138, EGF, EGF receptor, ENA-78, Eotaxin, Eotaxin-2, Exodus-2, FAPα, FGF-acidic, FGF-basic, fibroblast growth factor-10, FLT3 ligand, Fractalkine (CX3C), GDNF, G-CSF, GM-CSF, GF-β1, human serum albumin, insulin, IFN-γ, IGF-I, IGF-II, IL-1α, IL-1β, IL-1 receptor, IL-1 receptor type 1, IL-2, IL-3, IL-4, IL-5, IL-6, IL-7, IL-8 (72 a.a.), IL-8 (77 a.a.), IL-9, IL-10, IL-11, IL-12, IL-13, IL-15, IL-16, IL-17, IL-18 (IGIF), Inhibin α, Inhibin β, IP-10, keratinocyte growth factor-2 (KGF-2), KGF, Leptin, LIF, Lymphotactin, Mullerian inhibitory substance, monocyte colony inhibitory factor, monocyte attractant protein, M-CSF, MDC (67 a.a.), MDC (69 a.a.), MCP-1 (MCAF), MCP-2, MCP-3, MCP-4, MDC (67 a.a.), MDC (69 a.a.), MIG, MIP-1α, MIP-1β, MIP-3α, MIP-3β, MIP-4, myeloid progenitor inhibitor factor-1 (MPIF-1), NAP-2, Neurturin, Nerve growth factor, β-NGF, NT-3, NT-4, Oncostatin M, PDGF-AA, PDGF-AB, PDGF-BB, PF-4, RANTES, SDF1α, SDF1β, SCF, SCGF, stem cell factor (SCF), TARC, TGF-α, TGF-β, TGF-β2, TGF-β3, tumour necrosis factor (TNF), TNF-α, TNF-β, TNF receptor I, TNF receptor II, TNIL-1, TPO, VEGF, VEGF A, VEGF B, VEGF C, VEGF D, VEGF receptor 1, VEGF receptor 2, VEGF receptor 3, GCP-2, GRO/MGSA, GRO-β, GRO-γ, HCC1, 1-309, HER 1, HER 2, HER 3, HER 4, serum albumin, vWF, amyloid proteins (e.g., amyloid alpha), MMP12, PDK1, IgE, IL-13Rα1, IL-13Ra2, IL-15, IL-15R, IL-16, IL-17R, IL-17, IL-18, IL-18R, IL-23 IL-23R, IL-25, CD2, CD4, CD11a, CD23, CD25, CD27, CD28, CD30, CD40, CD40L, CD56, CD138, ALK5, EGFR, FcER1, TGFb, CCL2, CCL18, CEA, CR8, CTGF, CXCL12 (SDF-1), chymase, FGF, Furin, Endothelin-1, Eotaxins (e.g., Eotaxin, Eotaxin-2, Eotaxin-3), GM-CSF, ICAM-1, ICOS, IgE, IFNa, I-309, integrins, L-selectin, MIF, MIP4, MDC, MCP-1, MMPs, neutrophil elastase, osteopontin, OX-40, PARC, PD-1, RANTES, SCF, SDF-1, siglec8, TARC, TGFb, Thrombin, Tim-1, TNF, TRANCE, Tryptase, VEGF, VLA-4, VCAM, α4β7, CCR2, CCR3, CCR4, CCR5, CCR7, CCR8, alphavbeta6, alphavbeta8, cMET, CD8, vWF, amyloid proteins (e.g., amyloid alpha), MMP12, PDK1, and IgE. In another embodiment, the target ligand is GLP-1 receptor, or portions thereof. For example, in the method in accordance with any aspect of the disclosure, the ligand may be GLP-1 receptor extracellular domain.

In particular embodiments of any aspect of the disclosure, the peptide or polypeptide is recovered by panning.

In one embodiment of any of the methods of the disclosure, the repertoire is exposed to a ligand (target ligand; generic ligand) when in the presence of the protease and one or more members of the repertoire are selected based on binding to the ligand.

In some embodiments of any methods of the disclosure, the repertoire comprises a display system. For example, the display system can be bacteriophage display, ribosome display, emulsion compartmentalization and display, yeast display, puromycin display, bacterial display, display on plasmid, or covalent display. Preferred display systems link coding function of a nucleic acid and functional characteristics of the peptide or polypeptide encoded by the nucleic acid. In particular embodiments, the display system comprises replicable genetic packages.

In some embodiments of any methods of the disclosure, the display system comprises bacteriophage display. For example, the bacteriophage can be fd, M13, lambda, MS2 or T7. In particular embodiments, the bacteriophage display system is multivalent. In some embodiments, the peptide or polypeptide is displayed as a pIII fusion protein.

In one embodiment of any methods of the disclosure, the repertoire of peptides or polypeptides (eg, variable domains) is displayed on bacteriophage, for example at a phage library size of $10^6$ to $10^{13}$, eg $10^8$ to $10^{12}$ replicative units (infective virions). In one embodiment, the repertoire is displayed on bacteriophage when incubated with the second or further protease.

In other embodiments of any aspect of the disclosure, the method further comprises amplifying the nucleic acid encoding a peptide or polypeptide that has a desired biological activity. In particular embodiments, the nucleic acid is amplified by phage amplification, cell growth or polymerase chain reaction.

In one embodiment of any aspect of the disclosure, the repertoire of peptides or polypeptides is displayed on bacteriophage which are amplified and expressed in bacterial cells such as *E. Coli*. In this embodiment, the repertoire of peptides or polypeptides are exposed to bacterial protease when expressed in bacterial cells.

In some embodiments, the repertoire is a repertoire of immunoglobulin single variable domains. In particular embodiments, the immunoglobulin single variable domain is a heavy chain variable domain. In more particular embodiments, the heavy chain variable domain is a human heavy chain variable domain. In other embodiments, the immunoglobulin single variable domain is a light chain variable domain. In particular embodiments, the light chain variable domain is a human light chain variable domain.

In another aspect, the disclosure is a method for selecting a peptide or polypeptide that binds a target ligand with high affinity from a repertoire of peptides or polypeptides. The method comprises providing a repertoire of peptides or polypeptides, combining the repertoire and a protease under conditions suitable for protease activity, and recovering a peptide or polypeptide that binds the target ligand.

As per the above methods of the disclosure, where the desired biological activity is binding activity, the ligand that is bound (target ligand; generic ligand) is not the same as the protease(s).

In another aspect, the disclosure is a method of producing a repertoire of protease resistant peptides or polypeptides. The method comprises providing a repertoire of peptides or polypeptides, combining the repertoire of peptides or polypeptides and a protease under suitable conditions for protease activity, and recovering a plurality of peptides or polypeptides that have a desired biological activity, whereby a repertoire of protease resistant peptides or polypeptides is produced.

In some embodiments, a plurality of peptides or polypeptides that have a desired biological activity is recovered based on a binding activity. For example, a plurality of peptides or polypeptides can be recovered based on binding a generic ligand, such as protein A, protein G or protein L.

In another aspect, the disclosure is a method for selecting a protease resistant polypeptide comprising an immunoglobulin single variable domain (dAb) that binds a target ligand from a repertoire. In one embodiment, the method comprises providing a phage display system comprising a repertoire of polypeptides that comprise an immunoglobulin single variable domain, combining the phage display system and a protease selected from the group consisting of elastase, leucozyme and trypsin, under conditions suitable for protease activity, and recovering a phage that displays a polypeptide comprising an immunoglobulin single variable domain that binds the target ligand. Suitably, in one embodiment of this aspect, the method further comprises incubation under conditions for expression of an endogenous protease. For example, an endogenous protease is a protease which is expressed by the display system.

In some embodiments, the protease is used at 100 µg/ml, and the combined phage display system and protease are incubated at about 37° C. overnight.

In some embodiments, the phage that displays a polypeptide comprising an immunoglobulin single variable domain that binds the target ligand is recovered by binding to said target. In other embodiments, the phage that displays a polypeptide comprising an immunoglobulin single variable domain that binds the target ligand is recovered by panning.

The disclosure also relates to an isolated protease resistant peptide or polypeptide selectable or selected by the methods described herein. In a particular embodiment, the disclosure relates to GLP-1 receptor agonists such as GLP-1 peptides as described herein. Suitable GLP-1 peptides and GLP-1 peptide derivatives are set out in the Examples and in FIG. 1. Other suitable peptides include GLP-1 homologues or derivatives such as exendin and its homologues and derivatives. Further suitable derivatives include dipeptidyl peptidase IV resistant derivatives of GLP-1. One preferred peptide is identified by amino acid sequence DMS7148 (sequence 6 in FIG. 1). Another preferred peptide is identified by amino acid sequence DMS7161 (sequence 11 in FIG. 1). Suitably these GLP-1 peptides are fused to an ALBUDAB™ sequence. In another embodiment, the disclosure relates to an isolated protease (e.g., trypsin, elastase, leucozyme) resistant immunoglobulin single variable domain (e.g., human antibody heavy chain variable domain, human antibody light chain variable domain) selectable or selected by the methods described herein.

Advantageously, peptides or polypeptides in accordance with the invention may display improved properties in terms of expression in low cost hosts without proteolysis during expression, thus making them more suitable for industrial scale production.

The disclosure also relates to an isolated or recombinant nucleic acid that encodes a protease resistant peptide or polypeptide (e.g., trypsin-, elastase-, or leucozyme-resistant immunoglobulin single variable domain) selectable or selected by the methods described herein, and to vectors (e.g., expression vectors) and host cells that comprise the nucleic acids.

The disclosure also relates to a method for making a protease resistant peptide or polypeptide (e.g., trypsin-, elastase-, or leucozyme-resistant immunoglobulin single variable domain) selectable or selected by the methods described herein, comprising maintaining a host cell that contains a recombinant nucleic acid encoding the protease resistant peptide or polypeptide under conditions suitable for expression, whereby a protease resistant peptide or polypeptide is produced.

Thus, in the context of any aspect of the present disclosure, the protease may be a protease endogenous to a display system such as a bacterial protease or is found in one or more of serum, sputum, mucus (e.g., gastric mucus, nasal mucus, bronchial mucus), bronchoalveolar lavage, lung homogenate, lung extract, pancreatic extract, gastric fluid, saliva or tears. In one embodiment, the protease is one found in the eye and/or tears. As discussed herein, the selected protease resistant peptides or polypeptides have utility in therapy, prophylaxis and diagnosis of disease or conditions in mammals, eg, humans. In particular, the peptides and polypeptides have utility as the basis of drugs that are likely to encounter proteases when administered to a patient, such as a human.

For example, when administered to the GI tract (eg, orally, sublingually, rectally administered), in which case the peptide or polypeptide may be subjected to protease in one or more of the upper GI tract, lower GI tract, mouth, stomach, small intestine and large intestine. One embodiment, therefore, provides for a protease resistant peptide or polypeptide to be administered orally, sublingually or rectally to the GI tract of a patient to treat and/or prevent a disease or condition in the patient.

For example, in one embodiment the disclosure relates to oral administration of a TNF alpha antagonist peptide or polypeptide selected or selectable by the method of the disclosure, for the treatment and/or prevention of a TNF alpha-mediated condition or disease such as arthritis (eg, rheumatoid arthritis), IBD, psoriasis or Crohn's disease. In this embodiment, the antagonist may be an anti-TNFR1 immunoglobulin single variable domain (dAb). In another example, the peptide or polypeptide is likely to encounter protease when administered (eg, by inhalation or intranasally) to pulmonary tissue (eg, the lung or airways). One embodiment, therefore, provides for a protease resistant peptide or polypeptide to be administered by inhalation or intranasally to pulmonary tissue of a patient to treat and/or prevent a disease or condition in the patient. Such condition may be asthma (eg, allergic asthma), COPD, influenza or any other pulmonary disease or condition disclosed in WO2006038027, incorporated herein by reference.

In another example, the peptide or polypeptide is likely to encounter proteases in serum when administered parenterally, for example through injection e.g. subcutaneously. One embodiment, therefore, provides for a protease resistant peptide or polypeptide to be administered by injection and to treat and/or prevent a disease or condition in the patient. Such condition may be diabetes. In one embodiment, the disclosure provides for parenteral administration of a glucagon like-peptide 1 receptor agonist such as GLP-1 or its homologues and derivates, such as exendin or derivatives thereof, selected or selectable by the method of the disclosure for the treatment and/or prevention of diabetes or diabetes-related disorders.

The peptides and polypeptides according to the disclosure may display improved or relatively high melting temperatures (Tm), providing enhanced stability. High affinity target binding may also be a feature of the peptides and polypeptides. These features, combined with protease resistance, makes the peptides and polypeptides amenable to use as drugs in mammals, such as humans, where proteases are likely to be encountered, eg for GI tract, pulmonary tissue or parenteral administration.

In another example, the peptide or polypeptide (eg, variable domain or antagonist) is likely to encounter protease when administered (eg, by intraocular injection or as eye drops) to an eye of a patient. One embodiment, therefore, provides for ocular administration of the protease resistant peptide, polypeptide, immunoglobulin single variable domain, agonist or antagonist to a patient (eg, to a human) by to treat and/or prevent a disease or condition (eg, a disease or condition of the eye) in the patient. Administration could be topical administration to the eye, in the form of eye drops or by injection into the eye, eg into the vitreous humour.

In one embodiment, the disclosure provides a pulmonary formulation for delivery to the lung, wherein the formulation comprise an agonist, antagonist, peptide, polypeptide or variable domain of the disclosure with a particle size range of less than 5 microns, for example less than 4.5, 4, 3.5 or 3 microns (eg, when in Britton-Robinson buffer, eg at a pH of 6.5 to 8.0, eg at a pH of 7 to 7.5, eg at pH7 or at pH7.5).

In one embodiment, the formulations and compositions of the disclosure are provided at a pH from 6.5 to 8.0, for example 7 to 7.5, for example 7, for example 7.5.

Peptide or polypeptides (eg, variable domains) according to any aspect of the disclosure may have a Tm of at least 50° C., or at least 55° C., or at least 60° C., or at least 65° C., or at least 70° C. An agonist, antagonist, use, method, composition, device or formulation of the disclosure may comprise such a peptide or polypeptide.

In one aspect of the disclosure, the peptides, polypeptides, variable domains, agonists, antagonists, compositions or formulations of the disclosure are substantially stable after incubation (at a concentration of polypeptide or variable domain of 1 mg/ml) at 37 to 50° C. for 14 days in Britton-Robinson buffer. In one embodiment, at least 65, 70, 75, 80, 85, 86, 87, 88, 90, 91, 92, 93, 94, 95, 96, 97, 98, 99% of the peptide, polypeptide, agonists, antagonist or variable domain remains unaggregated after such incubation at 37 degrees C. In one embodiment, at least 65, 70, 75, 80, 85, 86, 87, 88, 90, 91, 92, 93, 94, 95, 96, 97, 98, 99% of the peptide, polypeptide or variable domain remains monomeric after such incubation at 37 degrees C. In one embodiment, at least 5, 10, 15, 20, 25, 30, 35, 40, 45, 50, 55, 60, 65, 70, 75, 80, 85, 86, 87, 88, 90, 91, 92, 93, 94, 95, 96, 97, 98, 99% of the peptide, polypeptide, agonist, antagonist or variable domain remains unaggregated after such incubation at 50 degrees C. In one embodiment, at least 5, 10, 15, 20, 25, 30, 35, 40, 45, 50, 55, 60, 65, 70, 75, 80, 85, 86, 87, 88, 90, 91, 92, 93, 94, 95, 96, 97, 98, 99% of the peptide, polypeptide or variable domain remains monomeric after such incubation at 50 degrees C. In one embodiment, no aggregation of the peptide, polypeptides, variable domains, agonists, antagonists is seen after any one of such incubations. In one embodiment, the pI of the peptide, polypeptide or variable domain remains unchanged or substantially unchanged after incubation at 37 degrees C. at a concentration of polypeptide or variable domain of 1 mg/ml in Britton-Robinson buffer.

In one aspect of the disclosure, the peptide, polypeptides, variable domains, agonists, antagonists, compositions or formulations of the disclosure are substantially stable after incubation (at a concentration of polypeptide or variable domain of 100 mg/ml) at 4° C. for 7 days in Britton-Robinson buffer at a pH of 7 to 7.5 (eg, at pH7 or pH7.5). In one embodiment, at least 95, 95.5, 96, 96.5, 97, 97.5, 98, 98.5, 99 or 99.5% of the peptide, polypeptide, agonist, antagonist or variable domain remains unaggregated after such incubation. In one embodiment, at least 95, 95.5, 96, 96.5, 97, 97.5, 98, 98.5, 99 or 99.5% of the peptide, polypeptide or variable domain remains monomeric after such incubation. In one embodiment, no aggregation of the peptide, polypeptides, variable domains, agonists, antagonists is seen after any one of such incubations.

In one aspect of the disclosure, the peptide, polypeptides, variable domains, agonists, antagonists, compositions or formulations of the disclosure are substantially stable after nebulisation (at a concentration of polypeptide or variable domain of 40 mg/ml) eg, at room temperature, 20 degrees C. or 37° C., for 1 hour, eg in a jet nebuliser, eg a Pari LC+ cup. In one embodiment, at least 65, 70, 75, 80, 85, 86, 87, 88, 90, 91, 92, 93, 94, 95, 95.5, 96, 96.5, 97, 97.5, 98, 98.5, 99 or 99.5% of the peptide, polypeptide, agonist, antagonist or variable domain remains unaggregated after such nebulisation. In one embodiment, at least 65, 70, 75, 80, 85, 86, 87, 88, 90, 91, 92, 93, 94, 95, 95.5, 96, 96.5, 97, 97.5, 98, 98.5, 99 or 99.5% of the peptide, polypeptide or variable domain remains monomeric after such nebulisation. In one embodiment, no aggregation of the peptide, polypeptides, variable domains, agonists, antagonists is seen after any one of such nebulisation.

The peptide or polypeptide can be isolated and/or recombinant.

Suitably in one embodiment of any aspect of the disclosure, the protease resistant peptide or polypeptide is selected from a repertoire of peptides or polypeptides.

The disclosure also relates to a protease resistant peptide or polypeptide (e.g., trypsin-, elastase-, or leucozyme-resistant immunoglobulin single variable domain) selectable or selected by the methods described herein for use in medicine (e.g., for therapy or diagnosis). The disclosure also relates to use of a protease resistant peptide or polypeptide (e.g., trypsin-, elastase-, or leucozyme-resistant immunoglobulin single variable domain) selectable or selected by the methods described herein for the manufacture of a medicament for treating disease. The disclosure also relates to a method of treating a disease, comprising administering to a subject in need thereof, an effective amount of a protease resistant peptide or polypeptide (e.g., trypsin-, elastase-, or leucozyme-resistant immunoglobulin single variable domain) selectable or selected by the methods described herein.

In one embodiment of any aspect of the disclosure, the method further comprises combining a second protease with the repertoire of protease resistant peptides or polypeptides under conditions suitable for activity of the second protease; and recovering at least one peptide or polypeptide that has a desired biological activity, whereby at least one peptide or polypeptide that is resistant to the second protease is selected. The first and second proteases are different. The second protease may be as defined above. In one embodiment, the first or second protease is endogenous to the repertoire display system.

The disclosure further provides an isolated GLP-1 receptor agonist comprising a peptide or polypeptide, that is resistant to one or more protease mentioned above, when incubated with the protease under the conditions suitable for a method of the disclosure, eg a condition of (i) about 10 µg/ml to about 3 mg/ml protease, (ii) about 20° C. to about 40° C. and (iii) for at least about 30 minutes. (eg, under the condition of 100 µg/ml or protease at 37° C. for at least one hour), for administration to a patient for treating and/or preventing diabetes. The agonist may be used for administration by injection.

In one embodiment of the methods of the disclosure, the selected peptide or polypeptide is further assessed for resistance to a second protease or to the first protease but under a set of conditions that differ from those used in the selection method. The second protease is different from the first protease, but otherwise can be any protease described above. In one embodiment, more than one protease resistant peptide or polypeptide is selected in the methods of the disclosure, followed by a further step of determining which of these peptide(s) or polypeptide(s) shows resistance to a second protease or to the first protease but under a set of conditions that differ from those used in the selection method. The second protease is different from the first protease, but otherwise can be any protease described above. In this way, one or more peptides or polypeptides is arrived at which is resistant to more than one protease. In one embodiment, the first or second protease is a protease that is endogenously expressed in the repertoire display system.

In one embodiment of the methods of the disclosure, a protease resistant monomeric peptide or polypeptide (eg, an immunoglobulin single variable domain monomer) is selected.

The medicaments, agonists and antagonists of the disclosure may comprise an antibody constant region (eg, an Fc) fused to said peptide or polypeptide.

In one embodiment, the disclosure provides the use of protease resistant peptide or polypeptide in the manufacture of a medicament for administration to a mammal for providing a medicament with an improved PK. Improved PK may be an improved AUC (area under the curve) and/or an improved half-life. In one embodiment, the protease resistant peptide or polypeptide is selected or selectable by a method of the disclosure. In one embodiment, the peptide or polypeptide is an immunoglobulin single variable domain. The medicament may comprise an antibody constant region fused to said peptide or polypeptide, eg an antibody Fc.

The disclosure provides a medicament comprising a protease resistant peptide or polypeptide for administration to a mammal (eg, a human) for providing a medicament with an improved PK in the mammal. In one embodiment, the protease resistant peptide or polypeptide is selected or selectable by a method of the present disclosure. In one embodiment, the peptide or polypeptide is an immunoglobulin single variable domain. The medicament may comprise an antibody constant region (eg, an Fc) fused to said peptide or polypeptide.

BRIEF DESCRIPTION OF THE DRAWINGS

FIG. 1: Shows sequences of GLP-1-ALBUDAB™ fusion variants 1-10.

FIG. 5a) shows DMS7148 (Variant 6); (Analysis Notes: Measured mass matches the expected mass with a single disulphide (15245.88)); b) shows DMS7149 (Variant 7) (Analysis Notes: Measured mass match residues 24-142 (12860.56), 26-142 (12603.26) and 28-142 (12390.97), all with single disulphides. Each peak has an associated peak that is +42 Da—most probably acetylated.); c) shows DMS7150 (Variant 8) (Analysis Notes: Measured mass matches residues 26-142 with a single disulphide (12603.26).); d) shows DMS7151 (Variant 9) (Analysis Notes: Unable to account for 12960. 12890.5, 12603 and 12391.50 are close matches to residues 24-142, 26-142 and 28-142 respectively, each with a single disulphide (12862.53, 12605.24 and 12392.94). However, there is a 2 Da mass discrepancy between the measured and calculated masses.); e) shows DMS7152 (Variant 10) (Analysis Notes: 12790.5 and 12320.5 match residues 24-142 and 28-142 respectively with single disulphides (12790.42 and 12320.84).) f) shows DMS7161 (Variant 11).

DETAILED DESCRIPTION OF THE DISCLOSURE

Figure 2:
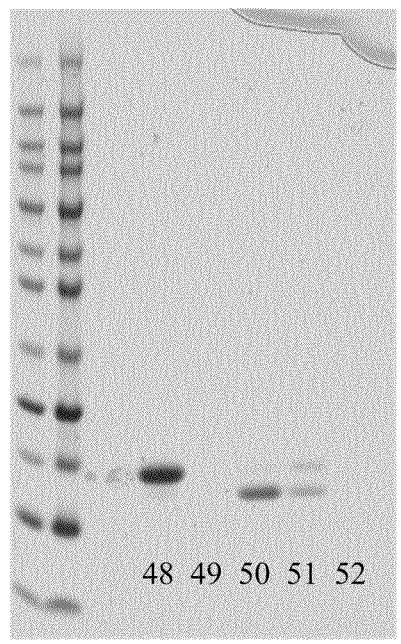
FIG. 2: Shows a gel of GLP-1-ALBUDAB™ fusion variants 6-10.

Within this specification the disclosure has been described, with reference to embodiments, in a way which enables a clear and concise specification to be written. It is intended and should be appreciated that embodiments may be variously combined or separated without parting from the disclosure.

As used herein, "peptide" refers to about two to about 50 amino acids that are joined together via peptide bonds.

As used herein, "polypeptide" refers to at least about 50 amino acids that are joined together by peptide bonds. Polypeptides generally comprise tertiary structure and fold into functional domains.

As used herein, a peptide or polypeptide (e.g. a domain antibody (dAb)) that is "resistant to protease degradation" is not substantially degraded by a protease when incubated with the protease under conditions suitable for protease activity. A polypeptide (e.g., a dAb) is not substantially degraded when no more than about 25%, no more than about 20%, no more than about 15%, no more than about 14%, no more than about 13%, no more than about 12%, no more than about 11%, no more than about 10%, no more than about 9%, no more than about 8%, no more than about 7%, no more than about 6%, no more than about 5%, no more than about 4%, no more than about 3%, no more that about 2%, no more than about 1%, or substantially none of the protein is degraded by protease about incubation with the protease for about one hour at a temperature suitable for protease activity. For example at 37 or 50 degrees C. Protein degradation can be assessed using any suitable method, for example, by SDS-PAGE or by functional assay (e.g., ligand binding) as described herein.

As used herein, "display system" refers to a system in which a collection of polypeptides or peptides are accessible for selection based upon a desired characteristic, such as a physical, chemical or functional characteristic. The display system can be a suitable repertoire of polypeptides or peptides (e.g., in a solution, immobilized on a suitable support). The display system can also be a biochemical system that employs a cellular expression system (e.g., expression of a library of nucleic acids in, e.g., transformed, infected, transfected or transduced cells and display of the encoded polypeptides on the surface of the cells) or an acellular expression system (e.g., emulsion compartmentalization and display). Preferred display systems link the coding function of a nucleic acid and physical, chemical and/or functional characteristics of a polypeptide or peptide encoded by the nucleic acid. When such a display system is employed, polypeptides or peptides that have a desired physical, chemical and/or functional characteristic can be selected and a nucleic acid encoding the selected polypeptide or peptide can be readily isolated or recovered. A number of display systems that link the coding function of a nucleic acid and physical, chemical and/or functional characteristics of a polypeptide or peptide are known in the art, for example, bacteriophage display (phage display), ribosome display, emulsion compartmentalization and display, yeast display, puromycin display, bacterial display, display on plasmid, covalent display and the like. (See, e.g., EP 0436597 (Dyax), U.S. Pat. No. 6,172,197 (McCafferty et al.), U.S. Pat. No. 6,489,103 (Griffiths et al.).)

As used herein, "repertoire" refers to a collection of polypeptides or peptides that are characterized by amino acid sequence diversity. The individual members of a repertoire can have common features, such as common structural features (e.g., a common core structure) and/or common functional features (e.g., capacity to bind a common ligand (e.g., a generic ligand or a target ligand)).

As used herein, "functional" describes a polypeptide or peptide that has biological activity, such as specific binding activity. For example, the term "functional polypeptide" includes an antibody or antigen-binding fragment thereof that binds a target antigen through its antigen-binding site, and an enzyme that binds its substrate(s).

As used herein, "generic ligand" refers to a ligand that binds a substantial portion (e.g., substantially all) of the functional members of a given repertoire. A generic ligand (e.g., a common generic ligand) can bind many members of a given repertoire even though the members may not have binding specificity for a common target ligand. In general, the presence of a functional generic ligand-binding site on a polypeptide (as indicated by the ability to bind a generic ligand) indicates that the polypeptide is correctly folded and functional. Suitable examples of generic ligands include superantigens, antibodies that bind an epitope expressed on a substantial portion of functional members of a repertoire, and the like.

"Superantigen" is a term of art that refers to generic ligands that interact with members of the immunoglobulin superfamily at a site that is distinct from the target ligand-binding sites of these proteins. Staphylococcal enterotoxins are examples of superantigens which interact with T-cell receptors. Superantigens that bind antibodies include Protein G, which binds the IgG constant region (Bjorck and Kronvall, *J. Immunol.*, 133:969 (1984)); Protein A which binds the IgG constant region and $V_H$ domains (Forsgren and Sjoquist, *J. Immunol.*, 97:822 (1966)); and Protein L which binds $V_L$ domains (Bjorck, *J. Immunol.*, 140:1194 (1988)).

As used herein, "target ligand" refers to a ligand which is specifically or selectively bound by a polypeptide or peptide. For example, when a polypeptide is an antibody or antigen-binding fragment thereof, the target ligand can be any desired antigen or epitope, and when a polypeptide is an enzyme, the target ligand can be any desired substrate. Binding to the target antigen is dependent upon the polypeptide or peptide being functional.

As used herein, "antibody format" refers to any suitable polypeptide structure in which an antibody variable domain can be incorporated so as to confer binding specificity for antigen on the structure. A variety of suitable antibody formats are known in the art, such as, chimeric antibodies, humanized antibodies, human antibodies, single chain antibodies, bispecific antibodies, antibody heavy chains, antibody light chains, homodimers and heterodimers of antibody heavy chains and/or light chains, antigen-binding fragments of any of the foregoing (e.g., a Fv fragment (e.g., single chain Fv (scFv), a disulfide bonded Fv), a Fab fragment, a Fab' fragment, a F(ab')$_2$ fragment), a single antibody variable domain (e.g., adAb, $V_H$, $V_{HH}$, $V_L$), and modified versions of any of the foregoing (e.g., modified by the covalent attachment of polyethylene glycol or other suitable polymer).

The phrase "immunoglobulin single variable domain" refers to an antibody variable domain ($V_H$, $V_{HH}$, $V_L$) that specifically binds an antigen or epitope independently of other V regions or domains. An immunoglobulin single variable domain can be present in a format (e.g., homo- or heteromultimer) with other variable regions or variable domains where the other regions or domains are not required for antigen binding by the single immunoglobulin variable domain (i.e., where the immunoglobulin single variable domain binds antigen independently of the additional variable domains). A "domain antibody" or "dAb" is the same as an "immunoglobulin single variable domain" as the term is used herein. An immunoglobulin single variable domain is preferably a human antibody variable domain, but also includes single antibody variable domains from other species such as rodent (for example, as disclosed in WO 00/29004, the contents of which are incorporated herein by reference in their entirety), nurse shark and Camelid $V_{HH}$ dAbs. Camelid $V_{HH}$ are immunoglobulin single variable domain polypeptides that are derived from species including camel, llama, alpaca, dromedary, and guanaco, which produce heavy chain antibodies naturally devoid of light chains.

A "domain" is a folded protein structure which has tertiary structure independent of the rest of the protein. Generally, domains are responsible for discrete functional properties of proteins, and in many cases may be added, removed or transferred to other proteins without loss of function of the remainder of the protein and/or of the domain. A "single antibody variable domain" is a folded polypeptide domain comprising sequences characteristic of antibody variable domains. It therefore includes complete antibody variable domains and modified variable domains, for example, in which one or more loops have been replaced by sequences which are not characteristic of antibody variable domains, or antibody variable domains which have been truncated or comprise N- or C-terminal extensions, as well as folded fragments of variable domains which retain at least the binding activity and specificity of the full-length domain.

The term "library" refers to a mixture of heterogeneous polypeptides or nucleic acids. The library is composed of members, each of which has a single polypeptide or nucleic acid sequence. To this extent, "library" is synonymous with "repertoire." Sequence differences between library members are responsible for the diversity present in the library. The library may take the form of a simple mixture of polypeptides or nucleic acids, or may be in the form of organisms or cells, for example bacteria, viruses, animal or plant cells and the like, transformed with a library of nucleic acids. Preferably, each individual organism or cell contains only one or a limited number of library members. Advantageously, the nucleic acids are incorporated into expression vectors, in order to allow expression of the polypeptides encoded by the nucleic acids. In a preferred aspect, therefore, a library may take the form of a population of host organisms, each organism containing one or more copies of an expression vector containing a single member of the library in nucleic acid form which can be expressed to produce its corresponding polypeptide member. Thus, the population of host organisms has the potential to encode a large repertoire of diverse polypeptides.

A "universal framework" is a single antibody framework sequence corresponding to the regions of an antibody conserved in sequence as defined by Kabat ("Sequences of Proteins of Immunological Interest", US Department of Health and Human Services, 1991) or corresponding to the human germline immunoglobulin repertoire or structure as defined by Chothia and Lesk, (1987) J. Mol. Biol. 196:910-917. The disclosure provides for the use of a single framework, or a set of such frameworks, which has been found to permit the derivation of virtually any binding specificity though variation in the hypervariable regions alone.

Amino acid and nucleotide sequence alignments and homology, similarity or identity, as defined herein are preferably prepared and determined using the algorithm BLAST 2 Sequences, using default parameters (Tatusova, T. A. et al., *FEMS Microbiol Lett,* 174:187-188 (1999)).

The disclosure relates to a method of selection of protease resistant peptides and polypeptides that have a desired biological activity. At least two selective pressures are used in the method to produce an efficient process for selecting polypeptides that are highly stable and resistant to protease degradation, and that have desired biological activity. As described herein, protease resistant peptides and polypeptides generally retain biological activity. In contrast, protease sensitive peptides and polypeptides are cleaved or digested by protease in the methods described herein, and therefore, lose their biological activity. Accordingly, protease resistant peptides or polypeptides are generally selected based on their biological activity, such as binding activity.

The methods described herein provide several advantages. For example, as disclosed and exemplified herein, peptides or polypeptides that are selected for resistance to proteolytic degradation by one protease (e.g., trypsin), are also resistant to degradation by other proteases (e.g., elastase, leucozyme). In addition, protease resistance correlates with a higher melting temperature (Tm) of the peptide or polypeptide. Higher melting temperatures are indicative of more stable peptides and polypeptides. Resistance to protease degradation also correlates with high affinity binding to target ligands. Thus, the methods described herein provide an efficient way to select, isolate and/or recover polypeptides that have a desired biological activity and that are well suited for in vivo therapeutic and/or diagnostic uses because they are protease resistant and stable.

Selection Methods

In one aspect, the disclosure is a method for selecting, isolating and/or recovering a peptide or polypeptide from a library or a repertoire of peptides and polypeptides (e.g., a display system) that is resistant to degradation by a protease (e.g., one or more proteases). Preferably, the method is a method for selecting, isolating and/or recovering a polypeptide from a library or a repertoire of peptides and polypeptides (e.g., a display system) that is resistant to degradation by a protease (e.g., one or more proteases). Generally, the method comprises providing a library or repertoire of peptides or polypeptides, incubating the library or repertoire in the presence of a protease (e.g. a bacterial protease or an exogenously added protease such as trypsin, elastase, leucozyme, pancreatin, sputum) under conditions suitable for protease activity, and selecting, isolating and/or recovering a peptide or polypeptide that is resistant to degradation by the protease and has a desired biological activity. Peptides or polypeptides that are degraded by a protease generally have reduced biological activity or lose their biological activity due to the activity of protease. Accordingly, peptides or polypeptides that are resistant to protease degradation can be selected, isolated and/or recovered using the method based on their biological activity, such as binding activity (e.g., binding a general ligand, binding a specific ligand, binding a substrate), catalytic activity or other biological activity.

As described and exemplified herein, protease resistant dAbs generally bind their target ligand with high affinity. Thus, in another aspect, disclosure is a method for selecting, isolating and/or recovering a peptide or polypeptide that binds a ligand, preferably a target ligand, with high affinity. Preferably, the method is a method for selecting, isolating and/or recovering a polypeptide that binds a ligand, preferably a target ligand, with high affinity. Generally, the method comprises providing a library or repertoire of peptides or polypeptides, combining the library or repertoire with a protease (e.g., trypsin, elastase, leucozyme, pancreatin, sputum) under conditions suitable for protease activity, and selecting, isolating and/or recovering a peptide or polypeptide that binds a ligand (e.g., target ligand). As described herein, the method may also comprise incubating the library or repertoire of peptides or polypeptides under conditions suitable for activity of a protease which is endogenous to the display system such as a bacterial protease (wherein the display system includes expression in bacteria). Because the library or repertoire has been exposed to protease under conditions where protease sensitive peptides or polypeptides will be digested, the activity of protease can eliminate the less stable polypeptides that have low binding affinity, and thereby produce a collection of high affinity binding peptides or polypeptides. For example, the selected peptide of polypeptide can bind its target ligand with an affinity (KD; $KD=K_{off}(kd)/K_{on}$ (ka) as determined by surface plasmon resonance) of 1 µM or stronger, preferably about 500 nM to about 0.5 pM. For example, the high affinity peptide of polypeptide can bind target ligand with an affinity of about 500 nM, about 100 nM, about 10 nM, about 1 nM, about 500 pM, about 100 pM, about 10 pM, about 1 pM or about 0.5 pM. Peptides and polypeptides that are resistant to proteases are believed to have a lower entropy and/or a higher stabilization energy. Thus, the correlation between protease resistance and high affinity binding may be related to the compactness and stability of the surfaces of the peptides and polypeptides selected by the method of the disclosure.

The library or repertoire of peptides or polypeptides is combined with a protease (e.g., one or more proteases) under conditions suitable for proteolytic activity of the protease. Conditions that are suitable for proteolytic activity of protease, and biological preparations or mixtures that contain proteolytic activity, are well-known in the art or can be readily determined by a person of ordinary skill in the art. If desired, suitable conditions can be identified or optimized, for example, by assessing protease activity under a range of pH conditions, protease concentrations, temperatures and/or by varying the amount of time the library or repertoire and the protease are permitted to react. For example, in some embodiments, the ratio (on a mole/mole basis) of protease, eg trypsin, to peptide or polypeptide (eg, variable domain) is 800 to 80,000 (eg, 8,000 to 80,000) protease:peptide or polypeptide, eg when 10 micrograms/ml of protease is used, the ratio is 800 to 80,000 protease:peptide or polypeptide; or when 100 micrograms/ml of protease is used, the ratio is 8,000 to 80,000 protease:peptide or polypeptide. In one embodiment the ratio (on a weight/weight, eg microgram/microgram basis) of protease (eg, trypsin) to peptide or polypeptide (eg, variable domain) is 1,600 to 160,000 (eg, 16,000 to 160,000) protease:peptide or polypeptide eg when 10 micrograms/ml of protease is used, the ratio is 1,600 to 160,000 protease:peptide or polypeptide; or when 100 micrograms/ml of protease is used, the ratio is 16,000 to 160,000 protease:peptide or polypeptide. In one embodiment, the protease is used at a concentration of at least 100 or 1000 micrograms/ml and the protease:peptide ratio (on a mole/mole basis) of protease, eg trypsin, to peptide or polypeptide (eg, variable domain) is 8,000 to 80,000 protease:peptide or polypeptide. In one embodiment, the protease is used at a concentration of at least 10 micrograms/ml and the protease:peptide ratio (on a mole/mole basis) of protease, eg trypsin, to peptide or polypeptide (eg, variable domain) is 800 to 80,000 protease:peptide or polypeptide. In one embodiment the ratio (on a weight/weight, eg microgram/microgram basis) of protease (eg, trypsin) to peptide or polypeptide (eg, variable domain) is 1600 to 160,000 protease:peptide or polypeptide eg when C is 10 micrograms/ml; or when C or C' is 100 micrograms/ml, the ratio is 16,000 to 160,000 protease:peptide or polypeptide. In one embodiment, the concentration (c or c') is at least 100 or 1000 micrograms/ml protease. For testing an individual or isolated peptide or polypeptide (eg, an immunoglobulin variable domain), eg one that has already been isolated from a repertoire or library, a protease can be added to a solution of peptide or polypeptide in a suitable buffer (e.g., PBS) to produce a peptide or polypeptide/protease solution, such as a solution of at least about 0.01% (w/w) protease/peptide or polypeptide, about 0.01% to about 5% (w/w) protease/peptide or polypeptide, about 0.05% to about 5% (w/w) protease/peptide or polypeptide, about 0.1% to about 5% (w/w) protease/peptide or polypeptide, about 0.5% to about 5% (w/w) protease/peptide or polypeptide, about 1% to about 5% (w/w) protease/peptide or polypeptide, at least about 0.01% (w/w) protease/peptide or polypeptide, at least about 0.02% (w/w) protease/peptide or polypeptide, at least about 0.03% (w/w) protease/peptide or polypeptide, at least about 0.04% (w/w) protease/peptide or polypeptide, at least about 0.05% (w/w) protease/peptide or polypeptide, at least about 0.06% (w/w) protease/peptide or polypeptide, at least about 0.07% (w/w) protease/peptide or polypeptide, at least about 0.08% (w/w) protease/peptide or polypeptide, at least about 0.09% (w/w) protease/peptide or polypeptide, at least about 0.1% (w/w) protease/peptide or polypeptide, at least about 0.2% (w/w) protease/peptide or polypeptide, at least about 0.3% (w/w) protease/peptide or polypeptide, at least about 0.4% (w/w) protease/peptide or polypeptide, at least about 0.5% (w/w) protease/peptide or polypeptide, at least about 0.6% (w/w) protease/peptide or polypeptide, at least about 0.7% (w/w) protease/peptide or polypeptide, at least about 0.8% (w/w) protease/peptide or polypeptide, at least about 0.9% (w/w) protease/peptide or polypeptide, at least about 1% (w/w) protease/peptide or polypeptide, at least about 2% (w/w) protease/peptide or polypeptide, at least about 3% (w/w) protease/peptide or polypeptide, at least about 4% (w/w) protease/peptide or polypeptide, or about 5% (w/w) protease/peptide or polypeptide. The mixture can be incubated at a suitable temperature for protease activity (e.g., room temperature, about 37° C.) and samples can be taken at time intervals (e.g., at 1 hour, 2 hours, 3 hours, etc.). The samples can be analyzed for protein degradation using any suitable method, such as SDS-PAGE analysis or ligand binding, and the results can be used to establish a time course of degradation.

Any desired protease or proteases can be used in the methods described herein. For example, a single protease, any desired combination of different proteases, or any biological preparation, biological extract, or biological homogenate that contains proteolytic activity can be used. It is not necessary that the identity of the protease or proteases that are used be known. Suitable examples of proteases that can be used alone or in any desired combination include serine protease, cysteine protease, aspartate proteases, thiol proteases, matrix metalloprotease, carboxypeptidase (e.g., carboxypeptidase A, carboxypeptidase B), trypsin, chymotrypsin, pepsin, papain, elastase, leucozyme, pancreatin, thrombin, plasmin, cathepsins (e.g., cathepsin G), proteinase (e.g., proteinase 1, proteinase 2, proteinase 3), thermolysin, chymosin, enteropeptidase, caspase (e.g., caspase 1, caspase 2, caspase 4, caspase 5, caspase 9, caspase 12, caspase 13), calpain, ficain, clostripain, actinidain, bromelain, separase, dipeptidyl aminopeptidase IV and the like. Suitable biological extracts, homogenates and preparations that contains proteolytic activity include serum, sputum, mucus (e.g., gastric mucus, nasal mucus, bronchial mucus), bronchoalveolar lavage, lung homogenate, lung extract, pancreatic extract, gastric fluid, saliva, tears and the like. In one embodiment, the protease is one found in the eye and/or tears. The protease is used in an amount suitable for proteolytic degradation to occur. For example, as described herein, protease can be used at about 0.01% to about 5% (w/w, protease/peptide or polypeptide). When protease is combined with a display system that comprises the repertoire of peptides or polypeptides (e.g., a phage display system), for example, the protease can be used at a concentration of about 10 µg/ml to about 3 mg/ml, about 10 µg/ml, about 20 µg/ml, about 30 µg/ml, about 40 µg/ml, about 50 µg/ml, about 60 µg/ml, about 70 µg/ml, about 80 µg/ml, about 90 µg/ml, about 100 µg/ml, about 200 µg/ml, about 300 µg/ml, about 400 µg/ml, about 500 µg/ml, about 600 µg/ml, about 700 µg/ml, about 800 µg/ml, about 900 µg/ml, about 1000 µg/ml, about 1.5 mg/ml, about 2 mg/ml, about 2.5 mg/ml or about 3 mg/ml. Suitable concentrations are about 10 µg/ml to 1 mg/ml, 10 µg/ml to 100, 90, 80, 70, 60, 50 or 40 µg/ml, or 10, 20, 30, 40 or 50 µg/ml to 100, 90, 80, 70, 60 µg/ml.

The protease is incubated with the collection of peptides or polypeptides (library or repertoire) at a temperature that is suitable for activity of the protease. For example, the protease and collection of peptides or polypeptides can be incubated at a temperature of about 20° C. to about 40° C. (e.g., at room temperature, about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C.). The protease and the collection of peptides or polypeptides are incubated together for a period of time sufficient for proteolytic degradation to occur. For example, the collection of peptides or polypeptides can be incubated together with protease for about 30 minutes to about 24 or about 48 hours. In some examples, the collection of peptides or polypeptides is incubated together with protease overnight, or for at least about 30 minutes, about 1 hour, about 1.5 hours, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 48 hours, or longer.

It is generally desirable, at least in early selection rounds (e.g. when a display system is used), that the protease results in a reduction in the number of clones that have the desired biological activity that is selected for by at least one order of magnitude, in comparison to selections that do not include incubation with protease. In particular examples, the amount of protease and conditions used in the methods are sufficient to reduce the number of recovered clones by at least about one log (a factor of 10), at least about 2 logs (a factor of 100), at least about 3 logs (a factor of 1000) or at least about 4 logs (a factor of 10,000). Suitable amounts of protease and incubation conditions that will result in the desired reduction in recovered clones can be easily determined using conventional methods and/or the guidance provided herein.

The protease and collection of peptides or polypeptides can be combined and incubated using any suitable method (e.g., in vitro, in vivo or ex vivo). For example, the protease and collection of peptides or polypeptides can be combined in a suitable container and held stationary, rocked, shaken, swirled or the like, at a temperature suitable for protease activity. If desired, the protease and collection of peptides or polypeptides can be combined in an in vivo or ex vivo system, such as by introducing the collection of polypeptides (e.g., a phage display library or repertoire) into a suitable animal (e.g., a mouse), and after sufficient time for protease activity has passed, recovering the collection of peptides or polypeptides. In another example, an organ or tissue is perfused with the collection of polypeptides (e.g., a phage display library or repertoire), and after sufficient time for protease activity has passed, the collection of polypeptides is recovered.

Following incubation, a protease resistant peptide or polypeptide can be selected based on a desired biological activity, such as a binding activity. If desired, a protease inhibitor can be added before selection. Any suitable protease inhibitor (or combination of two or more protease inhibitors) that will not substantially interfere with the selection method can be used. Examples of suitable protease inhibitors include, $\alpha$1-anti-trypsin, $\alpha$2-macroglobulin, amastatin, antipain, antithrombin III, aprotinin, 4-(2-Aminoethyl)benzenesulfonyl fluoride hydrochloride (AEBSF), (4-Amidino-Phenyl)-Methane-Sulfonyl Fluoride (APMSF), bestatin, benzamidine, chymostatin, 3,4-Dichloroisocoumarin, diisopropyl fluorophosphate (DIFP), E-64, ethylenediamine tetraacedic acid (EDTA), elastatinal, leupeptin, N-Ethylmaleimide, phenylmethylsulfonylfluoride (PMSF), pepstatin, 1,10-Phenanthroline, phosphoramidon, serine protease inhibitors, N-tosyl-L-lysine-chloromethyl ketone (TLCK), Na-Tosyl-Phechloromethylketone (TPCK) and the like. In addition, many preparations that contain inhibitors of several classes of proteases are commercially available (e.g., Roche Complete Protease Inhibitor Cocktail Tablets™ (Roche Diagnostics Corporation; Indianapolis, Ind., USA), which inhibits chymotrypsin, thermolysin, papain, pronase, pancreatic extract and trypsin).

A protease resistant peptide or polypeptide can be selected using a desired biological activity selection method, which allows peptides and polypeptides that have the desired biological activity to be distinguished from and selected over peptides and polypeptides that do not have the desired biological activity. Generally, peptides or polypeptides that have been digested or cleaved by protease loose their biological activity, while protease resistant peptides or polypeptides remain functional. Thus, suitable assays for biological activity can be used to select protease resistant peptides or polypeptides. For example, a common binding function (e.g., binding of a general ligand, binding of a specific ligand, or binding of a substrate) can be assessed using a suitable binding assay (e.g., ELISA, panning). For example, polypeptides that bind a target ligand or a generic ligand, such as protein A, protein L or an antibody, can be selected, isolated, and/or recovered by panning or using a suitable affinity matrix. Panning can be accomplished by adding a solution of ligand (e.g., generic ligand, target ligand) to a suitable vessel (e.g., tube, petri dish) and allowing the ligand to become deposited or coated onto the walls of the vessel. Excess ligand can be washed away and polypeptides (e.g., a phage display library) can be added to the vessel and the vessel maintained under conditions suitable for the polypeptides to bind the immobilized ligand. Unbound polypeptide can be washed away and bound polypeptides can be recovered using any suitable method, such as scraping or lowering the pH, for example.

When a phage display system is used, binding can be tested in a phage ELISA. Phage ELISA may be performed according to any suitable procedure. In one example, populations of phage produced at each round of selection can be screened for binding by ELISA to the selected target ligand or generic ligand, to identify phage that display protease resistant peptides or polypeptides. If desired, soluble peptides and polypeptides can be tested for binding to target ligand or generic ligand, for example by ELISA using reagents, for example, against a C- or N-terminal tag (see for example Winter et al. (1994) Ann. Rev. Immunology 12, 433-55 and references cited therein). The diversity of the selected phage may also be assessed by gel electrophoresis of PCR products (Marks et al. 1991, supra; Nissim et al. 1994 supra), probing (Tomlinson et al., 1992) J. Mol. Biol. 227, 776) or by sequencing of the vector DNA.

Protease resistant peptides and polypeptides can also be selected, for example, based on catalytic activity, which can be measured using a catalytic activity assay (e.g., proteolytic activity assay, phosphotransferase assay, phosphohydrolase assay, polymerase activity assay).

The protease resistant peptide or polypeptide (e.g., single antibody variable domain) can have binding specificity for a generic ligand or any desired target ligand, such as human or animal proteins, including cytokines, growth factors, cytokine receptors, growth factor receptors, enzymes (e.g., proteases), co-factors for enzymes, DNA binding proteins, lipids and carbohydrates. Suitable targets antigens, including cytokines, growth factors, cytokine receptors, growth factor receptors and other proteins as described herein. It will be appreciated that this list is by no means exhaustive.

In some embodiments, the protease resistant peptide or polypeptide binds a target in pulmonary tissue, such as a target selected from the group consisting of TNFR1, IL-1, IL-1R, IL-4, IL-4R, IL-5, IL-6, IL-6R, IL-8, IL-8R, IL-9, IL-9R, IL-10, IL-12 IL-12R, IL-13, IL-13Rα1, IL-13Ra2, IL-15, IL-15R, IL-16, IL-17R, IL-17, IL-18, IL-18R, IL-23 IL-23R, IL-25, CD2, CD4, CD11a, CD23, CD25, CD27, CD28, CD30, CD40, CD40L, CD56, CD138, ALK5, EGFR, FcER1, TGFb, CCL2, CCL18, CEA, CR8, CTGF, CXCL12 (SDF-1), chymase, FGF, Furin, Endothelin-1, Eotaxins (e.g., Eotaxin, Eotaxin-2, Eotaxin-3), GM-CSF, ICAM-1, ICOS, IgE, IFNa, I-309, integrins, L-selectin, MIF, MIP4, MDC, MCP-1, MMPs, neutrophil elastase, osteopontin, OX-40, PARC, PD-1, RANTES, SCF, SDF-1, siglec8, TARC, TGFb, Thrombin, Tim-1, TNF, TRANCE, Tryptase, VEGF, VLA-4, VCAM, α4β7, CCR2, CCR3, CCR4, CCR5, CCR7, CCR8, alphavbeta6, alphavbeta8, cMET, CD8, vWF, amyloid proteins (e.g., amyloid alpha), MMP12, PDK1, and IgE.

When a display system (e.g., a display system that links coding function of a nucleic acid and functional characteristics of the peptide or polypeptide encoded by the nucleic acid) is used in the methods described herein it is frequently advantageous to amplify or increase the copy number of the nucleic acids that encode the selected peptides or polypeptides. This provides an efficient way of obtaining sufficient quantities of nucleic acids and/or peptides or polypeptides for additional rounds of selection, using the methods described herein or other suitable methods, or for preparing additional repertoires (e.g., affinity maturation repertoires). Thus, in some embodiments, the methods of the disclosure comprises using a display system (e.g., that links coding function of a nucleic acid and functional characteristics of the peptide or polypeptide encoded by the nucleic acid, such as phage display) and further comprises amplifying or increasing the copy number of a nucleic acid that encodes a selected peptide or polypeptide. Nucleic acids can be amplified using any suitable methods, such as by phage amplification, cell growth or polymerase chain reaction.

The methods described herein can be used as part of a program to isolated protease resistant peptides or polypeptides that can comprise, if desired, other suitable selection methods. In these situations, the methods described herein can be employed at any desired point in the program, such as before or after other selection methods are used. The methods described herein can also be used to provide two or more rounds of selection, as described and exemplified herein.

In another aspect, the disclosure is a method of producing a repertoire of protease resistant peptides or polypeptides. The method comprises providing a repertoire of peptides or polypeptides; combining the repertoire of peptides or polypeptides and a protease under suitable conditions for protease activity; and recovering a plurality of peptides or polypeptides that have a desired biological activity, whereby a repertoire of protease resistant peptides or polypeptides is produced. Preferably, the plurality of peptides or polypeptides that have a desired biological activity are recovered based on a binding activity, such as binding to a generic ligand or a target ligand. Proteases, display systems, conditions for protease activity, and methods for selecting peptides or polypeptides that are suitable for use in the method are described herein with respect to the other methods of the disclosure.

In some embodiments, a display system (e.g., a display system that links coding function of a nucleic acid and functional characteristics of the peptide or polypeptide encoded by the nucleic acid) that comprises a repertoire of peptides or polypeptides is used, and the method further comprises amplifying or increasing the copy number of the nucleic acids that encode the plurality of selected peptides or polypeptides. Nucleic acids can be amplified using any suitable method, such as by phage amplification, cell growth or polymerase chain reaction. In one embodiment, the display system is bacteriophage display and the amplification is through expression in E. Coli. In this embodiment, protease expression in E. Coli can provide the protease for selection of protease resistant peptides or polypeptides.

In particular embodiment, the disclosure is a method of producing a repertoire of protease resistant polypeptides that comprise dAbs. The method comprises providing a repertoire of polypeptides that comprise dAbs; combining the repertoire of peptides or polypeptides and a protease (e.g., trypsin, elastase, leucozyme) under suitable conditions for protease activity; and recovering a plurality of polypeptides that comprise dAbs that have binding specificity for a generic ligand (e.g., protein A, protein G, protein L) or a target ligand. The method can be used to produce a naïve repertoire, or a repertoire that is biased toward a desired binding specificity, such as an affinity maturation repertoire based on a parental dAb that has binding specificity for a desired target ligand.

Polypeptide Display Systems

Preferably, the repertoire or library of peptides or polypeptides provided for use in the methods of the disclosure comprise a suitable display system. The display system preferably resists degradation by protease (e.g., a single protease or a combination of proteases, and any biological extract, homogenate or preparation that contains proteolytic activity (e.g., serum, sputum, mucus (e.g., gastric mucus, nasal mucus, bronchial mucus), bronchoalveolar lavage, lung homogenate, lung extract, pancreatic extract, gastric fluid, saliva, tears and the like). The display system and the link between the display system and the displayed polypeptide is preferably at least as resistant to protease as the most stable peptides or polypeptides of the repertoire. This allows a nucleic acid that encodes a selected displayed polypeptide to be easily isolated and/or amplified.

In one example, a protease resistant peptide or polypeptide can be selected, isolated and/or recovered from a repertoire of peptides or polypeptides that is in solution, or is covalently or noncovalently attached to a suitable surface, such as plastic or glass (e.g., microtiter plate, polypeptide array such as a microarray). For example an array of peptides on a surface in a manner that places each distinct library member (e.g., unique peptide sequence) at a discrete, predefined location in the array can be used. The identity of each library member in such an array can be determined by its spatial location in the array. The locations in the array where binding interactions between a target ligand, for example, and reactive library members occur can be determined, thereby identifying the sequences of the reactive members on the basis of spatial location. (See, e.g., U.S. Pat. No. 5,143,854, WO 90/15070 and WO 92/10092.)

Preferably, the methods employ a display system that links the coding function of a nucleic acid and physical, chemical and/or functional characteristics of the polypeptide encoded by the nucleic acid. Such a display system can comprise a plurality of replicable genetic packages, such as bacteriophage or cells (bacteria). Preferably, the display system comprises a library, such as a bacteriophage display library. Bacteriophage display is a particularly preferred display system.

A number of suitable bacteriophage display systems (e.g., monovalent display and multivalent display systems) have been described. (See, e.g., Griffiths et al., U.S. Pat. No. 6,555, 313 B1 (incorporated herein by reference); Johnson et al., U.S. Pat. No. 5,733,743 (incorporated herein by reference); McCafferty et al., U.S. Pat. No. 5,969,108 (incorporated herein by reference); Mulligan-Kehoe, U.S. Pat. No. 5,702, 892 (Incorporated herein by reference); Winter, G. et al., *Annu. Rev. Immunol.* 12:433-455 (1994); Soumillion, P. et al., *Appl. Biochem. Biotechnol.* 47(2-3):175-189 (1994); Castagnoli, L. et al., *Comb. Chem. High Throughput Screen,* 4(2): 121-133 (2001).) The peptides or polypeptides displayed in a bacteriophage display system can be displayed on any suitable bacteriophage, such as a filamentous phage (e.g., fd, M13, F1), a lytic phage (e.g., T4, T7, lambda), or an RNA phage (e.g., MS2), for example.

Generally, a library of phage that displays a repertoire of peptides or phage polypeptides, as fusion proteins with a suitable phage coat protein (e.g., fd pIII protein), is produced or provided. The fusion protein can display the peptides or polypeptides at the tip of the phage coat protein, or if desired at an internal position. For example, the displayed peptide or polypeptide can be present at a position that is amino-terminal to domain 1 of pIII. (Domain 1 of pIII is also referred to as N1.) The displayed polypeptide can be directly fused to pIII (e.g., the N-terminus of domain 1 of pIII) or fused to pIII using a linker. If desired, the fusion can further comprise a tag (e.g., myc epitope, His tag). Libraries that comprise a repertoire of peptides or polypeptides that are displayed as fusion proteins with a phage coat protein, can be produced using any suitable methods, such as by introducing a library of phage vectors or phagemid vectors encoding the displayed peptides or polypeptides into suitable host bacteria, and culturing the resulting bacteria to produce phage (e.g., using a suitable helper phage or complementing plasmid if desired). Suitably, in one embodiment of the disclosure, suitable conditions for protease expression in the bacteria are selected. The library of phage can be recovered from the culture using any suitable method, such as precipitation and centrifugation.

The display system can comprise a repertoire of peptides or polypeptides that contains any desired amount of diversity. For example, the repertoire can contain peptides or polypeptides that have amino acid sequences that correspond to naturally occurring polypeptides expressed by an organism, group of organisms, desired tissue or desired cell type, or can contain peptides or polypeptides that have random or randomized amino acid sequences. If desired, the polypeptides can share a common core or scaffold. For example, all polypeptides in the repertoire or library can be based on a scaffold selected from protein A, protein L, protein G, a fibronectin domain, an anticalin, CTLA4, a desired enzyme (e.g., a polymerase, a cellulase), or a polypeptide from the immunoglobulin superfamily, such as an antibody or antibody fragment (e.g., an antibody variable domain). The polypeptides in such a repertoire or library can comprise defined regions of random or randomized amino acid sequence and regions of common amino acid sequence. In certain embodiments, all or substantially all polypeptides in a repertoire are of a desired type, such as a desired enzyme (e.g., a polymerase) or a desired antigen-binding fragment of an antibody (e.g., human $V_H$ or human $V_L$). In preferred embodiments, the polypeptide display system comprises a repertoire of polypeptides wherein each polypeptide comprises an antibody variable domain. For example, each polypeptide in the repertoire can contain a $V_H$, a $V_L$ or an Fv (e.g., a single chain Fv). As described herein, the repertoire can be a library of polypeptides based on parental molecules such as GLP-1 or its derivatives such as a dipeptidyl peptidase IV-resistant derivative.

Amino acid sequence diversity can be introduced into any desired region of a peptide or polypeptide or scaffold using any suitable method. For example, amino acid sequence diversity can be introduced into a target region, such as a complementarity determining region of an antibody variable domain or a hydrophobic domain, by preparing a library of nucleic acids that encode the diversified polypeptides using any suitable mutagenesis methods (e.g., low fidelity PCR, oligonucleotide-mediated or site directed mutagenesis, diversification using NNK codons) or any other suitable method. If desired, a region of a polypeptide to be diversified can be randomized.

The size of the polypeptides that make up the repertoire is largely a matter of choice and uniform polypeptide size is not required. Preferably, the polypeptides in the repertoire have at least tertiary structure (form at least one domain).

Selection/Isolation/Recovery

A protease resistant peptide or polypeptide (e.g., a population of protease resistant polypeptides) can be selected, isolated and/or recovered from a repertoire or library (e.g., in a display system) using any suitable method. Preferably, a protease resistant polypeptide is selected or isolated based on a selectable characteristic (e.g., physical characteristic, chemical characteristic, functional characteristic). Suitable selectable functional characteristics include biological activities of the peptides or polypeptides in the repertoire, for example, binding to a generic ligand (e.g., a superantigen), binding to a target ligand (e.g., an antigen, an epitope, a substrate), binding to an antibody (e.g., through an epitope expressed on a peptide or polypeptide), and catalytic activity. (See, e.g., Tomlinson et al., WO 99/20749; WO 01/57065; WO 99/58655.)

In some embodiments, the protease resistant peptide or polypeptide is selected and/or isolated from a library or repertoire of peptides or polypeptides in which substantially all protease resistant peptides or polypeptides share a common selectable feature. For example, the protease resistant peptide or polypeptide can be selected from a library or repertoire in which substantially all protease resistant peptides or polypeptides bind a common generic ligand, bind a common target ligand, bind (or are bound by) a common antibody, or possess a common catalytic activity. This type of selection is particularly useful for preparing a repertoire of protease resistant peptides or polypeptides that are based on a parental peptide or polypeptide that has a desired biological activity, for example, when performing affinity maturation of an immunoglobulin single variable domain.

Selection based on binding to a common generic ligand can yield a collection or population of peptides or polypeptides that contain all or substantially all of the protease resistant peptides or polypeptides that were components of the original library or repertoire. For example, peptides or polypeptides that bind a target ligand or a generic ligand, such as protein A, protein L or an antibody, can be selected, isolated and/or recovered by panning or using a suitable affinity matrix. Panning can be accomplished by adding a solution of ligand (e.g., generic ligand, target ligand) to a suitable vessel (e.g., tube, petri dish) and allowing the ligand to become deposited or coated onto the walls of the vessel. Excess ligand can be washed away and peptides or polypeptides (e.g., a repertoire that has been incubated with protease) can be added to the vessel and the vessel maintained under conditions suitable for peptides or polypeptides to bind the immobilized ligand. Unbound peptides or polypeptides can be washed away and bound peptides or polypeptides can be recovered using any suitable method, such as scraping or lowering the pH, for example.

Suitable ligand affinity matrices generally contain a solid support or bead (e.g., agarose) to which a ligand is covalently or noncovalently attached. The affinity matrix can be combined with peptides or polypeptides (e.g., a repertoire that has been incubated with protease) using a batch process, a column process or any other suitable process under conditions suitable for binding of peptides or polypeptides to the ligand on the matrix. Peptides or polypeptides that do not bind the affinity matrix can be washed away and bound peptides or polypeptides can be eluted and recovered using any suitable method, such as elution with a lower pH buffer, with a mild denaturing agent (e.g., urea), or with a peptide that competes for binding to the ligand. In one example, a biotinylated target ligand is combined with a repertoire under conditions suitable for peptides or polypeptides in the repertoire to bind the target ligand. Bound peptides or polypeptides are recovered using immobilized avidin or streptavidin (e.g., on a bead).

In some embodiments, the generic or target ligand is an antibody or antigen binding fragment thereof. Antibodies or antigen binding fragments that bind structural features of peptides or polypeptides that are substantially conserved in the peptides or polypeptides of a library or repertoire are particularly useful as generic ligands. Antibodies and antigen binding fragments suitable for use as ligands for isolating, selecting and/or recovering protease resistant peptides or polypeptides can be monoclonal or polyclonal and can be prepared using any suitable method.

Libraries/Repertoires

In other aspects, the disclosure relates to repertoires of protease resistant peptides and polypeptides, to libraries that encode protease resistant peptides and polypeptides, and to methods for producing such libraries and repertoires.

Libraries that encode and/or contain protease resistant peptides and polypeptides can be prepared or obtained using any suitable method. The library of the disclosure can be designed to encode protease resistant peptides or polypeptides based on a peptide or polypeptide of interest (e.g., a peptide or polypeptide selected from a library) or can be selected from another library using the methods described herein. For example, a library enriched in protease resistant polypeptides can be prepared using a suitable polypeptide display system.

In one example, a phage display library comprising a repertoire of displayed polypeptides comprising immunoglobulin single variable domains (e.g., $V_H$, Vk, Vλ) is combined with a protease under conditions suitable for protease activity, as described herein. Protease resistant polypeptides are recovered based on a desired biological activity, such as a binding activity (e.g., binding generic ligand, binding target ligand) thereby yielding a phage display library enriched in protease resistant polypeptides.

In another example, a phage display library comprising a repertoire of displayed polypeptides comprising immunoglobulin single variable domains (e.g., $V_H$, VK, Vλ) is first screened to identify members of the repertoire that have binding specificity for a desired target antigen. A collection of polypeptides having the desired binding specificity are recovered and the collection is combined with protease under conditions suitable for proteolytic activity, as described herein. A collection of protease resistant polypeptides that have the desired target binding specificity is recovered, yielding a library enriched in protease resistant and high affinity polypeptides. As described herein, protease resistance in this selection method correlates with high affinity binding.

Libraries that encode a repertoire of a desired type of polypeptides can readily be produced using any suitable method. For example, a nucleic acid sequence that encodes a desired type of polypeptide (e.g., a polymerase, an immunoglobulin variable domain) can be obtained and a collection of nucleic acids that each contain one or more mutations can be prepared, for example by amplifying the nucleic acid using an error-prone polymerase chain reaction (PCR) system, by chemical mutagenesis (Deng et al., *J. Biol. Chem.*, 269:9533 (1994)) or using bacterial mutator strains (Low et al., *J. Mol. Biol.*, 260:359 (1996)).

In other embodiments, particular regions of the nucleic acid can be targeted for diversification. Methods for mutating selected positions are also well known in the art and include, for example, the use of mismatched oligonucleotides or degenerate oligonucleotides, with or without the use of PCR. For example, synthetic antibody libraries have been created by targeting mutations to the antigen binding loops. Random or semi-random antibody H3 and L3 regions have been appended to germline immunoglobulin V gene segments to produce large libraries with unmutated framework regions (Hoogenboom and Winter (1992) supra; Nissim et al. (1994) supra; Griffiths et al. (1994) supra; DeKruif et al. (1995) supra). Such diversification has been extended to include some or all of the other antigen binding loops (Crameri et al. (1996) *Nature Med.*, 2:100; Riechmann et al. (1995) *Bio/Technology*, 13:475; Morphosys, WO 97/08320, supra). In other embodiments, particular regions of the nucleic acid can be targeted for diversification by, for example, a two-step PCR strategy employing the product of the first PCR as a "mega-primer." (See, e.g., Landt, O. et al., *Gene* 96:125-128 (1990).) Targeted diversification can also be accomplished, for example, by SOE PCR. (See, e.g., Horton, R. M. et al., *Gene* 77:61-68 (1989).)

Sequence diversity at selected positions can be achieved by altering the coding sequence which specifies the sequence of the polypeptide such that a number of possible amino acids (e.g., all 20 or a subset thereof) can be incorporated at that position. Using the IUPAC nomenclature, the most versatile codon is NNK, which encodes all amino acids as well as the TAG stop codon. The NNK codon is preferably used in order to introduce the required diversity. Other codons which achieve the same ends are also of use, including the NNN codon, which leads to the production of the additional stop codons TGA and TAA. Such a targeted approach can allow the full sequence space in a target area to be explored.

Preferred libraries comprise protease resistant polypeptides that are members of the immunoglobulin superfamily (e.g., antibodies or portions thereof). For example the libraries can comprise protease resistant antibody polypeptides that have a known main-chain conformation. (See, e.g., Tomlinson et al., WO 99/20749.) Libraries can be prepared in a suitable plasmid or vector. As used herein, vector refers to a discrete element that is used to introduce heterologous DNA into cells for the expression and/or replication thereof. Any suitable vector can be used, including plasmids (e.g., bacterial plasmids), viral or bacteriophage vectors, artificial chromosomes and episomal vectors. Such vectors may be used for simple cloning and mutagenesis, or an expression vector can be used to drive expression of the library. Vectors and plasmids usually contain one or more cloning sites (e.g., a polylinker), an origin of replication and at least one selectable marker gene. Expression vectors can further contain elements to drive transcription and translation of a polypeptide, such as an enhancer element, promoter, transcription termination signal, signal sequences, and the like. These elements can be arranged in such a way as to be operably linked to a cloned insert encoding a polypeptide, such that the polypeptide is expressed and produced when such an expression vector is maintained under conditions suitable for expression (e.g., in a suitable host cell).

Cloning and expression vectors generally contain nucleic acid sequences that enable the vector to replicate in one or more selected host cells. Typically in cloning vectors, this sequence is one that enables the vector to replicate independently of the host chromosomal DNA and includes origins of replication or autonomously replicating sequences. Such sequences are well known for a variety of bacteria, yeast and viruses. The origin of replication from the plasmid pBR322 is suitable for most Gram-negative bacteria, the 2 micron plasmid origin is suitable for yeast, and various viral origins (e.g. SV40, adenovirus) are useful for cloning vectors in mammalian cells. Generally, the origin of replication is not needed for mammalian expression vectors, unless these are used in mammalian cells able to replicate high levels of DNA, such as COS cells.

Cloning or expression vectors can contain a selection gene also referred to as selectable marker. Such marker genes encode a protein necessary for the survival or growth of transformed host cells grown in a selective culture medium. Host cells not transformed with the vector containing the selection gene will therefore not survive in the culture medium. Typical selection genes encode proteins that confer resistance to antibiotics and other toxins, e.g. ampicillin, neomycin, methotrexate or tetracycline, complement auxotrophic deficiencies, or supply critical nutrients not available in the growth media.

Suitable expression vectors can contain a number of components, for example, an origin of replication, a selectable marker gene, one or more expression control elements, such as a transcription control element (e.g., promoter, enhancer, terminator) and/or one or more translation signals, a signal sequence or leader sequence, and the like. Expression control elements and a signal or leader sequence, if present, can be provided by the vector or other source. For example, the transcriptional and/or translational control sequences of a cloned nucleic acid encoding an antibody chain can be used to direct expression.

A promoter can be provided for expression in a desired host cell. Promoters can be constitutive or inducible. For example, a promoter can be operably linked to a nucleic acid encoding an antibody, antibody chain or portion thereof, such that it directs transcription of the nucleic acid. A variety of suitable promoters for procaryotic (e.g., the β-lactamase and lactose promoter systems, alkaline phosphatase, the tryptophan (trp) promoter system, lac, tac, T3, T7 promoters for *E. coli*) and eucaryotic (e.g., simian virus 40 early or late promoter, Rous sarcoma virus long terminal repeat promoter, cytomegalovirus promoter, adenovirus late promoter, EG-1a promoter) hosts are available.

In addition, expression vectors typically comprise a selectable marker for selection of host cells carrying the vector, and, in the case of a replicable expression vector, an origin of replication. Genes encoding products which confer antibiotic or drug resistance are common selectable markers and may be used in procaryotic (e.g., β-lactamase gene (ampicillin resistance), Tet gene for tetracycline resistance) and eucaryotic cells (e.g., neomycin (G418 or geneticin), gpt (mycophenolic acid), ampicillin, or hygromycin resistance genes). Dihydrofolate reductase marker genes permit selection with methotrexate in a variety of hosts. Genes encoding the gene product of auxotrophic markers of the host (e.g., LEU2, URA3, HIS3) are often used as selectable markers in yeast. Use of viral (e.g., baculovirus) or phage vectors, and vectors which are capable of integrating into the genome of the host cell, such as retroviral vectors, are also contemplated.

Suitable expression vectors for expression in prokaryotic (e.g., bacterial cells such as *E. coli*) or mammalian cells include, for example, a pET vector (e.g., pET-12a, pET-36, pET-37, pET-39, pET-40, Novagen and others), a phage vector (e.g., pCANTAB 5 E, Pharmacia), pRIT2T (Protein A fusion vector, Pharmacia), pCDM8, pcDNA1.1/amp, pcDNA3.1, pRc/RSV, pEF-1 (Invitrogen, Carlsbad, Calif.), pCMV-SCRIPT, pFB, pSG5, pXT1 (Stratagene, La Jolla, Calif.), pCDEF3 (Goldman, L. A., et al., *Biotechniques*, 21:1013-1015 (1996)), pSVSPORT (GibcoBRL, Rockville, Md.), pEF-Bos (Mizushima, S., et al., *Nucleic Acids Res.*, 18:5322 (1990)) and the like. Expression vectors which are suitable for use in various expression hosts, such as prokaryotic cells (*E. coli*), insect cells (*Drosophila* Schnieder S2 cells, Sf9), yeast (*P. methanolica, P. pastoris, S. cerevisiae*) and mammalian cells (eg, COS cells) are available.

Preferred vectors are expression vectors that enable the expression of a nucleotide sequence corresponding to a polypeptide library member. Thus, selection with generic and/or target ligands can be performed by separate propagation and expression of a single clone expressing the polypeptide library member. As described above, the preferred selection display system is bacteriophage display. Thus, phage or phagemid vectors may be used. The preferred vectors are phagemid vectors which have an *E. coli.* origin of replication (for double stranded replication) and also a phage origin of replication (for production of single-stranded DNA). The manipulation and expression of such vectors is well known in the art (Hoogenboom and Winter (1992) supra; Nissim et al. (1994) supra). Briefly, the vector can contain a β-lactamase gene to confer selectivity on the phagemid and a lac promoter upstream of an expression cassette that can contain a suitable leader sequence, a multiple cloning site, one or more peptide tags, one or more TAG stop codons and the phage protein pIII. Thus, using various suppressor and non-suppressor strains of *E. coli* and with the addition of glucose, iso-propyl thio-β-D-galactoside (IPTG) or a helper phage, such as VCS M13, the vector is able to replicate as a plasmid with no expression, produce large quantities of the polypeptide library member only or product phage, some of which contain at least one copy of the polypeptide-pIII fusion on their surface.

The libraries and repertoires of the invention can contain antibody formats. For example, the polypeptide contained within the libraries and repertoires can be whole antibodies or fragments thereof, such as Fab, F(ab')$_2$, Fv or scFv fragments, separate $V_H$ or $V_L$ domains, any of which are either modified or unmodified. scFv fragments, as well as other antibody polypeptides, can be readily produced using any suitable method. A number of suitable antibody engineering methods are well known in the art. For example, a scFv can be formed by linking nucleic acids encoding two variable domains with a suitable oligonucleotide that encodes an appropriate linker peptide, such as (Gly-Gly-Gly-Gly-Ser (SEQ ID NO: 24))$_3$ or other suitable linker peptides. The linker bridges the C-terminal end of the first V region and the N-terminal end of the second V region. Similar techniques for the construction of other antibody formats, such as Fv, Fab and F(ab')$_2$ fragments can be used. To format Fab and F(ab')$_2$ fragments, $V_H$ and $V_L$ polypeptides can be combined with constant region segments, which may be isolated from rearranged genes, germline C genes or synthesized from antibody sequence data. A library or repertoire according to the invention can be a $V_H$ or $V_L$ library or repertoire.

The polypeptides comprising a protease resistant variable domain preferably comprise a target ligand binding site and/or a generic ligand binding site. In certain embodiments, the generic ligand binding site is a binding site for a superantigen, such as protein A, protein L or protein G. The variable domains can be based on any desired variable domain, for example a human VH (e.g., $V_H$1a, $V_H$1b, $V_H$2, $V_H$3, $V_H$4, $V_H$5, $V_H$6), a human Vλ (e.g., VλI, VλII, VλIII, VλIV, VλV, VλVI or Vκ1) or a human Vκ (e.g., Vκ2, Vκ3, Vκ4, Vκ5, Vκ6, Vκ7, Vκ8, Vκ9 or Vκ10).

Nucleic Acids, Host Cells and Methods for Producing Protease Resistant Polypeptides The disclosure also relates to isolated and/or recombinant nucleic acids encoding protease resistant peptides or polypeptides e.g., that are selectable or selected by the methods described herein.

Nucleic acids referred to herein as "isolated" are nucleic acids which have been separated away from other material (e.g., other nucleic acids such as genomic DNA, cDNA and/or RNA) in its original environment (e.g., in cells or in a mixture of nucleic acids such as a library). An isolated nucleic acid can be isolated as part of a vector (e.g., a plasmid).

Nucleic acids referred to herein as "recombinant" are nucleic acids which have been produced by recombinant DNA methodology, including methods which rely upon artificial recombination, such as cloning into a vector or chromosome using, for example, restriction enzymes, homologous recombination, viruses and the like, and nucleic acids prepared using the polymerase chain reaction (PCR).

The disclosure also relates to a recombinant host cell which comprises a (one or more) recombinant nucleic acid or expression construct comprising a nucleic acid encoding a protease resistant peptide or polypeptide, e.g., a peptide or polypeptide selectable or selected by the methods described herein. The disclosure also includes a method of preparing a protease resistant peptide or polypeptide, comprising maintaining a recombinant host cell of the disclosure under conditions appropriate for expression of a protease resistant peptide or polypeptide. The method can further comprise the step of isolating or recovering the protease resistant peptide or polypeptide, if desired.

For example, a nucleic acid molecule (i.e., one or more nucleic acid molecules) encoding a protease resistant peptide or polypeptide, or an expression construct (i.e., one or more constructs) comprising such nucleic acid molecule(s), can be introduced into a suitable host cell to create a recombinant host cell using any method appropriate to the host cell selected (e.g., transformation, transfection, electroporation, infection), such that the nucleic acid molecule(s) are operably linked to one or more expression control elements (e.g., in a vector, in a construct created by processes in the cell, integrated into the host cell genome). The resulting recombinant host cell can be maintained under conditions suitable for expression (e.g., in the presence of an inducer, in a suitable animal, in suitable culture media supplemented with appropriate salts, growth factors, antibiotics, nutritional supplements, etc.), whereby the encoded peptide or polypeptide is produced. If desired, the encoded peptide or polypeptide can be isolated or recovered (e.g., from the animal, the host cell, medium, milk). This process encompasses expression in a host cell of a transgenic animal (see, e.g., WO 92/03918, GenPharm International).

The protease resistant peptide or polypeptide selected by the method described herein can also be produced in a suitable in vitro expression system, by chemical synthesis or by any other suitable method.

Polypeptides, dAbs, Agonists, & Antagonists

As described and exemplified herein, protease resistant polypeptides, peptides or dAbs of the disclosure generally bind their target ligand with high affinity. Thus, in another aspect, there is provided a method for selecting, isolating and/or recovering a polypeptide or dAb of the disclosure that binds target antigen with high affinity. Generally, the method comprises providing a library or repertoire of peptides or polypeptides (eg dAbs), combining the library or repertoire with a protease (e.g., trypsin, elastase, leucozyme, pancreatin, sputum) under conditions suitable for protease activity, and selecting, isolating and/or recovering a peptide or polypeptide that binds a ligand (e.g., target ligand). Because the library or repertoire has been exposed to protease under conditions where protease sensitive peptides or polypeptides will be digested, the activity of protease can eliminate the less stable polypeptides that have low binding affinity, and thereby produce a collection of high affinity binding peptides or polypeptides. For example, the polypeptide or dAb of the disclosure can bind target antigen with an affinity ($K_D$; $K_D = K_{off}(kd)/K_{on}(ka)$ as determined by surface plasmon resonance) of 1 μM or stronger, or about 500 nM to about 0.5 pM. For example, the polypeptide or dAb of the disclosure can bind target antigen (eg. TNFR1) with an affinity of about 500 nM, about 100 nM, about 10 nM, about 1 nM, about 500 pM, about 100 pM, about 10 pM, about 1 pM or about 0.5 pM. Although we are not bound by any particular theory, peptides and polypeptides that are resistant to proteases are believed to have a lower entropy and/or a higher stabilization energy. Thus, the correlation between protease resistance and high affinity binding may be related to the compactness and stability of the surfaces of the peptides and polypeptides and dAbs selected by the method described herein.

The polypeptide, dAb, agonist or antagonist can be expressed in *E. coli* or in *Pichia* species (e.g., *P. pastoris*). In one embodiment, the ligand or dAb monomer is secreted in a quantity of at least about 0.5 mg/L when expressed in *E. coli* or in *Pichia* species (e.g., *P. pastoris*). Although, the ligands and dAb monomers described herein can be secretable when expressed in *E. coli* or in *Pichia* species (e.g., *P. pastoris*), they can be produced using any suitable method, such as synthetic chemical methods or biological production methods that do not employ *E. coli* or *Pichia* species.

In some embodiments, the polypeptide, dAb, agonist or antagonist does not comprise a *Camelid* immunoglobulin variable domain, or one or more framework amino acids that are unique to immunoglobulin variable domains encoded by *Camelid* germline antibody gene segments, eg at position 108, 37, 44, 45 and/or 47.

Agonists or antagonists according to the disclosure can be monovalent or multivalent. In some embodiments, the agonist or antagonist is monovalent and contains one binding site that interacts with target antigen, the binding site provided by a polypeptide or dAb of the disclosure. Monovalent agonists or antagonists bind one target antigen and may not induce cross-linking or clustering of target antigen (eg, receptor antigens) on the surface of cells which can lead to activation of the receptor and signal transduction.

In other embodiments, the agonist or antagonist of the disclosure is multivalent. Multivalent agonists or antagonists can contain two or more copies of a particular binding site for target antigen or contain two or more different binding sites that bind target antigen, at least one of the binding sites being provided by a polypeptide or dAb of the disclosure. For example, as described herein the agonist or antagonist can be a dimer, trimer or multimer comprising two or more copies of a particular polypeptide or dAb of the disclosure that binds target antigen, or two or more different polypeptides or dAbs of the disclosure that bind target antigen. In one embodiment, a multivalent antagonist binds a cell surface receptor antigen and does not substantially agonize the antigen (act as an agonist of the antigen) in a standard cell assay.

In certain embodiments, the multivalent agonist or antagonist contains two or more binding sites for a desired epitope or domain of target antigen.

In other embodiments, the polypeptide may be an insulinotropic agent such as a GLP-1 derived peptide. Suitable methods for determining the potency of an insulinotropic agent, resistance to proteases such as DPP-IV, half life after administration and in vivo effects are described, for example in WO 2006/059106.

In other embodiments, the multivalent agonist or antagonist contains two or more binding sites provided by polypeptides or dAbs of the disclosure that bind to different epitopes or domains of target antigen.

In certain embodiments, the polypeptide, dAb, agonist or antagonist of the disclosure are efficacious in models of chronic inflammatory diseases when an effective amount is administered. Generally an effective amount is about 1 mg/kg to about 10 mg/kg (e.g., about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, or about 10 mg/kg). The models of chronic inflammatory disease (see those described in WO2006038027) are recognized by those skilled in the art as being predictive of therapeutic efficacy in humans.

Generally, the present ligands (e.g., agonists, antagonists) will be utilised in purified form together with pharmacologically appropriate carriers. Typically, these carriers include aqueous or alcoholic/aqueous solutions, emulsions or suspensions, any including saline and/or buffered media. Parenteral vehicles include sodium chloride solution, Ringer's dextrose, dextrose and sodium chloride and lactated Ringer's. Suitable physiologically-acceptable adjuvants, if necessary to keep a polypeptide complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringer's dextrose. Preservatives and other additives, such as antimicrobials, antioxidants, chelating agents and inert gases, may also be present (Mack (1982) *Remington's Pharmaceutical Sciences,* 16th Edition). A variety of suitable formulations can be used, including extended release formulations.

The ligands (e.g., antagonists) of the present disclosure may be used as separately administered compositions or in conjunction with other agents. These can include various immunotherapeutic drugs, such as cylcosporine, methotrexate, adriamycin or cisplatinum, and immunotoxins. Pharmaceutical compositions can include "cocktails" of various cytotoxic or other agents in conjunction with the ligands of the present disclosure, or even combinations of ligands according to the present disclosure having different specificities, such as ligands selected using different target antigens or epitopes, whether or not they are pooled prior to administration.

The route of administration of pharmaceutical compositions according to the disclosure may be any of those commonly known to those of ordinary skill in the art. For therapy, including without limitation immunotherapy, the selected ligands thereof of the disclosure can be administered to any patient in accordance with standard techniques.

The administration can be by any appropriate mode, including parenterally, intravenously, intramuscularly, intraperitoneally, transdermally, via the pulmonary route, or also, appropriately, by direct infusion with a catheter. The dosage and frequency of administration will depend on the age, sex and condition of the patient, concurrent administration of other drugs, counterindications and other parameters to be taken into account by the clinician. Administration can be local (e.g., local delivery to the lung by pulmonary administration, e.g., intranasal administration) or systemic as indicated.

The ligands of this disclosure can be lyophilised for storage and reconstituted in a suitable carrier prior to use. This technique has been shown to be effective with conventional immunoglobulins and art-known lyophilisation and reconstitution techniques can be employed. It will be appreciated by those skilled in the art that lyophilisation and reconstitution can lead to varying degrees of antibody activity loss (e.g. with conventional immunoglobulins, IgM antibodies tend to have greater activity loss than IgG antibodies) and that use levels may have to be adjusted upward to compensate.

The compositions containing the present ligands (e.g., agonists, antagonists) or a cocktail thereof can be administered for prophylactic and/or therapeutic treatments. In certain therapeutic applications, an adequate amount to accomplish at least partial inhibition, suppression, modulation, killing, or some other measurable parameter, of a population of selected cells is defined as a "therapeutically-effective dose". Amounts needed to achieve this dosage will depend upon the severity of the disease and the general state of the patient's own immune system, but generally range from 0.005 to 5.0 mg of ligand, e.g. dAb, agonist or antagonist per kilogram of body weight, with doses of 0.05 to 2.0 mg/kg/dose being more commonly used. For prophylactic applications, compositions containing the present ligands or cocktails thereof may also be administered in similar or slightly lower dosages, to prevent, inhibit or delay onset of disease (e.g., to sustain remission or quiescence, or to prevent acute phase). The skilled clinician will be able to determine the appropriate dosing interval to treat, suppress or prevent disease. Treatment or therapy performed using the compositions described herein is considered "effective" if one or more symptoms are reduced (e.g., by at least 10% or at least one point on a clinical assessment scale), relative to such symptoms present before treatment, or relative to such symptoms in an individual (human or model animal) not treated with such composition or other suitable control. Symptoms will obviously vary depending upon the disease or disorder targeted, but can be measured by an ordinarily skilled clinician or technician. Such symptoms can be measured, for example, by monitoring the level of one or more biochemical indicators of the disease or disorder (e.g., levels of an enzyme or metabolite correlated with the disease, affected cell numbers, etc.), by monitoring physical manifestations (e.g., inflammation, tumor size, etc.), or by an accepted clinical assessment scale, for example, the Expanded Disability Status Scale (for multiple sclerosis), the Irvine Inflammatory Bowel Disease Questionnaire (32 point assessment evaluates quality of life with respect to bowel function, systemic symptoms, social function and emotional status—score ranges from 32 to 224, with higher scores indicating a better quality of life), the Quality of Life Rheumatoid Arthritis Scale, or other accepted clinical assessment scale as known in the field. A sustained (e.g., one day or more, or longer) reduction in disease or disorder symptoms by at least 10% or by one or more points on a given clinical scale is indicative of "effective" treatment. Similarly, prophylaxis performed using a composition as described herein is "effective" if the onset or severity of one or more symptoms is delayed, reduced or abolished relative to such symptoms in a similar individual (human or animal model) not treated with the composition.

A composition containing a ligand (e.g., agonist, antagonist) or cocktail thereof according to the present disclosure may be utilised in prophylactic and therapeutic settings to aid in the alteration, inactivation, killing or removal of a select target cell population in a mammal. In addition, the selected repertoires of polypeptides described herein may be used extracorporeally or in vitro selectively to kill, deplete or otherwise effectively remove a target cell population from a heterogeneous collection of cells. Blood from a mammal may be combined extracorporeally with the ligands whereby the undesired cells are killed or otherwise removed from the blood for return to the mammal in accordance with standard techniques.

A composition containing a ligand (e.g., agonist or antagonist) according to the present disclosure may be utilised in prophylactic and therapeutic settings to aid in the alteration, inactivation, killing or removal of a select target cell population in a mammal.

The ligands (e.g., anti-target antigen antagonists, agonists, dAb monomers) can be administered and or formulated together with one or more additional therapeutic or active agents. When a ligand (eg, a dAb) is administered with an additional therapeutic agent, the ligand can be administered before, simultaneously with or subsequent to administration of the additional agent. Generally, the ligand and additional agent are administered in a manner that provides an overlap of therapeutic effect.

In a preferred embodiment of the disclosure pharmaceutical compositions containing a GLP-1 drug or GLP-1 analogue or derivative according to the present disclosure may be administered parenterally to patients in need of such a treatment. Parenteral administration may be performed by subcutaneous, intramuscular or intravenous injection by means of a syringe, optionally a pen-like syringe. Alternatively, parenteral administration can be performed by means of an infusion pump. A further option is a composition which may be a powder or a liquid for the administration of the GLP-1 drug or GLP-1 analogue or derivative in the form of a nasal or pulmonal spray. As a still further option, the GLP-1 drug or GLP-1 analogue or derivative of the disclosure can also be administered transdermally, e.g. from a patch, optionally an iontophoretic patch, or transmucosally, e.g. bucally. In other embodiments the compositions are administered orally, eg as a pill, capsule, drink (eg, marketed as a weight-loss drink for obesity treatment).

A composition for parenteral administration of GLP-1 compounds may, for example, be prepared as described in WO 03/002136 (incorporated herein by reference).

In another embodiment the present disclosure relates to the use of a compound according to the disclosure for the preparation of a medicament for the treatment of hyperglycemia, type 1 diabetes, type 2 diabetes or β-cell deficiency. In specific embodiments for these indications, the drug is selected from an insulinotropic agent, and incretin, a glucagon-like 1 peptide, a GLP-1 peptide, a GLP-1 analogue, a GLP-1 derivative, PYY, a PYY peptide, a PYY analogue, a PYY derivative, Exendin-3, an Exendin-3 peptide, an Exendin-3 analogue, an Exendin-3 derivative, Exendin-4, an Exendin-4 peptide, an Exendin-4 analogue, an Exendin-4 derivative or a combination of two or more of these (eg, GLP-1 peptide and a PYY peptide).

The treatment with a compound according to the present disclosure may also be combined with a second or more pharmacologically active substances which may or may not be part of the drug conjugate or fusion. For example, an active selected from antidiabetic agents, antiobesity agents, appetite regulating agents, antihypertensive agents, agents for the treatment and/or prevention of complications resulting from or associated with diabetes and agents for the treatment and/or prevention of complications and disorders resulting from or associated with obesity. In the present context the expression "antidiabetic agent" includes compounds for the treatment and/or prophylaxis of insulin resistance and diseases wherein insulin resistance is the pathophysiological mechanism.

Formats

Increased half-life is useful in in vivo applications of immunoglobulins, especially antibodies and most especially antibody fragments of small size. Such fragments (Fvs, disulphide bonded Fvs, Fabs, scFvs, dAbs) suffer from rapid clearance from the body; thus, whilst they are able to reach most parts of the body rapidly, and are quick to produce and easier to handle, their in vivo applications have been limited by their only brief persistence in vivo. One embodiment of the disclosure solves this problem by providing increased half-life of the ligands in vivo and consequently longer persistence times in the body of the functional activity of the ligand.

Methods for pharmacokinetic analysis and determination of ligand half-life will be familiar to those skilled in the art. Details may be found in Kenneth, A et al: Chemical Stability of Pharmaceuticals: A Handbook for Pharmacists and in Peters et al, Pharmacokinetic analysis: A Practical Approach (1996). Reference is also made to "Pharmacokinetics", M Gibaldi & D Perron, published by Marcel Dekker, $2^{nd}$ Rev. ex edition (1982), which describes pharmacokinetic parameters such as t alpha and t beta half lives and area under the curve (AUC).

Half lives (t½ alpha and t½ beta) and AUC can be determined from a curve of serum concentration of ligand against time. The WinNonlin analysis package (available from Pharsight Corp., Mountain View, Calif. 94040, USA) can be used, for example, to model the curve. In a first phase (the alpha phase) the ligand is undergoing mainly distribution in the patient, with some elimination. A second phase (beta phase) is the terminal phase when the ligand has been distributed and the serum concentration is decreasing as the ligand is cleared from the patient. The t alpha half life is the half life of the first phase and the t beta half life is the half life of the second phase. Thus, in one embodiment, the present disclosure provides a ligand or a composition comprising a ligand according to the disclosure having a tα half-life in the range of 15 minutes or more. In one embodiment, the lower end of the range is 30 minutes, 45 minutes, 1 hour, 2 hours, 3 hours, 4 hours, 5 hours, 6 hours, 7 hours, 10 hours, 11 hours or 12 hours. In addition, or alternatively, a ligand or composition according to the disclosure will have a tα half life in the range of up to and including 12 hours. In one embodiment, the upper end of the range is 11, 10, 9, 8, 7, 6 or 5 hours. An example of a suitable range is 1 to 6 hours, 2 to 5 hours or 3 to 4 hours.

In one embodiment, the present disclosure provides a ligand (polypeptide, dAb, agonist or antagonist) or a composition comprising a ligand according to the disclosure having a tβ half-life in the range of 2.5 hours or more. In one embodiment, the lower end of the range is 3 hours, 4 hours, 5 hours, 6 hours, 7 hours, 10 hours, 11 hours, or 12 hours. In addition, or alternatively, a ligand or composition according to the disclosure has a tβ half-life in the range of up to and including 21 days. In one embodiment, the upper end of the range is 12 hours, 24 hours, 2 days, 3 days, 5 days, 10 days, 15 days or 20 days. In one embodiment a ligand or composition according to the disclosure will have a tβ half life in the range 12 to 60 hours. In a further embodiment, it will be in the range 12 to 48 hours. In a further embodiment still, it will be in the range 12 to 26 hours.

In addition, or alternatively to the above criteria, the present disclosure provides a ligand or a composition comprising a ligand according to the disclosure having an AUC value (area under the curve) in the range of 1 mg·min/ml or more. In one embodiment, the lower end of the range is 5, 10, 15, 20, 30, 100, 200 or 300 mg·min/ml. In addition, or alternatively, a ligand or composition according to the disclosure has an AUC in the range of up to 600 mg·min/ml. In one embodiment, the upper end of the range is 500, 400, 300, 200, 150, 100, 75 or 50 mg·min/ml. In one embodiment a ligand according to the disclosure will have a AUC in the range selected from the group consisting of the following: 15 to 150 mg·min/ml, 15 to 100 mg·min/ml, 15 to 75 mg·min/ml, and 15 to 50 mg·min/ml.

Polypeptides and dAbs of the disclosure and agonists or antagonists comprising these can be formatted to have a larger hydrodynamic size, for example, by attachment of a PEG group, serum albumin, transferrin, transferrin receptor or at least the transferrin-binding portion thereof, an antibody Fc region, or by conjugation to an antibody domain. For example, polypeptides dAbs, agonists and antagonists formatted as a larger antigen-binding fragment of an antibody or as an antibody (e.g., formatted as a Fab, Fab', F(ab)$_2$, F(ab')$_2$, IgG, scFv).

Hydrodynamic size of the ligands (e.g., dAb monomers and multimers) of the in disclosure vention may be determined using methods which are well known in the art. For example, gel filtration chromatography may be used to determine the hydrodynamic size of a ligand. Suitable gel filtration matrices for determining the hydrodynamic sizes of ligands, such as cross-linked agarose matrices, are well known and readily available.

The size of a ligand format (e.g., the size of a PEG moiety attached to a dAb monomer), can be varied depending on the desired application. For example, where ligand is intended to leave the circulation and enter into peripheral tissues, it is desirable to keep the hydrodynamic size of the ligand low to facilitate extravazation from the blood stream. Alternatively, where it is desired to have the ligand remain in the systemic circulation for a longer period of time the size of the ligand can be increased, for example by formatting as an Ig like protein.

Half-Life Extension by Targeting an Antigen or Epitope that Increases Half-Live In Vivo The hydrodynamine size of a ligand and its serum half-life can also be increased by conjugating or associating a target antigen binding polypeptide, dAb, agonist or antagonist of the disclosure to a binding domain (e.g., antibody or antibody fragment) that binds an antigen or epitope that increases half-live in vivo, as described herein. For example, the target antigen binding agent (e.g., polypeptide) can be conjugated or linked to an anti-serum albumin or anti-neonatal Fc receptor antibody or antibody fragment, eg an anti-SA or anti-neonatal Fc receptor dAb, Fab, Fab' or scFv, or to an anti-SA affibody or anti-neonatal Fc receptor Affibody or an anti-SA avimer, or an anti-SA binding domain which comprises a scaffold selected from, but preferably not limited to, the group consisting of CTLA-4, lipocallin, SpA, an affibody, an avimer, GroE1 and fibronectin (see PCT/GB2008/000453 filed 8 Feb. 2008 for disclosure of these binding domain, which domains and their sequences are incorporated herein by reference and form part of the disclosure of the present text). Conjugating refers to a composition comprising polypeptide, dAb, agonist or antagonist of the disclosure that is bonded (covalently or noncovalently) to a binding domain that binds serum albumin.

Suitable polypeptides that enhance serum half-life in vivo include, for example, transferrin receptor specific ligand-neuropharmaceutical agent fusion proteins (see U.S. Pat. No. 5,977,307, the teachings of which are incorporated herein by reference), brain capillary endothelial cell receptor, transferrin, transferrin receptor (e.g., soluble transferrin receptor), insulin, insulin-like growth factor 1 (IGF 1) receptor, insulin-like growth factor 2 (IGF 2) receptor, insulin receptor, blood coagulation factor X, α1-antitrypsin and HNF 1α. Suitable polypeptides that enhance serum half-life also include alpha-1 glycoprotein (orosomucoid; AAG), alpha-1 antichymotrypsin (ACT), alpha-1 microglobulin (protein HC; AIM), antithrombin III (AT III), apolipoprotein A-1 (Apo A-1), apolipoprotein B (Apo B), ceruloplasmin (Cp), complement component C3 (C3), complement component C4 (C4), C1 esterase inhibitor (C1 INH), C-reactive protein (CRP), ferritin (FER), hemopexin (HPX), lipoprotein(a) (Lp(a)), mannose-binding protein (MBP), myoglobin (Myo), prealbumin (transthyretin; PAL), retinol-binding protein (RBP), and rheumatoid factor (RF).

Suitable proteins from the extracellular matrix include, for example, collagens, laminins, integrins and fibronectin. Collagens are the major proteins of the extracellular matrix. About 15 types of collagen molecules are currently known, found in different parts of the body, e.g. type I collagen (accounting for 90% of body collagen) found in bone, skin, tendon, ligaments, cornea, internal organs or type II collagen found in cartilage, vertebral disc, notochord, and vitreous humor of the eye.

Suitable proteins from the blood include, for example, plasma proteins (e.g., fibrin, α-2 macroglobulin, serum albumin, fibrinogen (e.g., fibrinogen A, fibrinogen B), serum amyloid protein A, haptoglobin, profilin, ubiquitin, uteroglobulin and β-2-microglobulin), enzymes and enzyme inhibitors (e.g., plasminogen, lysozyme, cystatin C, alpha-1-antitrypsin and pancreatic trypsin inhibitor), proteins of the immune system, such as immunoglobulin proteins (e.g., IgA, IgD, IgE, IgG, IgM, immunoglobulin light chains (kappa/lambda)), transport proteins (e.g., retinol binding protein, α-1 microglobulin), defensins (e.g., beta-defensin 1, neutrophil defensin 1, neutrophil defensin 2 and neutrophil defensin 3) and the like.

Suitable proteins found at the blood brain barrier or in neural tissue include, for example, melanocortin receptor, myelin, ascorbate transporter and the like.

Suitable polypeptides that enhance serum half-life in vivo also include proteins localized to the kidney (e.g., polycystin, type IV collagen, organic anion transporter K1, Heymann's antigen), proteins localized to the liver (e.g., alcohol dehydrogenase, G250), proteins localized to the lung (e.g., secretory component, which binds IgA), proteins localized to the heart (e.g., HSP 27, which is associated with dilated cardiomyopathy), proteins localized to the skin (e.g., keratin), bone specific proteins such as morphogenic proteins (BMPs), which are a subset of the transforming growth factor β superfamily of proteins that demonstrate osteogenic activity (e.g., BMP-2, BMP-4, BMP-5, BMP-6, BMP-7, BMP-8), tumor specific proteins (e.g., trophoblast antigen, herceptin receptor, oestrogen receptor, cathepsins (e.g., cathepsin B, which can be found in liver and spleen)).

Suitable disease-specific proteins include, for example, antigens expressed only on activated T-cells, including LAG-3 (lymphocyte activation gene), osteoprotegerin ligand (OPGL; see *Nature* 402, 304-309 (1999)), OX40 (a member of the TNF receptor family, expressed on activated T cells and specifically up-regulated in human T cell leukemia virus type-I (HTLV-I)-producing cells; see *Immunol.* 165 (1):263-70 (2000)). Suitable disease-specific proteins also include, for example, metalloproteases (associated with arthritis/cancers) including CG6512 *Drosophila*, human paraplegin, human FtsH, human AFG3L2, murine ftsH; and angiogenic growth factors, including acidic fibroblast growth factor (FGF-1), basic fibroblast growth factor (FGF-2), vascular endothelial growth factor/vascular permeability factor (VEGF/VPF), transforming growth factor-α (TGF α), tumor necrosis factor-alpha (TNF-α), angiogenin, interleukin-3 (IL-3), interleukin-8 (IL-8), platelet-derived endothelial growth factor (PD-ECGF), placental growth factor (P1GF), midkine platelet-derived growth factor-BB (PDGF), and fractalkine.

Suitable polypeptides that enhance serum half-life in vivo also include stress proteins such as heat shock proteins (HSPs). HSPs are normally found intracellularly. When they are found extracellularly, it is an indicator that a cell has died and spilled out its contents. This unprogrammed cell death (necrosis) occurs when as a result of trauma, disease or injury, extracellular HSPs trigger a response from the immune system. Binding to extracellular HSP can result in localizing the compositions of the disclosure to a disease site.

Suitable proteins involved in Fc transport include, for example, Brambell receptor (also known as FcRB). This Fc receptor has two functions, both of which are potentially useful for delivery. The functions are (1) transport of IgG from mother to child across the placenta (2) protection of IgG from degradation thereby prolonging its serum half-life. It is thought that the receptor recycles IgG from endosomes. (See, Holliger et al, *Nat Biotechnol* 15(7):632-6 (1997).)

dAbs that Bind Serum Albumin (ALBUDABs™)

The disclosure in one embodiment provides a polypeptide, agonist or antagonist (e.g., dual specific ligand comprising an anti-target antigen dAb (a first dAb)) that binds to target antigen and a second dAb that binds serum albumin (SA), the second dAb binding SA with a $K_D$ as determined by surface plasmon resonance of 1 nM to 1, 2, 3, 4, 5, 10, 20, 30, 40, 50, 60, 70, 100, 200, 300, 400 or 500 μM (i.e., ×10$^{-9}$ to 5×10$^{-4}$), or 100 nM to 10 μM, or 1 to 5 μM or 3 to 70 nM or 10 nM to 1, 2, 3, 4 or 5 μM. For example 30 to 70 nM as determined by surface plasmon resonance. In one embodiment, the first dAb (or a dAb monomer) binds SA (e.g., HSA) with a $K_D$ as determined by surface plasmon resonance of approximately 1, 50, 70, 100, 150, 200, 300 nM or 1, 2 or 3 μM. In one embodiment, for a dual specific ligand comprising a first anti-SA dAb and a second dAb to target antigen, the affinity (eg $K_D$ and/or $K_{off}$ as measured by surface plasmon resonance, eg using BIACORE™) of the second dAb for its target is from 1 to 100000 times (eg, 100 to 100000, or 1000 to 100000, or 10000 to 100000 times) the affinity of the first dAb for SA. In one embodiment, the serum albumin is human serum albumin (HSA). For example, the first dAb binds SA with an affinity of approximately 10 μM, while the second dAb binds its target with an affinity of 100 pM. In one embodiment, the serum albumin is human serum albumin (HSA). In one embodiment, the first dAb binds SA (eg, HSA) with a $K_D$ of approximately 50, for example 70, 100, 150 or 200 nM. Details of dual specific ligands are found in WO03002609, WO04003019 and WO04058821.

The ligands of the disclosure can in one embodiment comprise a dAb that binds serum albumin (SA) with a $K_D$ as determined by surface plasmon resonance of 1 nM to 1, 2, 3, 4, 5, 10, 20, 30, 40, 50, 60, 70, 100, 200, 300, 400 or 500 μM (i.e., ×10$^{-9}$ to 5×10$^{-4}$), or 100 nM to 10 μM, or 1 to 5 μM or 3 to 70 nM or 10 nM to 1, 2, 3, 4 or 5 μM. For example 30 to 70 nM as determined by surface plasmon resonance. In one embodiment, the first dAb (or a dAb monomer) binds SA (e.g., HSA) with a $K_D$ as determined by surface plasmon resonance of approximately 1, 50, 70, 100, 150, 200, 300 nM or 1, 2 or 3 μM. In one embodiment, the first and second dAbs are linked by a linker, for example a linker of from 1 to 4 amino acids or from 1 to 3 amino acids, or greater than 3 amino acids or greater than 4, 5, 6, 7, 8, 9, 10, 15 or 20 amino acids. In one embodiment, a longer linker (greater than 3 amino acids) is used to enhance potency ($K_D$ of one or both dAbs in the agonist or antagonist). In one embodiment, the linker is a helical linker.

In particular embodiments of the ligands, agonists and antagonists, the dAb binds human serum albumin and competes for binding to albumin with a dAb selected from the group consisting of MSA-16, MSA-26 (See WO04003019 for disclosure of these sequences, which sequences and their nucleic acid counterpart are incorporated herein by reference and form part of the disclosure of the present text), DOM7m-16 (SEQ ID NO: 473), DOM7m-12 (SEQ ID NO: 474), DOM7m-26 (SEQ ID NO: 475), DOM7r-1 (SEQ ID NO: 476), DOM7r-3 (SEQ ID NO: 477), DOM7r-4 (SEQ ID NO: 478), DOM7r-5 (SEQ ID NO: 479), DOM7r-7 (SEQ ID NO: 480), DOM7r-8 (SEQ ID NO: 481), DOM7h-2 (SEQ ID NO: 482), DOM7h-3 (SEQ ID NO: 483), DOM7h-4 (SEQ ID NO: 484), DOM7h-6 (SEQ ID NO: 485), DOM7h-1 (SEQ ID NO: 486), DOM7h-7 (SEQ ID NO: 487), DOM7h-22 (SEQ ID NO: 489), DOM7h-23 (SEQ ID NO: 490), DOM7h-24 (SEQ ID NO: 491), DOM7h-25 (SEQ ID NO: 492), DOM7h-26 (SEQ ID NO: 493), DOM7h-21 (SEQ ID NO: 494), DOM7h-27 (SEQ ID NO: 495), DOM7h-8 (SEQ ID NO: 496), DOM7r-13 (SEQ ID NO: 497), DOM7r-14 (SEQ ID NO: 498), DOM7r-15 (SEQ ID NO: 499), DOM7r-16 (SEQ ID NO: 500), DOM7r-17 (SEQ ID NO: 501), DOM7r-18 (SEQ ID NO: 502), DOM7r-19 (SEQ ID NO: 503), DOM7r-20 (SEQ ID NO: 504), DOM7r-21 (SEQ ID NO: 505), DOM7r-22 (SEQ ID NO: 506), DOM7r-23 (SEQ ID NO: 507), DOM7r-24 (SEQ ID NO: 508), DOM7r-25 (SEQ ID NO: 509), DOM7r-26 (SEQ ID NO: 510), DOM7r-27 (SEQ ID NO: 511), DOM7r-28 (SEQ ID NO: 512), DOM7r-29 (SEQ ID NO: 513), DOM7r-30 (SEQ ID NO: 514), DOM7r-31 (SEQ ID NO: 515), DOM7r-32 (SEQ ID NO: 516), DOM7r-33 (SEQ ID NO: 517) (See WO2007080392 for disclosure of these sequences, which sequences and their nucleic acid counterpart are incorporated herein by reference and form part of the disclosure of the present text; the SEQ ID No's in this paragraph are those that appear in WO2007080392), dAb8 (dAb10), dAb 10, dAb36, dAb7r20 (DOM7r20), dAb7r21 (DOM7r21), dAb7r22 (DOM7r22), dAb7r23

(DOM7r23), dAb7r24 (DOM7r24), dAb7r25 (DOM7r25), dAb7r26 (DOM7r26), dAb7r27 (DOM7r27), dAb7r28 (DOM7r28), dAb7r29 (DOM7r29), dAb7r29 (DOM7r29), dAb7r31 (DOM7r31), dAb7r32 (DOM7r32), dAb7r33 (DOM7r33), dAb7r33 (DOM7r33), dAb7h22 (DOM7h22), dAb7h23 (DOM7h23), dAb7h24 (DOM7h24), dAb7h25 (DOM7h25), dAb7h26 (DOM7h26), dAb7h27 (DOM7h27), dAb7h30 (DOM7h30), dAb7h31 (DOM7h31), dAb2 (dAbs 4,7,41), dAb4, dAb7, dAb11, dAb12 (dAb7m12), dAb13 (dAb 15), dAb15, dAb16 (dAb21, dAb7m16), dAb17, dAb18, dAb19, dAb21, dAb22, dAb23, dAb24, dAb25 (dAb26, dAb7m26), dAb27, dAb30 (dAb35), dAb31, dAb33, dAb34, dAb35, dAb38 (dAb54), dAb41, dAb46 (dAbs 47, 52 and 56), dAb47, dAb52, dAb53, dAb54, dAb55, dAb56, dAb7m12, dAb7m16, dAb7m26, dAb7r1 (DOM7r1), dAb7r3 (DOM7r3), dAb7r4 (DOM7r4), dAb7r5 (DOM7r5), dAb7r7 (DOM7r7), dAb7r8 (DOM7r8), dAb7r13 (DOM7r13), dAb7r14 (DOM7r14), dAb7r15 (DOM7r15), dAb7r16 (DOM7r16), dAb7r17 (DOM7r17), dAb7r18 (DOM7r18), dAb7r19 (DOM7r19), dAb7h1 (DOM7h1), dAb7h2 (DOM7h2), dAb7h6 (DOM7h6), dAb7h7 (DOM7h7), dAb7h8 (DOM7h8), dAb7h9 (DOM7h9), dAb7h10 (DOM7h10), dAb7h11 (DOM7h11), dAb7h12 (DOM7h12), dAb7h13 (DOM7h13), dAb7h14 (DOM7h14), dAb7p1 (DOM7p1), and dAb7p2 (DOM7p2) (see WO2008096158 for disclosure of these sequences, which sequences and their nucleic acid counterpart are incorporated herein by reference and form part of the disclosure of the present text). Alternative names are shown in brackets after the dAb, e.g. dAb8 has an alternative name which is dAb10 i.e. dAb8 (dAb10).

In certain embodiments, the dAb binds human serum albumin and comprises an amino acid sequence that has at least about 80%, or at least about 85%, or at least about 90%, or at least about 95%, or at least about 96%, or at least about 97%, or at least about 98%, or at least about 99% amino acid sequence identity with the amino acid sequence of a dAb selected from the group consisting of

MSA-16, MSA-26,

DOM7m-16 (SEQ ID NO: 473), DOM7m-12 (SEQ ID NO: 474), DOM7m-26 (SEQ ID NO: 475), DOM7r-1 (SEQ ID NO: 476), DOM7r-3 (SEQ ID NO: 477), DOM7r-4 (SEQ ID NO: 478), DOM7r-5 (SEQ ID NO: 479), DOM7r-7 (SEQ ID NO: 480), DOM7r-8 (SEQ ID NO: 481), DOM7h-2 (SEQ ID NO: 482), DOM7h-3 (SEQ ID NO: 483), DOM7h-4 (SEQ ID NO: 484), DOM7h-6 (SEQ ID NO: 485), DOM7h-1 (SEQ ID NO: 486), DOM7h-7 (SEQ ID NO: 487), DOM7h-22 (SEQ ID NO: 489), DOM7h-23 (SEQ ID NO: 490), DOM7h-24 (SEQ ID NO: 491), DOM7h-25 (SEQ ID NO: 492), DOM7h-26 (SEQ ID NO: 493), DOM7h-21 (SEQ ID NO: 494), DOM7h-27 (SEQ ID NO: 495), DOM7h-8 (SEQ ID NO: 496), DOM7r-13 (SEQ ID NO: 497), DOM7r-14 (SEQ ID NO: 498), DOM7r-15 (SEQ ID NO: 499), DOM7r-16 (SEQ ID NO: 500), DOM7r-17 (SEQ ID NO: 501), DOM7r-18 (SEQ ID NO: 502), DOM7r-19 (SEQ ID NO: 503), DOM7r-20 (SEQ ID NO: 504), DOM7r-21 (SEQ ID NO: 505), DOM7r-22 (SEQ ID NO: 506), DOM7r-23 (SEQ ID NO: 507), DOM7r-24 (SEQ ID NO: 508), DOM7r-25 (SEQ ID NO: 509), DOM7r-26 (SEQ ID NO: 510), DOM7r-27 (SEQ ID NO: 511), DOM7r-28 (SEQ ID NO: 512), DOM7r-29 (SEQ ID NO: 513), DOM7r-30 (SEQ ID NO: 514), DOM7r-31 (SEQ ID NO: 515), DOM7r-32 (SEQ ID NO: 516), DOM7r-33 (SEQ ID NO: 517) (the SEQ ID No's in this paragraph are those that appear in WO2007080392), dAb8, dAb 10, dAb36, dAb7r20, dAb7r21, dAb7r22, dAb7r23, dAb7r24, dAb7r25, dAb7r26, dAb7r27, dAb7r28, dAb7r29, dAb7r30, dAb7r31, dAb7r32, dAb7r33, dAb7h21, dAb7h22, dAb7h23, Ab7h24, Ab7h25, Ab7h26, dAb7h27, dAb7h30, dAb7h31, dAb2, dAb4, dAb7, dAb11, dAb12, dAb13, dAb15, dAb16, dAb17, dAb18, dAb19, dAb21, dAb22, dAb23, dAb24, dAb25, dAb26, dAb27, dAb30, dAb31, dAb33, dAb34, dAb35, dAb38, dAb41, dAb46, dAb47, dAb52, dAb53, dAb54, dAb55, dAb56, dAb7m12, dAb7m16, dAb7m26, dAb7r1, dAb7r3, dAb7r4, dAb7r5, dAb7r7, dAb7r8, dAb7r13, dAb7r14, dAb7r15, dAb7r16, dAb7r17, dAb7r18, dAb7r19, dAb7h1, dAb7h2, dAb7h6, dAb7h7, dAb7h8, dAb7h9, dAb7h10, dAb7h11, dAb7h12, dAb7h13, dAb7h14, dAb7p1, and dAb7p2.

For example, the dAb that binds human serum albumin can comprise an amino acid sequence that has at least about 90%, or at least about 95%, or at least about 96%, or at least about 97%, or at least about 98%, or at least about 99% amino acid sequence identity with DOM7h-2 (SEQ ID NO:482), DOM7h-3 (SEQ ID NO:483), DOM7h-4 (SEQ ID NO:484), DOM7h-6 (SEQ ID NO:485), DOM7h-1 (SEQ ID NO:486), DOM7h-7 (SEQ ID NO:487), DOM7h-8 (SEQ ID NO:496), DOM7r-13 (SEQ ID NO:497), DOM7r-14 (SEQ ID NO:498), DOM7h-22 (SEQ ID NO:489), DOM7h-23 (SEQ ID NO:490), DOM7h-24 (SEQ ID NO:491), DOM7h-25 (SEQ ID NO:492), DOM7h-26 (SEQ ID NO:493), DOM7h-21 (SEQ ID NO:494), DOM7h-27 (SEQ ID NO:495) (the SEQ ID No's in this paragraph are those that appear in WO2007080392), dAb8, dAb 10, dAb36, dAb7h21, dAb7h22, dAb7h23, Ab7h24, Ab7h25, Ab7h26, dAb7h27, dAb7h30, dAb7h31, dAb2, dAb4, dAb7, dAb11, dAb12, dAb13, dAb15, dAb16, dAb17, dAb18, dAb19, dAb21, dAb22, dAb23, dAb24, dAb25, dAb26, dAb27, dAb30, dAb31, dAb33, dAb34, dAb35, dAb38, dAb41, dAb46, dAb47, dAb52, dAb53, dAb54, dAb55, dAb56, dAb7h1, dAb7h2, dAb7h6, dAb7h7, dAb7h8, dAb7h9, dAb7h10, dAb7h11, dAb7h12, dAb7h13 and dAb7h14.

In certain embodiments, the dAb binds human serum albumin and comprises an amino acid sequence that has at least about 80%, or at least about 85%, or at least about 90%, or at least about 95%, or at least about 96%, or at least about 97%, or at least about 98%, or at least about 99% amino acid sequence identity with the amino acid sequence of a dAb selected from the group consisting of DOM7h-2 (SEQ ID NO:482), DOM7h-6 (SEQ ID NO:485), DOM7h-1 (SEQ ID NO:486), DOM7h-7 (SEQ ID NO:487), DOM7h-8 (SEQ ID NO:496), DOM7h-22 (SEQ ID NO:489), DOM7h-23 (SEQ ID NO:490), DOM7h-24 (SEQ ID NO:491), DOM7h-25 (SEQ ID NO:492), DOM7h-26 (SEQ ID NO:493), DOM7h-21 (SEQ ID NO:494), DOM7h-27 (SEQ ID NO:495) (the SEQ ID No's in this paragraph are those that appear in WO2007080392), dAb7h21, dAb7h22, dAb7h23, Ab7h24, Ab7h25, Ab7h26, dAb7h27, dAb7h30, dAb7h31, dAb2, dAb4, dAb7, dAb38, dAb41, dAb7h1, dAb7h2, dAb7h6, dAb7h7, dAb7h8, dAb7h9, dAb7h10, dAb7h11, dAb7h12, dAb7h13 and dAb7h14.

In more particular embodiments, the dAb is a $V_\kappa$ dAb that binds human serum albumin and has an amino acid sequence selected from the group consisting of DOM7h-2 (SEQ ID NO:482), DOM7h-6 (SEQ ID NO:485), DOM7h-1 (SEQ ID NO:486), DOM7h-7 (SEQ ID NO:487), DOM7h-8 (SEQ ID NO:496) (the SEQ ID No's in this paragraph are those that appear in WO2007080392), dAb2, dAb4, dAb7, dAb38, dAb41, dAb54, dAb7h1, dAb7h2, dAb7h6, dAb7h7, dAb7h8, dAb7h9, dAb7h10, dAb7h11, dAb7h12, dAb7h13 and dAb7h14.

In more particular embodiments, the dAb is a $V_H$ dAb that binds human serum albumin and has an amino acid sequence selected from dAb7h30 and dAb7h31.

In more particular embodiments, the dAb is dAb7h11 or dAb7h14.

In other embodiments, the dAb, ligand, agonist or antagonist binds human serum albumin and comprises one, two or three of the CDRs of any of the foregoing amino acid sequences, eg one, two or three of the CDRs of dAb7h11 or dAb7h14.

Suitable Camelid $V_{HH}$ that bind serum albumin include those disclosed in WO 2004/041862 (Ablynx N.V.) and in WO2007080392 (which $V_{HH}$ sequences and their nucleic acid counterpart are incorporated herein by reference and form part of the disclosure of the present text), such as Sequence A (SEQ ID NO:518), Sequence B (SEQ ID NO:519), Sequence C (SEQ ID NO:520), Sequence D (SEQ ID NO:521), Sequence E (SEQ ID NO:522), Sequence F (SEQ ID NO:523), Sequence G (SEQ ID NO:524), Sequence H (SEQ ID NO:525), Sequence I (SEQ ID NO:526), Sequence J (SEQ ID NO:527), Sequence K (SEQ ID NO:528), Sequence L (SEQ ID NO:529), Sequence M (SEQ ID NO:530), Sequence N (SEQ ID NO:531), Sequence 0 (SEQ ID NO:532), Sequence P (SEQ ID NO:533), Sequence Q (SEQ ID NO:534), these sequence numbers corresponding to those cited in WO2007080392 or WO 2004/041862 (Ablynx N.V.). In certain embodiments, the Camelid $V_{HH}$ binds human serum albumin and comprises an amino acid sequence that has at least about 80%, or at least about 85%, or at least about 90%, or at least about 95%, or at least about 96%, or at least about 97%, or at least about 98%, or at least about 99% amino acid sequence identity with ALB1 disclosed in WO2007080392 or any one of SEQ ID NOS:518-534, these sequence numbers corresponding to those cited in WO2007080392 or WO 2004/041862.

In some embodiments, the ligand, agonist or antagonist comprises an anti-serum albumin dAb that competes with any anti-serum albumin dAb disclosed herein for binding to serum albumin (e.g., human serum albumin).

In an alternative embodiment, the agonist, antagonist or ligand comprises a binding moiety specific for target antigen (eg, human TNFR1), wherein the moiety comprises non-immunoglobulin sequences as described in co-pending application PCT/GB2008/000453 filed 8 Feb. 2008, the disclosure of these binding moieties, their methods of production and selection (eg, from diverse libraries) and their sequences are incorporated herein by reference as part of the disclosure of the present text)

Conjugation to a Half-Life Extending Moiety (Eg, Albumin)

In one embodiment, a (one or more) half-life extending moiety (eg, albumin, transferrin and fragments and analogues thereof) is conjugated or associated with the target antigen-binding polypeptide, dAb, agonist or antagonist of the disclosure. Examples of suitable albumin, albumin fragments or albumin variants for use in a target antigen-binding format are described in WO 2005077042, which disclosure is incorporated herein by reference and forms part of the disclosure of the present text. In particular, the following albumin, albumin fragments or albumin variants can be used in the present disclosure:

SEQ ID NO:1 (as disclosed in WO 2005077042, this sequence being explicitly incorporated into the present disclosure by reference);

Albumin fragment or variant comprising or consisting of amino acids 1-387 of SEQ ID NO:1 in WO 2005077042;

Albumin, or fragment or variant thereof, comprising an amino acid sequence selected from the group consisting of: (a) amino acids 54 to 61 of SEQ ID NO:1 in WO 2005077042; (b) amino acids 76 to 89 of SEQ ID NO:1 in WO 2005077042; (c) amino acids 92 to 100 of SEQ ID NO:1 in WO 2005077042; (d) amino acids 170 to 176 of SEQ ID NO:1 in WO 2005077042; (e) amino acids 247 to 252 of SEQ ID NO:1 in WO 2005077042; (f) amino acids 266 to 277 of SEQ ID NO:1 in WO 2005077042; (g) amino acids 280 to 288 of SEQ ID NO:1 in WO 2005077042; (h) amino acids 362 to 368 of SEQ ID NO:1 in WO 2005077042; (i) amino acids 439 to 447 of SEQ ID NO:1 in WO 2005077042 (j) amino acids 462 to 475 of SEQ ID NO:1 in WO 2005077042; (k) amino acids 478 to 486 of SEQ ID NO:1 in WO 2005077042; and (l) amino acids 560 to 566 of SEQ ID NO:1 in WO 2005077042.

Figure 3:
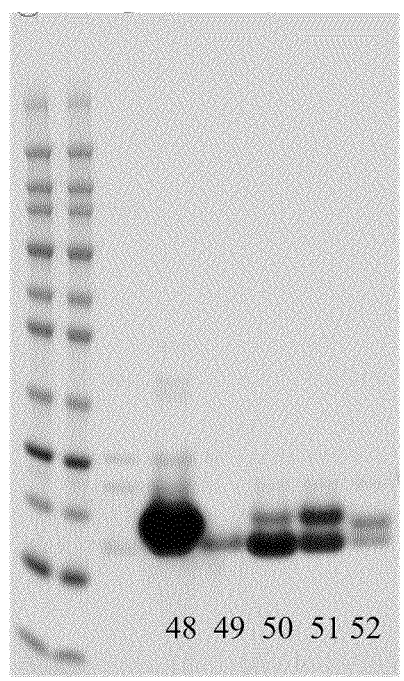
FIG. 3: Shows a gel of GLP-1-ALBUDAB™ fusion variants 6-10 (concentrated).

Further examples of suitable albumin, fragments and analogs for use in a target antigen-binding format are described in WO 03076567, which disclosure is incorporated herein by reference and which forms part of the disclosure of the present text. In particular, the following albumin, fragments or variants can be used in the present disclosure:

Human serum albumin as described in WO 03076567, eg, in FIG. 3 (this sequence information being explicitly incorporated into the present disclosure by reference);

Human serum albumin (HA) consisting of a single non-glycosylated polypeptide chain of 585 amino acids with a formula molecular weight of 66,500 (See, Meloun, et al., *FEBS Letters* 58:136 (1975); Behrens, et al., *Fed. Proc.* 34:591 (1975); Lawn, et al., *Nucleic Acids Research* 9:6102-6114 (1981); Minghetti, et al., *J. Biol. Chem.* 261:6747 (1986));

A polymorphic variant or analog or fragment of albumin as described in Weitkamp, et al., *Ann. Hum. Genet.* 37:219 (1973);

An albumin fragment or variant as described in EP 322094, eg, HA(1-373, HA(1-388), HA(1-389), HA(1-369), and HA(1-419) and fragments between 1-369 and 1-419;

An albumin fragment or variant as described in EP 399666, eg, HA(1-177) and HA(1-200) and fragments between HA(1-X), where X is any number from 178 to 199.

Where a (one or more) half-life extending moiety (eg, albumin, transferrin and fragments and analogues thereof) is used to format the target antigen-binding polypeptides, dAbs, agonists and antagonists of the disclosure, it can be conjugated using any suitable method, such as, by direct fusion to the target antigen-binding moiety (eg, anti-TNFR1 dAb), for example by using a single nucleotide construct that encodes a fusion protein, wherein the fusion protein is encoded as a single polypeptide chain with the half-life extending moiety located N- or C-terminally to the target antigen binding moiety. Alternatively, conjugation can be achieved by using a peptide linker between moeities, eg, a peptide linker as described in WO 03076567 or WO 2004003019 (these linker disclosures being incorporated by reference in the present disclosure to provide examples for use in the present disclosure). In one embodiment, conjugation can be through a helical linker such as the helical linker as described herein. It will also be appreciated that other linkers that may be useful for this purpose include those such as glycine-serine rich linkers.

In one embodiment, the linker may be a protease resistant linker. Typically, a polypeptide that enhances serum half-life in vivo is a polypeptide which occurs naturally in vivo and which resists degradation or removal by endogenous mechanisms which remove unwanted material from the organism (e.g., human). For example, a polypeptide that enhances serum half-life in vivo can be selected from proteins from the extracellular matrix, proteins found in blood, proteins found at the blood brain barrier or in neural tissue, proteins localized to the kidney, liver, lung, heart, skin or bone, stress proteins, disease-specific proteins, or proteins involved in Fc transport.

In embodiments of the disclosure described throughout this disclosure, instead of the use of an anti-target antigen "dAb" in an agonist, antagonist or ligand of the disclosure, it is contemplated that the skilled addressee can use a polypeptide or domain that comprises one or more or all 3 of the CDRs of a dAb of the disclosure that binds target antigen (e.g., CDRs grafted onto a suitable protein scaffold or skeleton, eg an affibody, an SpA scaffold, an LDL receptor class A domain or an EGF domain) The disclosure as a whole is to be construed accordingly to provide disclosure of agonists or antagonists using such domains in place of a dAb. In this respect, see WO2008096158, the disclosure of which is incorporated by reference.

In one embodiment, therefore, an agonist or antagonist of the disclosure comprises an immunoglobulin single variable domain or domain antibody (dAb) that has binding specificity for target antigen or the complementarity determining regions of such a dAb in a suitable format. The agonist or antagonist can be a polypeptide that consists of such a dAb, or consists essentially of such a dAb. The agonist or antagonist can be a polypeptide that comprises a dAb (or the CDRs of a dAb) in a suitable format, such as an antibody format (e.g., IgG-like format, scFv, Fab, Fab', F(ab')$_2$), or a dual specific ligand that comprises a dAb that binds target antigen and a second dAb that binds another target protein, antigen or epitope (e.g., serum albumin).

Polypeptides, dAbs, agonists and antagonists according to the disclosure can be formatted as a variety of suitable antibody formats that are known in the art, such as, IgG-like formats, chimeric antibodies, humanized antibodies, human antibodies, single chain antibodies, bispecific antibodies, antibody heavy chains, antibody light chains, homodimers and heterodimers of antibody heavy chains and/or light chains, antigen-binding fragments of any of the foregoing (e.g., a Fv fragment (e.g., single chain Fv (scFv), a disulfide bonded Fv), a Fab fragment, a Fab' fragment, a F(ab')$_2$ fragment), a single variable domain (e.g., $V_H$, $V_L$), a dAb, and modified versions of any of the foregoing (e.g., modified by the covalent attachment of polyalkylene glycol (e.g., polyethylene glycol, polypropylene glycol, polybutylene glycol) or other suitable polymer).

In some embodiments, the disclosure provides a ligand (eg, an anti-TNFR1 antagonist) that is an IgG-like format. Such formats have the conventional four chain structure of an IgG molecule (2 heavy chains and two light chains), in which one or more of the variable regions ($V_H$ and or $V_L$) have been replaced with a dAb of the disclosure. In one embodiment, each of the variable regions (2 $V_H$ regions and 2 $V_L$ regions) is replaced with a dAb or single variable domain, at least one of which is an anti-target antigen dAb according to the disclosure. The dAb(s) or single variable domain(s) that are included in an IgG-like format can have the same specificity or different specificities. In some embodiments, the IgG-like format is tetravalent and can have one (anti-target antigen only), two (eg, anti-target antigen and anti-SA), three or four specificities. For example, the IgG-like format can be monospecific and comprises 4 dAbs that have the same specificity; bispecific and comprises 3 dAbs that have the same specificity and another dAb that has a different specificity; bispecific and comprise two dAbs that have the same specificity and two dAbs that have a common but different specificity; trispecific and comprises first and second dAbs that have the same specificity, a third dAb with a different specificity and a fourth dAb with a different specificity from the first, second and third dAbs; or tetraspecific and comprise four dAbs that each have a different specificity. Antigen-binding fragments of IgG-like formats (e.g., Fab, F(ab')$_2$, Fab', Fv, scF$_v$) can be prepared. In one embodiment, the IgG-like formats or antigen-binding fragments thereof do not crosslink target antigen, for example, the format may be monovalent for target antigen. If complement activation and/or antibody dependent cellular cytotoxicity (ADCC) function is desired, the ligand can be an IgG1-like format. If desired, the IgG-like format can comprise a mutated constant region (variant IgG heavy chain constant region) to minimize binding to Fc receptors and/or ability to fix complement. (see e.g. Winter et al., GB 2,209,757 B; Morrison et al., WO 89/07142; Morgan et al., WO 94/29351, Dec. 22, 1994).

The ligands of the disclosure (polypeptides, dAbs, agonists and antagonists) can be formatted as a fusion protein that contains a first immunoglobulin single variable domain that is fused directly to a second immunoglobulin single variable domain. If desired such a format can further comprise a half-life extending moiety. For example, the ligand can comprise a first immunoglobulin single variable domain that is fused directly to a second immunoglobulin single variable domain that is fused directly to an immunoglobulin single variable domain that binds serum albumin.

Generally the orientation of the polypeptide domains that have a binding site with binding specificity for a target, and whether the ligand comprises a linker, is a matter of design choice. However, some orientations, with or without linkers, may provide better binding characteristics than other orientations. All orientations (e.g., dAb1-linker-dAb2; dAb2-linker-dAb1) are encompassed by the disclosure are ligands that contain an orientation that provides desired binding characteristics can be easily identified by screening.

Polypeptides and dAbs according to the disclosure, including dAb monomers, dimers and trimers, can be linked to an antibody Fc region, comprising one or both of $C_H2$ and $C_H3$ domains, and optionally a hinge region. For example, vectors encoding ligands linked as a single nucleotide sequence to an Fc region may be used to prepare such polypeptides. The disclosure moreover provides dimers, trimers and polymers of the aforementioned dAb monomers.

EXEMPLIFICATION

Example 1

Aim of the Study

The aim of the study was to obtain protease resistant variants of GLP-1 ALBUDAB™ fusions by performing phage selection on a libraries derived from a GLP-1 variant comprising DPP IV resistant GLP-1 (referred to as herein as *GLP-1) in combination with treatment of phage with various proteases (including those naturally occurring in the expression host). As described herein, an ALBUDAB™ is an immunoglobulin single variable domain that specifically binds serum albumin.

GLP-1 Receptor

The glucagon-like peptide-1 receptor (GLP-1R) belongs to the family B1 of seven transmembrane G protein-coupled receptors. Binding interactions between the receptor and its natural agonist ligand GLP-1 is initiated by ligand binding to extracellular N-terminal domain of the receptor (ECD GLP-1R) and followed by interaction with the core of transmembrane portion (Al-Sabah et al, 2003; FEBS Lett; 553(3): 342-6). It has been shown that GLP-1 binding to the isolated N-terminal domain is retained if the transmembrane core is removed, although the affinity is reduced (Lopez de Maturana et al, 2003; J. Biol. Chem.; 278(12): 10195-200). Since the use of the whole receptor is not desirable for phage selection in solution, due to the poor solution solubility of receptors with transmembrane domains in aqueous solution without solubilising detergents, the isolated extracellular domain was used for phage capture to simplify the experiment and enrich phages displaying molecules with affinity to ECD GLP-1R.

The nucleotide and amino acid sequences for the His tagged Fc monomer of ECD GLP-1R are as follows:

```
Nucleotide sequence (SEQ ID NO: 1):
ATGGCCGGCG   CCCCCGGCCC   GCTGCGCCTT   GCGCTGCTGC   TGCTCGGGAT

GGTGGGCAGG   GCCGGCCCCC   GCCCCCAGGG   TGCCACTGTG   TCCCTCTGGG

AGACGGTGCA   GAAATGGCGA   GAATACCGAC   GCCAGTGCCA   GCGCTCCCTG

ACTGAGGATC   CACCTCCTGC   CACAGACTTG   TTCTGCAACC   GGACCTTCGA

TGAATACGCC   TGCTGGCCAG   ATGGGGAGCC   AGGCTCGTTC   GTGAATGTCA

GCTGCCCCTG   GTACCTGCCC   TGGGCCAGCA   GTGTGCCGCA   GGGCCACGTG

TACCGGTTCT   GCACAGCTGA   AGGCCTCTGG   CTGCAGAAGG   ACAACTCCAG

CCTGCCCTGG   AGGGACTTGT   CGGAGTGCGA   GGAGTCCAAG   CGAGGGGAGA

GAAGCTCCCC   GGAGGAGCAG   CTCCTGTTCC   TCAAGCTTGA   GCCCAAATCG

GCCGACAAAA   CTCACACATC   ACCACCGTCA   CCAGCACCTG   AACTCCTGGG

GGGACCGTCA   GTCTTCCTCT   TCCCCCCAAA   ACCCAAGGAC   ACCCTCATGA

TCTCCCGGAC   CCCTGAGGTC   ACATGCGTGG   TGGTGGACGT   GAGCCACGAA

GACCCTGAGG   TCAAGTTCAA   CTGGTACGTG   GACGGCGTGG   AGGTGCATAA

TGCCAAGACA   AAGCCGCGGG   AGGAGCAGTA   CAACAGCACG   TACCGGGTGG

TCAGCGTCCT   CACCGTCCTG   CACCAGGACT   GGCTGAATGG   CAAGGAGTAC

AAGTGCAAGG   TCTCCAACAA   AGCCCTCCCA   GCCCCCATCG   AGAAAACCAT

CTCCAAAGCC   AAAGGGCAGC   CCCGAGAACC   ACAGGTGTAC   ACCCTGCCCC

CATCCCGGGA   TGAGCTGACC   AAGAACCAGG   TCAGCCTGAC   CTGCCTGGTC

AAAGGCTTCT   ATCCCAGCGA   CATCGCCGTG   GAGTGGGAGA   GCAATGGGCA

GCCGGAGAAC   AACTACAAGA   CCACGCCTCC   CGTGCTGGAC   TCCGACGGCT

CCTTCTTCCT   CTACAGCAAG   CTCACCGTGG   ACAAGAGCAG   GTGGCAGCAG

GGGAACGTCT   TCTCATGCTC   CGTGATGCAT   GAGGCTCTGC   ACAACCACTA

CACGCAGAAG   AGCCTCTCCC   TGTCTCCGGG   TAAACATCAC   CATCATCATC

ACTGA

Amino Acid sequence (SEQ ID NO: 2):
MAGAPGPLRL   ALLLLGMVGR   AGPRPQGATV   SLWETVQKWR   EYRRQCQRSL

TEDPPPATDL   FCNRTFDEYA   CWPDGEPGSF   VNVSCPWYLP   WASSVPQGHV

YRFCTAEGLW   LQKDNSSLPW   RDLSECEESK   RGERSSPEEQ   LLFLKLEPKS

ADKTHTSPPS   PAPELLGGPS   VFLFPPKPKD   TLMISRTPEV   TCVVVDVSHE

DPEVKFNWYV   DGVEVHNAKT   KPREEQYNST   YRVVSVLTVL   HQDWLNGKEY

KCKVSNKALP   APIEKTISKA   KGQPREPQVY   TLPPSRDELT   KNQVSLTCLV

KGFYPSDIAV   EWESNGQPEN   NYKTTPPVLD   SDGSFFLYSK   LTVDKSRWQQ

GNVFSCSVMH   EALHNHYTQK   SLSLSPGKHH   HHHH
```

The GLP-1R ECD was also expressed with an IgG Fc tag, which enabled initial purification of the protein on Protein A agarose. During phage selections, the soluble receptor could then be captured using Protein A coated beads.

Test Phage Selections

Tests were performed to verify that the extracellular domain of GLP-1 Receptor can be used for phage display library selections.

Phage Vector

A filamentous phage (fd) display vector, pDOM34 (which is a derivative of pDOM4) was used, which is based on fd vector with a myc tag and wherein a protein sequence can be cloned in between restriction sites to provide a protein-gene III fusion. (pDOM4, as described in WO 2007/085815, is a derivative of the Fd phage vector in which the gene III signal peptide sequence is replaced with the yeast glycolipid anchored surface protein (GAS) signal peptide (WO 2005/093074). It also contains a c-myc tag between the leader sequence and gene III, which puts the gene III back in frame)

Modifications of pDOM4 which lead to pDOM34 include:
1.) Knock out of the NcoI site at 7476 nt position of pDOM4
2.) Deletion of the Myc tag fused to N' terminus of cpIII
3.) Introduction of NcoI restriction site to facilitate cloning straight after the signal peptide.

The genes encoding library repertoires were cloned as NcoI/NotI fragments.

The vector was propagated in *E. coli* MACH I™ cells, isolated with use of a PLASMID MEGA PREP™ kit (Qiagen) and the supercoiled fraction was isolated by cesium chloride gradient ultracentrifugation using standard techniques (Sambrook and Maniatis 1989). Vector was cut with NcoI and NotI enzymes following by PstI to reduce self ligation rate. Followed phenol/chloroform extraction, DNA was ethanol precipitated and purified from the non required "stuffer" DNA fragment between the NcoI and NotI sites on CHROMASPIN™ TE-1000 columns (Clontech). After purification vector DNA was used to test ligations with diversified DAT-X DNA fragments.

DAT-X Libraries Construction

Eighteen repertoires were constructed based on the DAT-X parental molecule comprising DPP IV resistant GLP-1, which will be further called *GLP-1.

*GLP-1 (7-37):

```
Amino acid sequence                (SEQ ID NO: 3)
HGEGTFTSDVSSYLEGQAAKEFIAWLVKGRG Nucleotide sequence:               (SEQ ID NO: 4)
CATGGTGAAGGGACCTTTACCAGTGATGTAAGTTCTTATTTGGAAGGC

CAAGCTGCCAAGGAATTCATTGCTTGGCTGGTGAAAGGCCGAGGA
```

The DAT-X parental molecules further comprises a fusion with DOM7h-14 (a domain antibody (dAb) which binds serum albumin (ALBUDAB™)).

DOM7h-14:

```
Amino acid sequence:               (SEQ ID NO: 5)
DIQMTQSPSSLSASVGDRVTITCRASQWIGSQLSWYQQKPGKAPKLL

IMWRSSLQSGVPSRFSGSGSGTDFTLTISSLQPEDFATYYCAQGAAL

PRTFGQGTKVEIKR
```

```
Nucleotide sequence:               (SEQ ID NO: 6)
GACATCCAGATGACCCAGTCTCCATCCTCCCTGTCTGCATCTGTAGG

AGACCGTGTCACCATCACTTGCCGGGCAAGTCAGTGGATTGGGTCTC

AGTTATCTTGGTACCAGCAGAAACCAGGGAAAGCCCCTAAGCTCCTG

ATCATGTGGCGTTCCTCGTTGCAAAGTGGGGTCCCATCACGTTTCAG

TGGCAGTGGATCTGGGACAGATTTCACTCTCACCATCAGCAGTCTGC

AACCTGAAGATTTTGCTACGTACTACTGTGCTCAGGGTGCGGCGTTG

CCTAGGACGTTCGGCCAAGGGACCAAGGTGGAAATCAAACGG
```

*GLP-1 and DOM7h-14 in DAT-X parental molecule are connected by helical linker:

Helical Linker

```
Amino acid sequence:               (SEQ ID NO: 7)
KEAAAKEAAAKEAAAKELAAKEAAAKEAAAKEAAAKELAA Nucleotide sequence:               (SEQ ID NO: 8)
AAAGAAGCGGCGGCGAAAGAAGCGGCGGCGAAAGAAGCGGCGGCGAAAG

AATTGGCCGCAAAAGAAGCGGCGGCGAAAGAAGCGGCGGCGAAAGAAGC

GGCGGCGAAAGAATTGGCCGCA
```

To cover the whole sequence of the *GLP-1 (excluding sites known to be important for receptor binding (as described, for example, in Sarrauste de Menthière et al. Eur J Med. Chem. 2004 June; 39(6):473-80; Neidigh et al. Biochemistry. 2001 Nov. 6; 40(44):13188-200; Hjorth et al. J Biol. Chem. 1994 Dec. 2; 269(48):30121-4 and Gallwitz et al. Regul Pept. 1996 May 7; 63(1):17-22)), 17 repertoires were constructed using an assembly PCR protocol using PHUSION™ high fidelity Polymerase (NEB) in a 50 microlitres reaction volume. Four randomized nucleotides per library were introduced by primers in primary PCRs and then assembly was performed with biotinylated primers. Error prone PCR using MUTAZYME™ kit (Stratagene), biotinylated primers and 5-50 pg of template for a 50 µl reaction introduced random mutations within *GLP-1. Due to the short length of the *GLP-1 nucleotide sequence, error prone PCR was performed twice, to increase the mutation rate.

After digestion with NcoI and NotI, the inserts were purified from undigested products with streptavidin-coated beads. Test ligation was performed where digested products were ligated into pDOM34 at the corresponding sites.

Sequencing of the test ligation clones confirmed the expected diversification in all the libraries therefore the full scale ligation and transformation of the libraries followed. The ligation was performed in a total volume of 500 microlitres, with 1 microgram of the digested vector and insert in the ratio 1:2 with T4 DNA ligase (NEB). Each library was transformed in two shots, 10 microlitres per 100 microlitres of electrocompetent *E. coli* TB1 cells and after recovery, 100 ml of media for 1 h in 37° C. with agitation, libraries were plated on to large (22 cm) square plates containing 2×TY Tet agar. Plates were grown overnight and then scraped into 5 mls of 2×TY with 15% glycerol for stocks preparation. Libraries sizes were in the in range of $10^7$-$10^8$ transformants.

For phage library preparation a library culture was started by inoculation of 100 microlitres of glycerol stock into 200 milliliters of 2×TY media containing antibiotic such that the final density of the culture immediately following inoculation did not exceed $OD_{600}$=0.1. The libraries were cultured overnight for about 18 hours at 37° C. with agitation. Culture was pelleted by centrifugation and phage libraries were prepared by double precipitation with PEG and resuspended in PBS.

Several clones from unselected libraries were randomly chosen for sequencing to confirm successful libraries construction and the first round of panning followed after phage library preparation.

The methods of panning, glycerol stock preparation and phage amplification are as it is described below unless otherwise noted.

The extracellular domain of GLP-1 receptor was used for panning 100 microlitres of the phage libraries was incubated with 2% MARVELL™ PBS containing 100 nM GLP-1R. The incubation was carried out for 1 h at RT and then the phages were combined with pre-blocked (2% MARVELL™ PBS, 1 h, RT) protein A DYNABEADS™ (Dynal). After one hour incubation on a rotating wheel at RT the beads were washed in the KINGFISHER™ purification system (Thermo Electron Corporation) eight times with 0.1% Tween PBS (the KINGFISHER™ robot automates the washing process by using a magnetic probe to transfer the beads from wash solution to wash solution) and the specific phages were recovered by elution in 500 microlitres of 0.1M Glycine pH 2.0. After neutralization with 100 microlitres of 1M Tris-Cl pH 8.0 phage was used for infection of log phase $E.\ coli$ TG1 cells for 45 min at 37° C. Infected cells were plated on agar Tet plates which were grown overnight at 37° C. The titers of libraries, input output and library size are presented in the table below.

| Library | Library size | 1$^{st}$ selection; phage $\phi$/ml | |
|---|---|---|---|
| | | Input | output |
| 1 | $2.8 \times 10^8$ | $3.9 \times 10^{10}$ | $3.2 \times 10^7$ |
| 2 | $1.2 \times 10^8$ | $1.0 \times 10^{11}$ | $1.0 \times 10^6$ |
| 3 | $2.4 \times 10^7$ | $4.6 \times 10^{10}$ | $7.0 \times 10^5$ |
| 4 | $8.0 \times 10^7$ | $1.0 \times 10^{11}$ | $8.0 \times 10^6$ |
| 5 | $4.0 \times 10^7$ | $2.6 \times 10^9$ | $1.0 \times 10^7$ |
| 6 | $8.0 \times 10^7$ | $7.3 \times 10^{10}$ | $6.0 \times 10^6$ |
| 7 | $4 \times 10^7$ | $8.0 \times 10^9$ | $6.0 \times 10^6$ |
| 8 | $2.8 \times 10^7$ | $5.4 \times 10^9$ | $1.0 \times 10^7$ |
| 9 | $6.8 \times 10^7$ | $9.4 \times 10^9$ | $5.0 \times 10^6$ |
| 10 | $2.0 \times 10^8$ | $5.7 \times 10^8$ | $1.5 \times 10^6$ |
| 11 | $8.8 \times 10^8$ | $4.5 \times 10^9$ | $2.0 \times 10^6$ |
| 12 | $6.6 \times 10^8$ | $4.0 \times 10^9$ | $1.6 \times 10^6$ |
| 13 | $1.8 \times 10^8$ | $6.7 \times 10^{10}$ | $2.0 \times 10^5$ |
| 14 | $4.8 \times 10^7$ | $6.0 \times 10^9$ | $3.0 \times 10^5$ |
| 15 | $6.0 \times 10^7$ | $4.2 \times 10^{10}$ | $1.0 \times 10^6$ |
| 16 | $2.4 \times 10^8$ | $1.6 \times 10^{10}$ | $4.8 \times 10^5$ |
| 17 | $4.2 \times 10^8$ | $1.3 \times 10^{10}$ | $1.4 \times 10^6$ |
| 18 Error prone | $1.5 \times 10^8$ | $2.5 \times 10^9$ | $6.0 \times 10^5$ |
| Self ligation | $4.0 \times 10^5$ | | |
| DAT-X control | — | $4.0 \times 10^9$ | $1.8 \times 10^7$ |

The first selection round produced a reasonable output for all libraries.

Glycerol stocks were prepared by scraping the colonies from agar plates with 2 mls of 2×TY media containing 15% glycerol and aliquotted into cryogenic vials.

The following selections were performed on the pooled phage. The amplified phage was obtained by combined culture of the $E.\ coli$ glycerols containing outputs from the 1$^{st}$ selection from all 18 libraries. The culture was started by inoculation of 50 microlitres of each panned library glycerol stock in 1 litre of 2×TY media with antibiotic. The culture was divided into two 2 L shaker flasks, half liter into each and cultured overnight in 37° C. with agitation 250 rpm. The phage was prepared after 18-20h of culture by single precipitation with PEG and resuspension in PBS.

DAT-X Phage Display Libraries Selection with Protease

Amplified phage from 1$^{st}$ selection output was used for the further selections with constant concentration of GLP-1R, 100 nM. Additionally, before selection with trypsin, a batch of phage from the 1$^{st}$ selection output was subcloned with the R108W mutation in the ALBUDAB™ sequence. This mutation renders the Vkappa ALBUDAB™ clone more resistant for trypsin treatment when displayed on phage. This is because the arginine residue at the carboxy terminus of the dAb that links the domain antibody to the pIII protein is trypsin sensitive. Mutation at this site removes the trypsin cleavage site, and improves the targeting of protease selections to the desired region of the target peptide. Thus, two batches of phage, with or without the R108W mutation in the ALBUDAB™, were used ready in the second selection round.

Phage was treated with the proteases trypsin or chymostrypsin at different concentrations or left untreated before incubation with receptor for 1 h at room temperature. The 2$^{nd}$ selection titers ($\phi$/ml) are presented in the table below.

| $\Phi$ | Protease | input | No protease | 1 µg/ml | 10 µg/ml |
|---|---|---|---|---|---|
| DAT-X c+ | α-chymotrypsin | $2 \times 10^{10}$ | $7 \times 10^6$ | $4 \times 10^5$ | $<1 \times 10^4$ |
| R108W c+ | Trypsin | $2 \times 10^{10}$ | $6 \times 10^7$ | $3 \times 10^6$ | $4 \times 10^4$ |
| Lib 1-18 | α-chymotrypsin | $2 \times 10^{11}$ | $3 \times 10^8$ | $2 \times 10^6$ | $3 \times 10^4$ |
| R108W | Trypsin | $1 \times 10^{12}$ | $1 \times 10^8$ | $1 \times 10^7$ | $3 \times 10^6$ |

Phage outputs from each selection (0 µg/ml-10 µg/ml) was amplified by inoculation of 50 microliters of glycerol stock into 50 milliliters of 2×TY with Tet and overnight culture, 20h at 37° C. with agitation. Purified phage was used for the 3$^{rd}$ selection round, with the same incubation conditions.

The 3$^{rd}$ selection titers ($\phi$/ml) are presented in the tables below.

| | | α-chymotrypsin | | |
|---|---|---|---|---|
| $\Phi$ out 2$^{nd}$ with concentration: | input | No protease | 1 µg/ml | 10 µg/ml |
| Lib 1-18_No protease | $1 \times 10^{10}$ | $7 \times 10^8$ | $5 \times 10^4$ | ~$1 \times 10^2$ |
| Lib 1-18_1 µg/ml | $1 \times 10^{10}$ | $8 \times 10^7$ | $5 \times 10^4$ | ~$1 \times 10^3$ |
| Lib 1-18_10 µg/ml | $1 \times 10^{10}$ | $2 \times 10^8$ | $1 \times 10^6$ | $1 \times 10^4$ |
| Control DAT-X | $1 \times 10^{10}$ | $5 \times 10^6$ | $6 \times 10^4$ | ND |

| | | Trypsin | | |
|---|---|---|---|---|
| $\Phi$ out 2$^{nd}$ with concentration: | input | No protease | 1 µg/ml | 10 µg/ml |
| Lib 1-18 R108W_No protease | $2 \times 10^{11}$ | $2 \times 10^9$ | $1 \times 10^7$ | $1 \times 10^6$ |
| Lib 1-18 R108W_1 µg/ml | $1 \times 10^{11}$ | $5 \times 10^8$ | $1 \times 10^7$ | $2 \times 10^5$ |
| Lib 1-18 R108W_10 µg/ml | $1 \times 10^{11}$ | $7 \times 10^7$ | $1 \times 10^7$ | $1 \times 10^6$ |
| Control DAT-X R108W | $3 \times 10^{10}$ | $1 \times 10^7$ | $1 \times 10^7$ | $3 \times 10^4$ |

Because the diversity of clones has already decreased after the 3$^{rd}$ round, as verified by colony sequencing of a representative set of clones, a few clones from selection outputs were expressed as soluble proteins as detailed below.

DAT-X Phage Display Libraries Selection Outputs

Several *GLP-1 variants were chosen to be cloned as a fusion with ALBUDAB™ but with alternative linkers as described below, expressed, purified and assayed in the GLP-1 receptor assay. Their amino acid sequences are set out as sequences 1-10 (see FIG. 1). One *GLP-1 sequence variant (7) was abundantly present in outputs from selections with both chymotrypsin and trypsin treatment and as a fusion is called DMS7149, two were present in outputs when chymotrypsin was used (DMS7150 (8) and 51(9)), one was observed in the outputs where only natural proteases were acting in the cells during the phage expression and secretion and no pretreatment with trypsin or chymotrypsin was used (DMS7148 (6)) and one cloned to create a knock out of trypsin cleavage sites (DMS7152 (10)).

Proteins with the amino acid sequences 1-4 (see FIG. 1) were assayed and showed low potency relative to GLP-1 and control DAT-X variant. Edman sequencing suggested that the proteins were wrongly processed.

Cloning was performed by introducing mutations into DAT-Y clone which comprises *GLP-1 linked to DOM7h$^{-14}$ by an alternative linker having the amino acid sequence: PSS (SEQ ID NO: 9) and nucleotide sequence: CCAAGCTCG (SEQ ID NO: 10).

Chosen mutations were introduced to the *GLP-1 sequence by primers in primary PCR and in the assembly PCR the NcoI and BamHI digestion sites were introduced on 5' and 3' terminus respectively of the fusion sequence.

Assembly PCR was digested with NcoI and BamHI restriction endonucleases.

Expression vector pDOM35 was prepared for cloning.

Vector pDOM35 is a derivative of pET12a with modifications:

The last three residues of OmpT signal peptide are changed from SFA to AWA which improves processing at the correct site by the signal peptidase of *E. coli*.

The NcoI site was introduced to facilitate cloning straight after the signal peptide.

A 'stuffer' is present between NcoI and BamHI site pDOM35 was digested with NcoI and BamHI and cut assembly PCRs were ligated into the vector with use of QUICK LIGATION KIT™ (NEB). 2 microlitres of ligation was used for transformation of MACH I™ cells and after recovery cells were plated on agar plates containing carbenicilin and grown overnight. Colonies were sequenced and these containing correct sequence were used for plasmid propagation and its isolation (PLASMID MINI PREP™ kit, Qiagen). BL21 (DE3) cells were transformed with plasmid DNA and resulting colonies were used for inoculation of expression culture.

Expression was performed by inoculation of a 50 milliliter culture of 2×TY media supplemented with OVERNIGHT EXPRESS™ autoinduction solutions (1 milliliter of Solution 1 (Cat. No. 71298), 2.5 milliliters of Solution 2 (Cat. No. 71299), 50 microliters of Solution 3 (Cat. No 71304), Novagen) and 100 microgram per milliliter of carbenicillin. Culture was carried overnight at 37° C., and then the culture supernatant was clarified by centrifugation at 3700×g for 45 minutes. The expressed protein was then purified from the clarified supernatant using PROTEIN L STREAMLINE™ (GE Healthcare, Cat. No. 28-4058-03, protein L coupled), and eluted from the Protein L using 0.1M glycine pH 2.0, then neutralized using 0.2 volumes of 1M Tris pH 8.0.

The *GLP-1 variant portion from DMS7148 was also cloned as fusion DMS7161 (Sequence 11) with ALBUDAB™ of higher affinity, DOM7h$^{-14}$-10, and connected by the alternative, PSS linker, into the pDOM35 as it was described earlier.

DOM7h-14-10

Amino Acid sequence (SEQ ID NO: 22):
DIQMTQSPSSLSASVGDRVTITCRASQWIGSQLSWYQQKPGKAPKLLIM

WRSSLQSGVPSRFSGSGSGTDFTLTISSLQPEDFATYYCAQGLRHPKTF

GQGTKVEIKR

Nucleotide sequence (SEQ ID NO: 23):
GACATCCAGATGACCCAGTCTCCATCCTCCCTGTCTGCATCTGTAGGAG

ACCGTGTCACCATCACTTGCCGGGCAAGTCAGTGGATTGGGTCTCAGTT

ATCTTGGTACCAGCAGAAACCAGGGAAAGCCCCTAAGCTCCTGATCATG

TGGCGTTCCTCGTTGCAAAGTGGGGTCCCATCACGTTTCAGTGGCAGTG

GATCTGGGACAGATTTCACTCTCACCATCAGCAGTCTGCAACCTGAAGA

TTTTGCTACGTACTACTGTGCTCAGGGTTTGAGGCATCCTAAGACGTTC

GGCCAAGGGACCAAGGTGGAAATCAAACGG

After the plasmid DNA pDOM35 comprising sequence of DMS7161 was transformed into BL21(DE3), glycerol stock was prepared from grown colonies, by scraping colonies into minimal media with glucose and addition of glycerol, final concentration of approximately 15%. Expression of DMS7161 was started by inoculation of the glycerol into 50 milliliters of minimal media (DMS7161 A) supplemented in Yeast Extract for final concentration 10g/liter (DMS7161 B) so as to obtain the starting culture density of OD600=0.024. The culture was grown to OD600 of approximately 1.4 at 30° C., then induced by the addition of 0.1 mM isopropyl-beta-d-thiogalactoside. Culture was continued for a further 24h at 23° C. and then the culture supernatant was clarified by centrifugation at 3700×g for 45 minutes. The expressed protein was then purified from the clarified supernatant using protein L, and eluted from the Protein L (GE Healthcare, Cat. No. 28-4058-03, protein L coupled) using 0.1M glycine pH2.0, then neutralized using 0.2 volumes of 1M Tris pH8.0.

Quality Control of DMS7148-52

Figure 4:
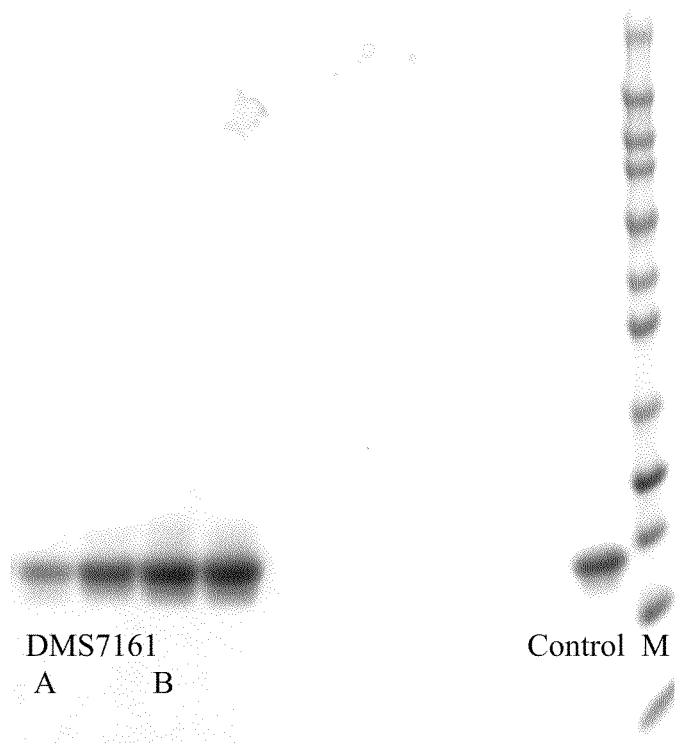
FIG. 4: Shows a gel of GLP-1-ALBUDAB™ fusion variant 11.
Figure 5:
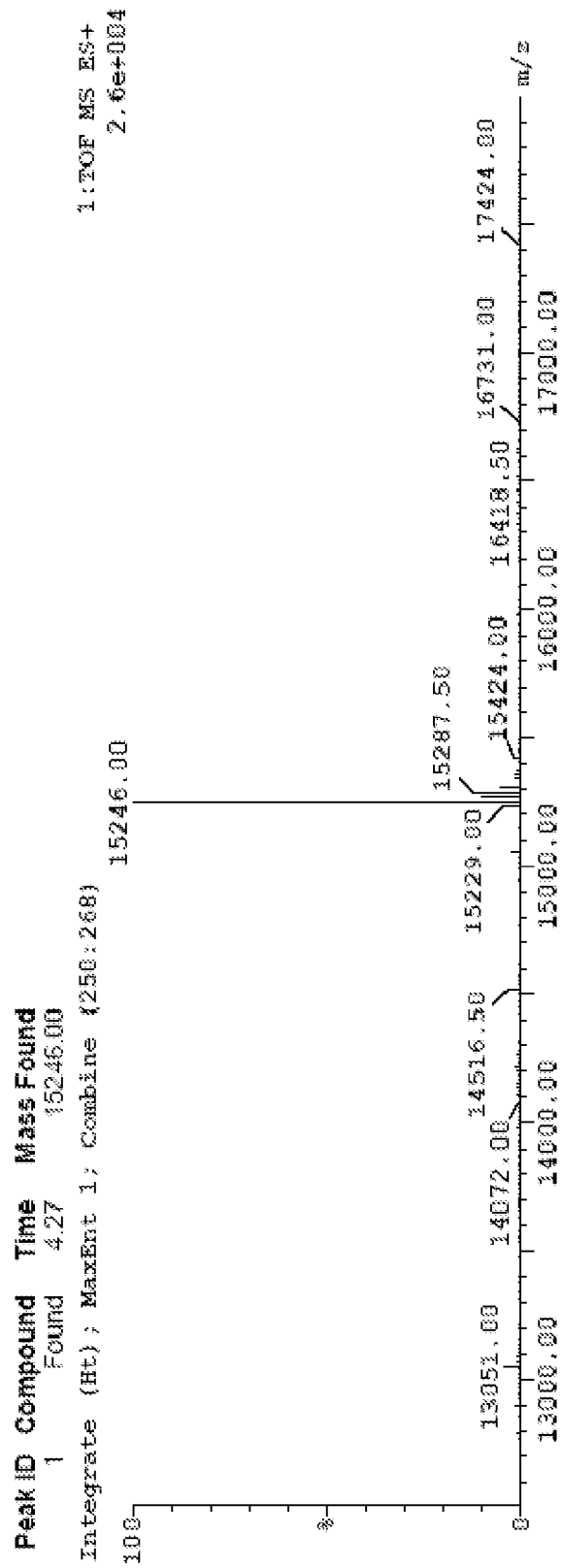
FIG. 5: Shows MS results of GLP-1-ALBUDAB™ fusion variants 6-11.
Figure 5:
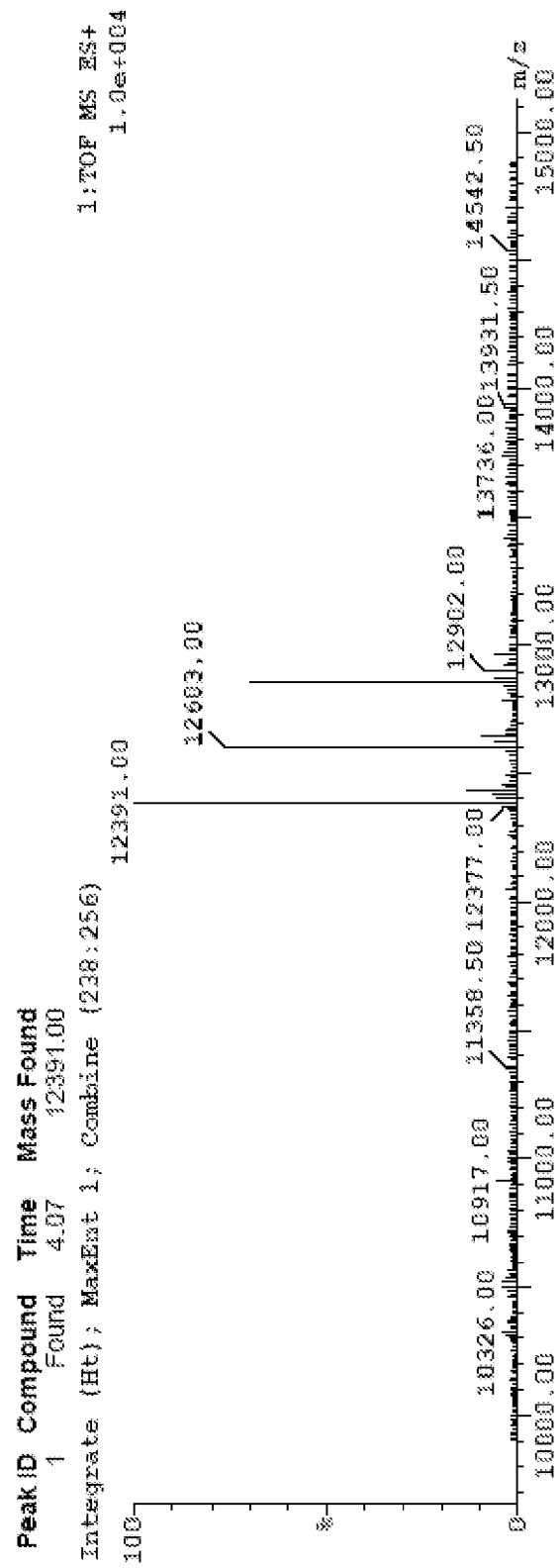
Figure 5:
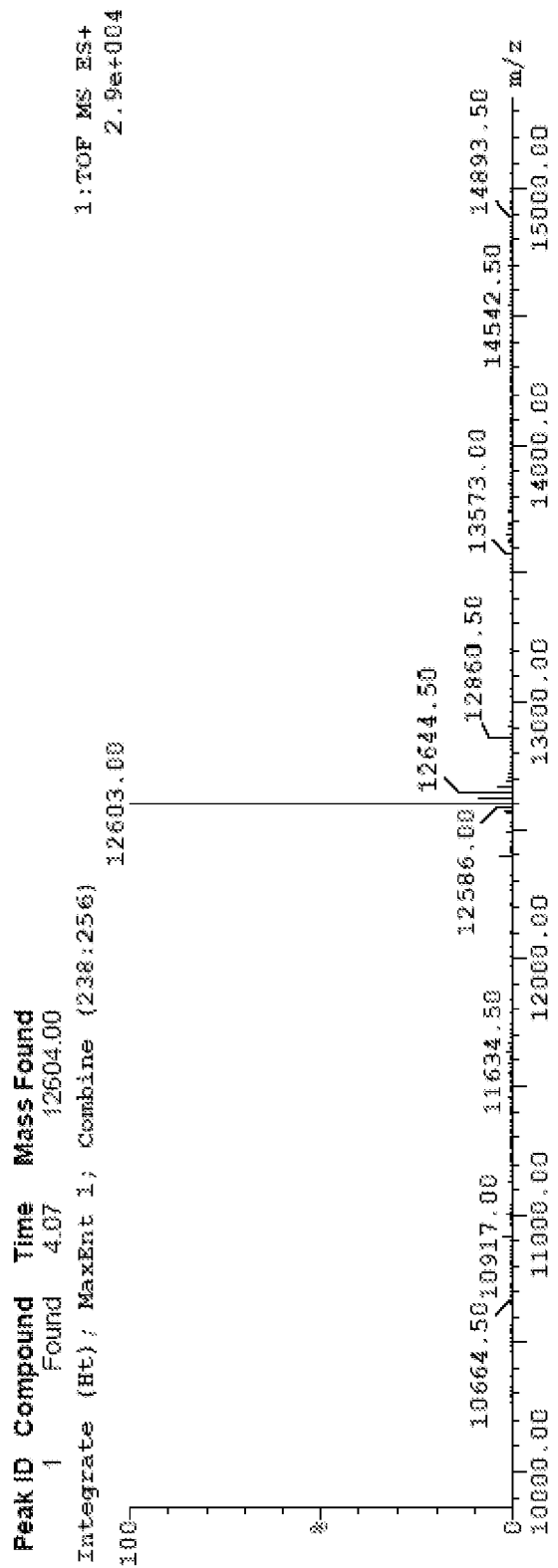
Figure 5:
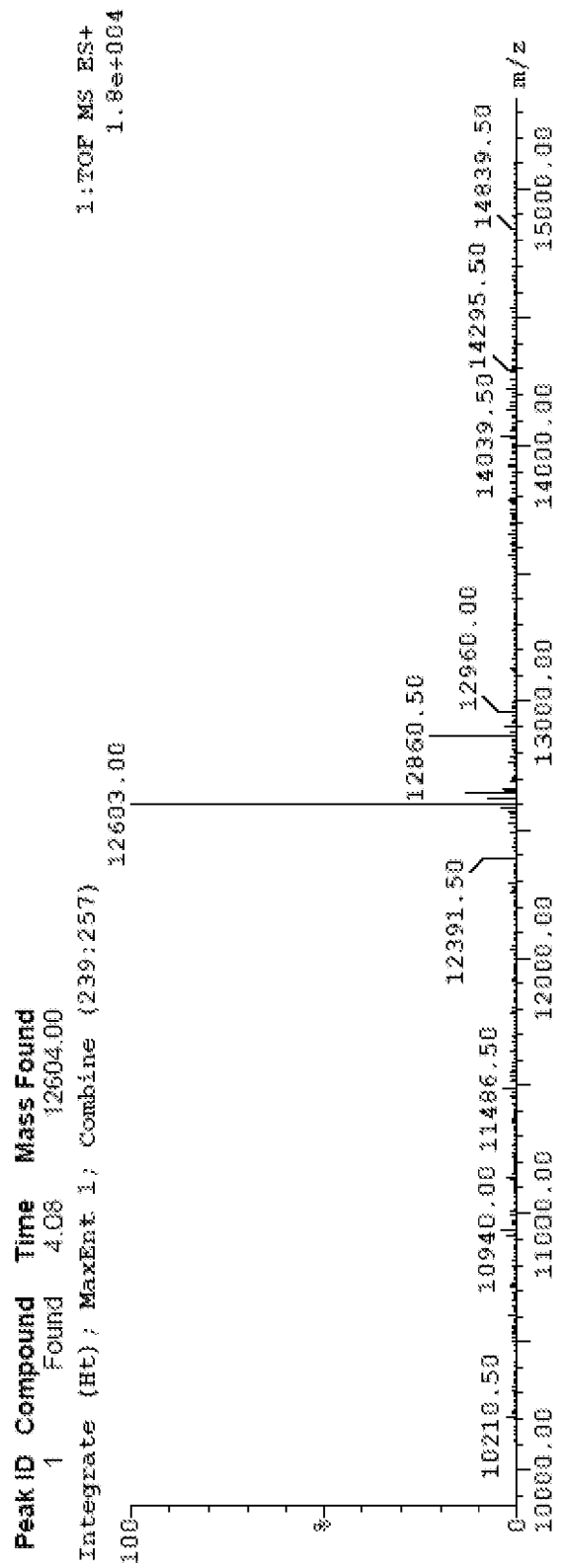
Figure 5:
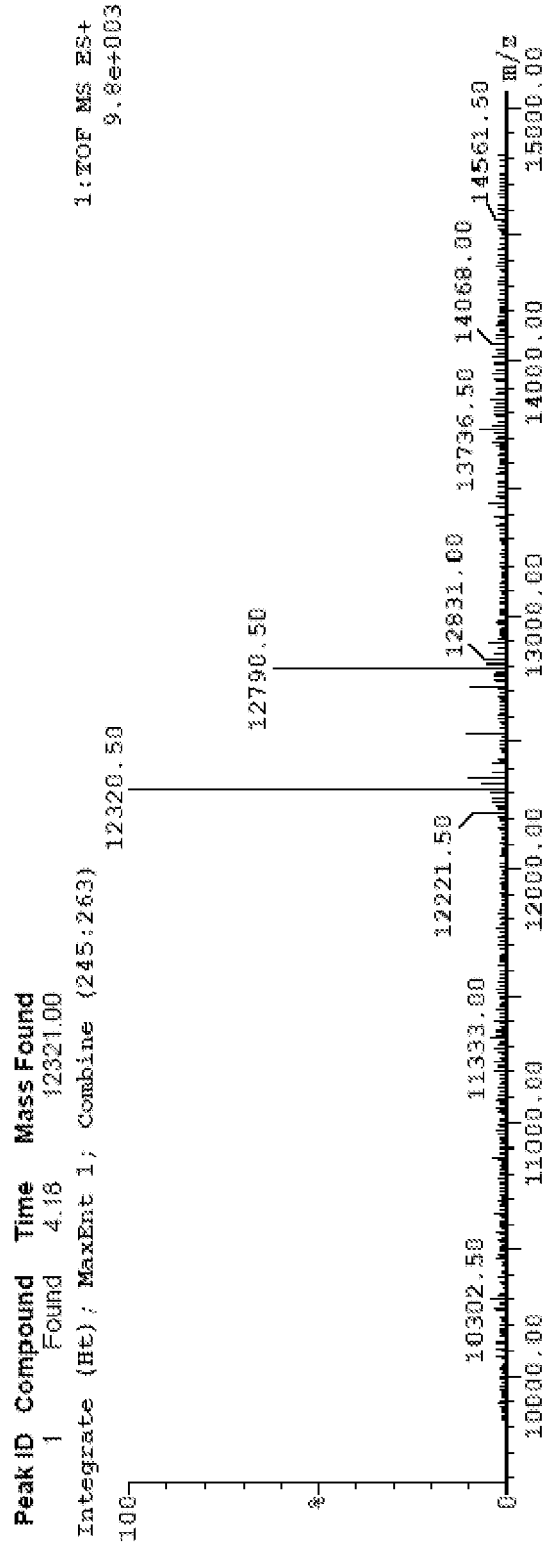
Figure 5:
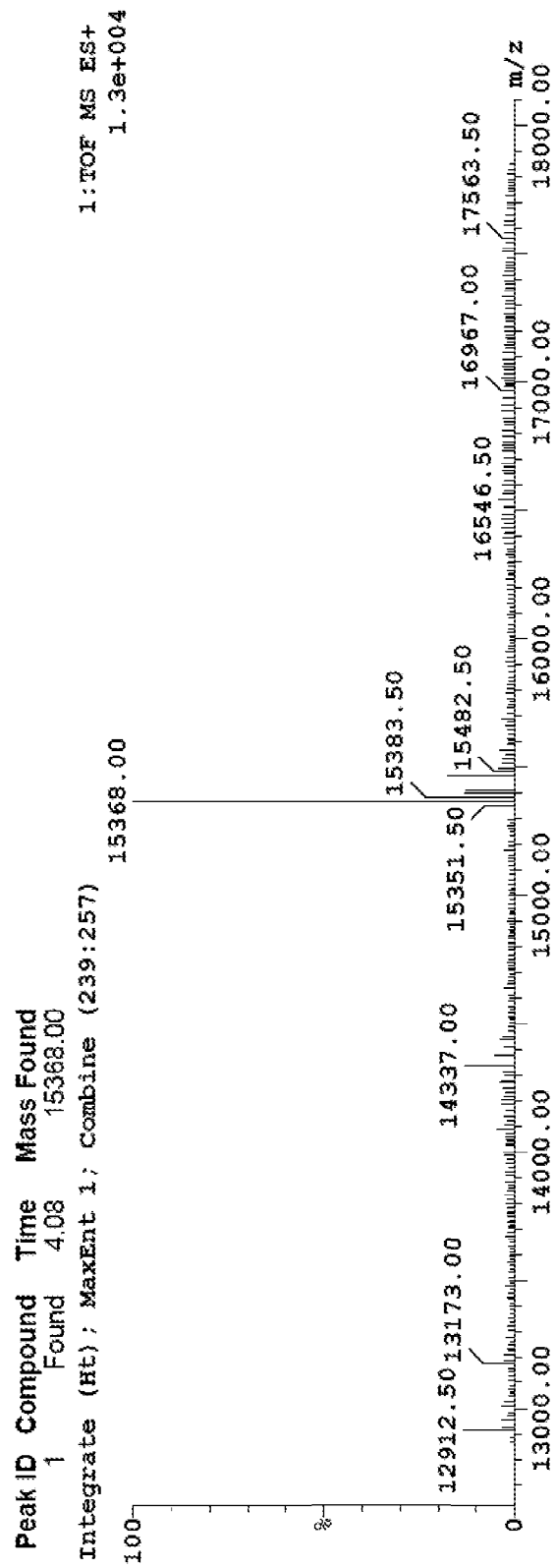

Proteins DMS7148-52 were expressed and visualized on non reducing SDS-PAGE, DMS7148 and DMS7161 clones were well expressed in *E. coli* with the majority of material migrating at the expected size (FIGS. 2, 3 and 4). Mass Spectrometry (FIG. 5 *a*)) and Edman sequencing analyses confirmed the integrity of the sequence. All the other proteins were degraded at the amino and carboxyl site of 25-Tryptophan (products 24-142 and 26-142 respectively) where DMS7148 contains W25-D mutation and aspartic acid did not create a cleavage site for the natural protease acting in *E. coli* cells (FIGS. 5 *a*) to *f*)). The degradation product 28-142 was also observed in the remaining clones.

Protein DMS7148 was assayed for activity in a GLP-1 receptor binding assay according to the following protocol:

Background: GLP-1R is a 7™ G-protein coupled receptor which is expressed on CHO cells. Activation of the receptor by GLP-1 or such analogues, leads to the conversion of ATP to cAMP by adenylate cyclase which is coupled to the receptor. CHO cells are stably transfected with the 6CRE/luc reporter gene. On production of cAMP following GLP-1 activation of the receptor, the promoter gene (containing 6 copies of cAMP response element—6CRE) drives the expression of the luciferase reporter gene. This then catalyses a reaction with luciferin to produce light which can be measured on a luminometer.

Protocol: CHO 6CRE GLP1R cells (CHO K1 cells stably transfected with 6 cAMP response element driving a luciferase reporter gene and also with human GLP-1 receptor) were seeded at 2×10$^5$ cells/mL in suspension media.

Suspension culture was maintained for forty-eight hours. Cells were then diluted into 15 mM HEPES, 2 mM L glutamine ($2.5 \times 10^5$ cells/ml) and dispensed into 384-well plates containing 10 ul/well of the compound to be assayed. After the addition of assay controls, plates were returned to the incubator for 3 h at 37° C. and 5% $CO_2$. After the incubation, STEADY GLO™ luciferase substrate (Promega) was added to the wells as described in the kit and the plates sealed with self-adhesive plate seals (Weber Marking Systems Inc. Cat. No. 607780). Plates were placed in the reader (Packard TopCount) and pre-incubated for 5 minutes prior to reading fluorescence and plotting of results. Compound was assayed at a range of concentrations response curve to be fitted from which pC50s were calculated.

Figure 6:
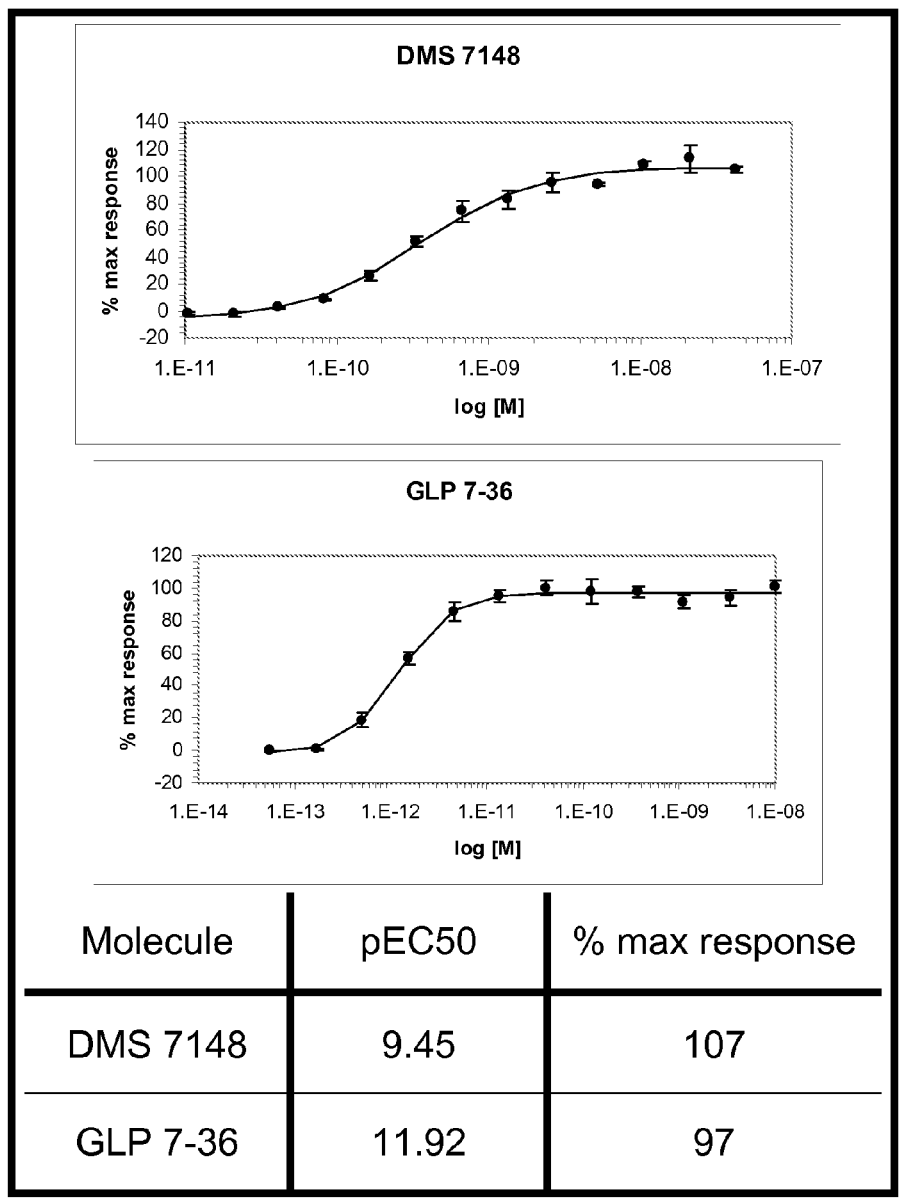
FIG. 6: Shows the results of an assay of GLP-1-AL-BUDAB™ fusion variant 6.

Protein DMS7148 was found to be active, however less active than GLP-1 peptide (FIG. 6 and summarized below).

| Molecule | pEC50 | % max response |
|---|---|---|
| DMS 7148 | 9.45 | 107 |
| GLP 7-36 | 11.92 | 97 |

DMS7161 was assayed for activity in a GLP-1 assay according to the following protocol:
Method:
CHO 6CRE GLP1R cells were rapidly defrosted by half immersing the vial(s) in a 37° C. water bath, and the contents of the vial(s) transferred to a 50 ml falcon tube and 10 ml RPMI (phenol red free) assay media (Sigma, cat #R7509)+2 mM L-glutamine (Gibco, cat #25030)+15 mM HEPES (Sigma, cat #H0887) added per vial. After counting and centrifugation at 1200 rpm for 5 minutes cells were resuspended in the appropriate volume of RPMI assay media to give $1 \times 10^6$ cells per ml and 50 µl dispensed into each well of a white 96 well flat bottom tissue culture plate (COSTAR™ 96 well tissue culture plate, white sterile, cat #3917). Cells were incubated overnight at 37 C/5% $CO_2$. Next day cell were removed from incubator and 50 µl of previously prepared control/sample was added to wells and plate was returned to incubator for 3 hours 37° C. and 5% $CO_2$.
Preparing GLP-1(7-36) Control (Sigma, cat #G814)
In a V-bottom 96 well plate add 2 µl of 1 mg/ml GLP-1(7-36) to 18 µl RPMI assay media to give a 30 µM solution. Add 2 µl of the 30 µM solution to 298 µl RPMI assay media to give a 200 nM solution (for a final concentration in the assay of 100 nM). Serial dilute the control 1:10 down the plate (15 µl control+135 µl RPMI assay media) to generate an 8 point curve.
Preparing Exendin-4 Control (Sigma, cat #E7144)
In a V-bottom 96 well plate add 2 µl of 1 mg/ml) Exendin-4 to 198 µl RPMI assay media to give a 2.39 µM solution. Add 2 µl of the 2.39 µM solution to 237 µl RPMI assay media to give a 20 nM solution (for a final concentration in the assay of 10 nM). Serial dilute the control 1:10 down the plate (15 µl control+135 µl RPMI assay media) to generate an 8 point curve.
Preparing Unknown Samples
Use the same guidelines for preparation of the controls for the preparation of the unknown samples. Make the top concentration at twice the final assay concentration required and dilute 1:10 down the plate.
Preparing the Luciferase (Promega, cat #E2620)
Remove the required number of BRIGHT-GLO™ luciferase aliquots from the freezer and allow defrosting at RT in the dark. One 5 ml vial is sufficient for one assay plate After the incubation time 50 µl of BRIGHT-GLO™ luciferase reagent was added to all wells and the plate was incubated at room temperature for 3 mins to allow cell lysis to occur. The luminescence (counts per second) was read using the M5E™ microplate reader, reading each well for 0.1 sec. CPS of the background wells containing cells only, was subtracted from all other wells. The control wells (GLP-1(7-36) or Exendin-4) should exhibit maximum stimulation at the highest concentrations. Concentration effect curves of the unknown samples are fitted from which the EC50 is calculated with use of GRAPHPAD PRISM™ or EXCELFIT™ software.

Figure 7:
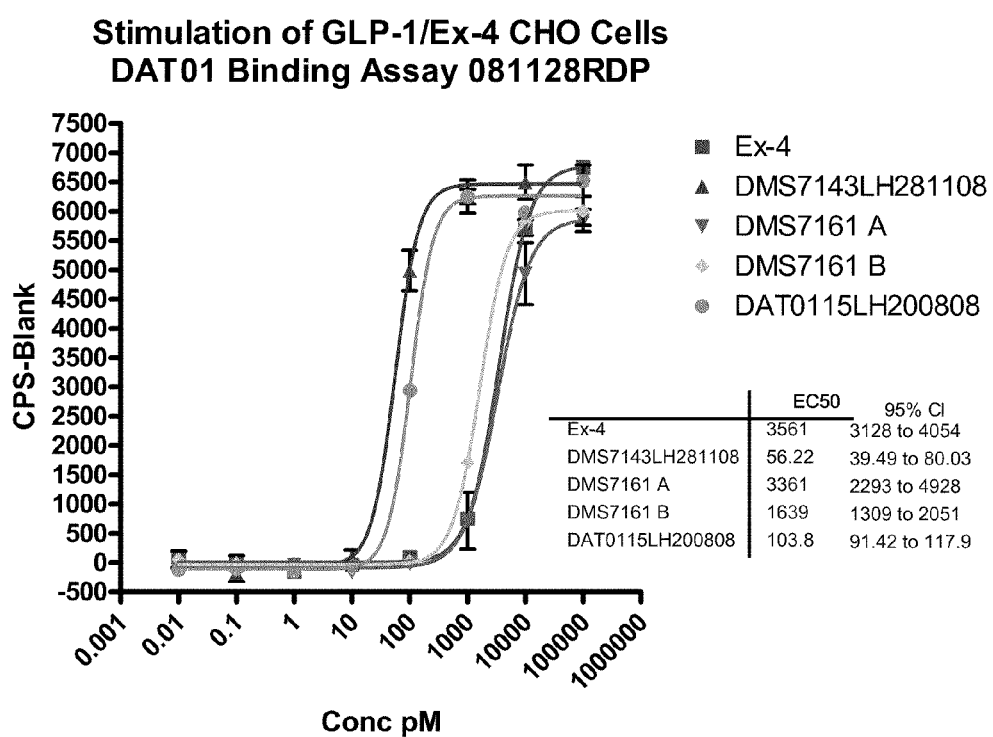
FIG. 7: Shows the results of an assay of GLP-1-AL-BUDAB™ fusion variant 11.

DMS7161 is potent with EC50 between 1.6 and 3.4 nM as shown in FIG. 7 and summarized below.

| | EC50 (M) | pEC50 |
|---|---|---|
| ex-4 | 3.6E−09 | 8.45 |
| DMS7161 A | 3.4E−09 | 8.47 |
| DMS7161 B | 1.6E−09 | 8.79 |

DMS7161 was found to be as active as DMS7148

SUMMARY

Phage selection of diversified peptide fusion which was naturally very sensitive to proteases and degrades during expression in *E. coli* allowed us to identify the *GLP-1 variant-fusion which is resistant to natural bacterial proteases and the same is expressible in *E. coli*. The protease sites which were knocked out in this clone are similar to these recognized by trypsin and chymotrypsin, however this sequence was not present in outputs from selections with additional trypsin or chymotrypsin treatment.

| Sequence | SEQ ID NO: |
|---|---|
| His tagged Fc monomer of ECD GLP1R Nucleotide sequence | 1 |
| His tagged Fc monomer of ECD GLP1R Amino acid sequence | 2 |
| *GLP1 (737) Amino acid sequence | 3 |
| *GLP1 (737) Nucleotide sequence | 4 |
| DOM7h14 Amino acid sequence: | 5 |
| DOM7h14 Nucleotide sequence: | 6 |
| Helical linker Amino acid sequence: | 7 |
| Helical linker Nucleotide sequence: | 8 |
| PSS | 9 |
| PSS nucleotide sequence: | 10 |
| DMS7190 | 11 |
| DMS7191 | 12 |
| DMS7192 | 13 |
| DMS7193 | 14 |
| DMS7194 | 15 |
| DMS7148 | 16 |
| DMS7149 | 17 |
| DMS7150 | 18 |
| DMS7151 | 19 |
| DMS7152 | 20 |
| DMS7161 | 21 |
| DOM7h1410 Amino Acid sequence | 22 |
| DOM7h1410 Nucleotide sequence | 23 |

The material in the ASCII text file named "DB00064SeqList30Oct2013.TXT" created on Oct. 30, 2013 and having a size of 26,603 bytes is incorporated herein by reference in its entirety.

The invention claimed is:

1. An immunoglobulin single variable domain comprising a CDR1 amino acid sequence as shown at residues 24 to 34 of SEQ ID NO: 22; a CDR2 amino acid sequence as shown at residues 49 to 56 of SEQ ID NO: 22; and a CDR3 amino acid sequence as shown at residues 89 to 97 of SEQ ID NO: 22.

2. An isolated polypeptide comprising the amino acid sequence shown in SEQ ID NO: 22.

3. An isolated polypeptide comprising the amino acid sequence shown in SEQ ID NO: 21.

* * * * *

SEQUENCE LISTING

<160> NUMBER OF SEQ ID NOS: 24

<210> SEQ ID NO 1
<211> LENGTH: 1155
<212> TYPE: DNA
<213> ORGANISM: Artificial Sequence
<220> FEATURE:
<223> OTHER INFORMATION: Source: Nucleic acid sequence made using
      molecular biology techniques and encoding a His tagged Fc
      monomer of ECD GLP1R.

<400> SEQUENCE: 1

```
atggccggcg ccccggccc gctgcgcctt gcgctgctgc tgctcgggat ggtgggcagg      60
gccggccccc gccccagggg tgccactgtg tccctctggg agacggtgca gaaatggcga    120
gaataccgac gccagtgcca gcgctccctg actgaggatc cacctcctgc cacagacttg    180
ttctgcaacc ggaccttcga tgaatacgcc tgctggcccag atggggagcc aggctcgttc    240
gtgaatgtca gctgcccctg gtacctgccc tgggccagca gtgtgccgca gggccacgtg    300
taccggttct gcacagctga aggcctctgg ctgcagaagg acaactccag cctgccctgg    360
agggacttgt cggagtgcga ggagtccaag cgaggggaga aagctcccc ggaggagcag     420 ctcctgttcc tcaagcttga gcccaaatcg gccgacaaaa ctcacacatc accaccgtca    480
ccagcacctg aactcctggg gggaccgtca gtcttcctct tccccccaaa acccaaggac    540
accctcatga tctcccggac ccctgaggtc acatgcgtgg tggtggacgt gagccacgaa    600
gaccctgagg tcaagttcaa ctggtacgtg gacggcgtgg aggtgcataa tgccaagaca    660
aagccgcggg aggagcagta caacagcacg taccgggtgg tcagcgtcct caccgtcctg    720
caccaggact ggctgaatgg caaggagtac aagtgcaagg tctccaacaa agccctccca    780
gcccccatcg agaaaaccat ctccaaagcc aaagggcagc cccgagaacc acaggtgtac    840
accctgcccc catcccggga tgagctgacc aagaaccagg tcagcctgac ctgcctggtc    900
aaaggcttct atcccagcga catcgccgtg gagtgggaga gcaatgggca gccggagaac    960
aactacaaga ccacgcctcc cgtgctggac tccgacggct ccttcttcct ctacagcaag   1020
ctcaccgtgg acaagagcag gtggcagcag gggaacgtct tctcatgctc cgtgatgcat   1080
gaggctctgc acaaccacta cacgcagaag agcctctccc tgtctccggg taaacatcac   1140
catcatcatc actga                                                     1155
```

<210> SEQ ID NO 2
<211> LENGTH: 384
<212> TYPE: PRT
<213> ORGANISM: Artificial Sequence
<220> FEATURE:
<223> OTHER INFORMATION: Source: Amino acid sequence of His tagged Fc
      monomer of ECD GLP1R made using molecular biology
      techniques.

<400> SEQUENCE: 2

```
Met Ala Gly Ala Pro Gly Pro Leu Arg Leu Ala Leu Leu Leu Leu Gly
 1               5                  10                  15

Met Val Gly Arg Ala Gly Pro Arg Pro Gln Gly Ala Thr Val Ser Leu
                20                  25                  30

Trp Glu Thr Val Gln Lys Trp Arg Glu Tyr Arg Arg Gln Cys Gln Arg
            35                  40                  45

Ser Leu Thr Glu Asp Pro Pro Ala Thr Asp Leu Phe Cys Asn Arg
        50                  55                  60
```

```
Thr Phe Asp Glu Tyr Ala Cys Trp Pro Asp Gly Glu Pro Gly Ser Phe
 65                  70                  75                  80

Val Asn Val Ser Cys Pro Trp Tyr Leu Pro Trp Ala Ser Ser Val Pro
                 85                  90                  95

Gln Gly His Val Tyr Arg Phe Cys Thr Ala Glu Gly Leu Trp Leu Gln
            100                 105                 110

Lys Asp Asn Ser Ser Leu Pro Trp Arg Asp Leu Ser Glu Cys Glu Glu
        115                 120                 125

Ser Lys Arg Gly Glu Arg Ser Ser Pro Glu Glu Gln Leu Leu Phe Leu
130                 135                 140

Lys Leu Glu Pro Lys Ser Ala Asp Lys Thr His Thr Ser Pro Pro Ser
145                 150                 155                 160

Pro Ala Pro Glu Leu Leu Gly Gly Pro Ser Val Phe Leu Phe Pro Pro
                165                 170                 175

Lys Pro Lys Asp Thr Leu Met Ile Ser Arg Thr Pro Glu Val Thr Cys
            180                 185                 190

Val Val Val Asp Val Ser His Glu Asp Pro Glu Val Lys Phe Asn Trp
        195                 200                 205

Tyr Val Asp Gly Val Glu Val His Asn Ala Lys Thr Lys Pro Arg Glu
210                 215                 220

Glu Gln Tyr Asn Ser Thr Tyr Arg Val Val Ser Val Leu Thr Val Leu
225                 230                 235                 240

His Gln Asp Trp Leu Asn Gly Lys Glu Tyr Lys Cys Lys Val Ser Asn
                245                 250                 255

Lys Ala Leu Pro Ala Pro Ile Glu Lys Thr Ile Ser Lys Ala Lys Gly
            260                 265                 270

Gln Pro Arg Glu Pro Gln Val Tyr Thr Leu Pro Pro Ser Arg Asp Glu
        275                 280                 285

Leu Thr Lys Asn Gln Val Ser Leu Thr Cys Leu Val Lys Gly Phe Tyr
290                 295                 300

Pro Ser Asp Ile Ala Val Glu Trp Glu Ser Asn Gly Gln Pro Glu Asn
305                 310                 315                 320

Asn Tyr Lys Thr Thr Pro Pro Val Leu Asp Ser Asp Gly Ser Phe Phe
                325                 330                 335

Leu Tyr Ser Lys Leu Thr Val Asp Lys Ser Arg Trp Gln Gln Gly Asn
            340                 345                 350

Val Phe Ser Cys Ser Val Met His Glu Ala Leu His Asn His Tyr Thr
        355                 360                 365

Gln Lys Ser Leu Ser Leu Ser Pro Gly Lys His His His His His His
370                 375                 380

<210> SEQ ID NO 3
<211> LENGTH: 31
<212> TYPE: PRT
<213> ORGANISM: Artificial Sequence
<220> FEATURE:
<223> OTHER INFORMATION: Source:  Amino acid sequence of *GLP1 (737)
      made using molecular biology techniques.

<400> SEQUENCE: 3

His Gly Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Gly
             20                  25                  30

<210> SEQ ID NO 4
<211> LENGTH: 93
```

```
<212> TYPE: DNA
<213> ORGANISM: Artificial Sequence
<220> FEATURE:
<223> OTHER INFORMATION: Source:  Nucleic acid sequence made using
      molecular biology techniques and encoding *GLP1
      (737).

<400> SEQUENCE: 4
catggtgaag ggacctttac cagtgatgta agttcttatt tggaaggcca agctgccaag    60
gaattcattg cttggctggt gaaaggccga gga                                93

<210> SEQ ID NO 5
<211> LENGTH: 108
<212> TYPE: PRT
<213> ORGANISM: Artificial Sequence
<220> FEATURE:
<223> OTHER INFORMATION: Source:  Amino acid sequence of DOM7h14 domain
      antibody made using molecular biology techniques.

<400> SEQUENCE: 5

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Trp Ile Gly Ser Gln
                 20                  25                  30

Leu Ser Trp Tyr Gln Gln Lys Pro Gly Lys Ala Pro Lys Leu Leu Ile
             35                  40                  45

Met Trp Arg Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Ala Gln Gly Ala Ala Leu Pro Arg
                 85                  90                  95

Thr Phe Gly Gln Gly Thr Lys Val Glu Ile Lys Arg
            100                 105

<210> SEQ ID NO 6
<211> LENGTH: 324
<212> TYPE: DNA
<213> ORGANISM: Artificial Sequence
<220> FEATURE:
<223> OTHER INFORMATION: Source:  Nucleic acid sequence made using
      molecular biology techniques and encoding the
      Amino acid sequence of the DOM7h14 domain
      antibody.

<400> SEQUENCE: 6
gacatccaga tgacccagtc tccatcctcc ctgtctgcat ctgtaggaga ccgtgtcacc    60
atcacttgcc gggcaagtca gtggattggg tctcagttat cttggtacca gcagaaacca   120
gggaaagccc ctaagctcct gatcatgtgg cgttcctcgt tgcaaagtgg ggtcccatca   180
cgtttcagtg gcagtggatc tgggacagat ttcactctca ccatcagcag tctgcaacct   240
gaagattttg ctacgtacta ctgtgctcag ggtgcggcgt tgcctaggac gttcggccaa   300
gggaccaagg tggaaatcaa acgg                                         324

<210> SEQ ID NO 7
<211> LENGTH: 40
<212> TYPE: PRT
<213> ORGANISM: Artificial Sequence
<220> FEATURE:
<223> OTHER INFORMATION: Source:  Amino acid sequence of a Helical
      linker made using molecular biology techniques.

<400> SEQUENCE: 7
```

```
Lys Glu Ala Ala Ala Lys Glu Ala Ala Ala Lys Glu Ala Ala Lys
 1               5                  10                  15

Glu Leu Ala Ala Lys Glu Ala Ala Lys Glu Ala Ala Lys Glu
                20                  25                  30

Ala Ala Ala Lys Glu Leu Ala Ala
             35                  40
```

<210> SEQ ID NO 8
<211> LENGTH: 120
<212> TYPE: DNA
<213> ORGANISM: Artificial Sequence
<220> FEATURE:
<223> OTHER INFORMATION: Source: Nucleic acid sequence made using
      molecular biology techniques and encoding a
      Helical linker.

<400> SEQUENCE: 8
aaagaagcgg cggcgaaaga agcggcggcg aaagaagcgg cggcgaaaga attggccgca    60
aaagaagcgg cggcgaaaga agcggcggcg aaagaagcgg cggcgaaaga attggccgca   120

<210> SEQ ID NO 9
<211> LENGTH: 3
<212> TYPE: PRT
<213> ORGANISM: Artificial Sequence
<220> FEATURE:
<223> OTHER INFORMATION: Source: Amino acid sequence of PSS made using
      molecular biology techniques.

<400> SEQUENCE: 9

Pro Ser Ser
 1

<210> SEQ ID NO 10
<211> LENGTH: 9
<212> TYPE: DNA
<213> ORGANISM: Artificial Sequence
<220> FEATURE:
<223> OTHER INFORMATION: Source: Nucleic acid sequence made using
      molecular biology techniques and encoding PSS.

<400> SEQUENCE: 10 ccaagctcg                                                             9

<210> SEQ ID NO 11
<211> LENGTH: 149
<212> TYPE: PRT
<213> ORGANISM: Artificial Sequence
<220> FEATURE:
<223> OTHER INFORMATION: Source: Amino acid sequence of DMS7190 domain
      antibody made using molecular biology techniques.

<400> SEQUENCE: 11

```
His Gly Glu Gly Thr Phe Thr Ser Asp Val Ser Ser Tyr Ser Glu Glu
 1               5                  10                  15

Ala Ala Ala Lys Glu Phe Ile Ala Trp Leu Val Lys Gly Arg Gly Lys
                20                  25                  30

Glu Ala Ala Ala Lys Glu Leu Ala Ala Asp Ile Gln Met Thr Gln Ser
             35                  40                  45

Pro Ser Ser Leu Ser Ala Ser Val Gly Asp Arg Val Thr Ile Thr Cys
         50                  55                  60

Arg Ala Ser Gln Trp Ile Gly Ser Gln Leu Ser Trp Tyr Gln Gln Lys
 65                  70                  75                  80

Pro Gly Lys Ala Pro Lys Leu Leu Ile Met Trp Arg Ser Ser Leu Gln
```

```
                        85                  90                  95
Ser Gly Val Pro Ser Arg Phe Ser Gly Ser Gly Ser Gly Thr Asp Phe
            100                 105                 110

Thr Leu Thr Ile Ser Ser Leu Gln Pro Glu Asp Phe Ala Thr Tyr Tyr
            115                 120                 125

Cys Ala Gln Gly Ala Ala Leu Pro Arg Thr Phe Gly Gln Gly Thr Lys
            130                 135                 140

Val Glu Ile Lys Trp
145

<210> SEQ ID NO 12
<211> LENGTH: 149
<212> TYPE: PRT
<213> ORGANISM: Artificial Sequence
<220> FEATURE:
<223> OTHER INFORMATION: Source: Amino acid sequence of DMS7191 domain
      antibody made using molecular biology techniques.

<400> SEQUENCE: 12

His Gly Glu Gly Thr Phe Thr Ser Asp Gly Ala Asp Leu Leu Glu Gly
 1               5                  10                  15

Gln Ala Ala Lys Glu Phe Ile Ala Trp Leu Val Lys Gly Arg Gly Lys
            20                  25                  30

Glu Ala Ala Ala Lys Glu Leu Ala Ala Asp Ile Gln Met Thr Gln Ser
            35                  40                  45

Pro Ser Ser Leu Ser Ala Ser Val Gly Asp Arg Val Thr Ile Thr Cys
         50                  55                  60

Arg Ala Ser Gln Trp Ile Gly Ser Gln Leu Ser Trp Tyr Gln Gln Lys
65                  70                  75                  80

Pro Gly Lys Ala Pro Lys Leu Leu Ile Met Trp Arg Ser Ser Leu Gln
                85                  90                  95

Ser Gly Val Pro Ser Arg Phe Ser Gly Ser Gly Ser Gly Thr Asp Phe
            100                 105                 110

Thr Leu Thr Ile Ser Ser Leu Gln Pro Glu Asp Phe Ala Thr Tyr Tyr
            115                 120                 125

Cys Ala Gln Gly Ala Ala Leu Pro Arg Thr Phe Gly Gln Gly Thr Lys
            130                 135                 140

Val Glu Ile Lys Arg
145

<210> SEQ ID NO 13
<211> LENGTH: 159
<212> TYPE: PRT
<213> ORGANISM: Artificial Sequence
<220> FEATURE:
<223> OTHER INFORMATION: Source: Amino acid sequence of DMS7192 domain
      antibody made using molecular biology techniques.

<400> SEQUENCE: 13

His Gly Glu Gly Thr Phe Thr Ser Asp Val Ala Thr Ala Cys Glu Gly
 1               5                  10                  15

Gln Ala Ala Lys Glu Phe Ile Ala Cys Leu Val Lys Gly Arg Gly Lys
            20                  25                  30

Glu Ala Ala Ala Lys Glu Ala Ala Ala Lys Glu Ala Ala Ala Lys Glu
            35                  40                  45

Leu Ala Ala Asp Ile Gln Met Thr Gln Ser Pro Ser Ser Leu Ser Ala
         50                  55                  60

Ser Val Gly Asp Arg Val Thr Ile Thr Cys Arg Ala Ser Gln Trp Ile
65                  70                  75                  80
```

Gly Ser Gln Leu Ser Trp Tyr Gln Gln Lys Pro Gly Lys Ala Pro Lys
                85                  90                  95

Leu Leu Ile Met Trp Arg Ser Ser Leu Gln Ser Gly Val Pro Ser Arg
            100                 105                 110

Phe Ser Gly Ser Gly Ser Gly Thr Asp Phe Thr Leu Thr Ile Ser Ser
            115                 120                 125

Leu Gln Pro Glu Asp Phe Ala Thr Tyr Tyr Cys Ala Gln Gly Ala Ala
130                 135                 140

Leu Pro Arg Thr Phe Gly Gln Gly Thr Lys Val Glu Ile Lys Arg
145                 150                 155

<210> SEQ ID NO 14
<211> LENGTH: 154
<212> TYPE: PRT
<213> ORGANISM: Artificial Sequence
<220> FEATURE:
<223> OTHER INFORMATION: Source: Amino acid sequence of DMS7193 domain
      antibody made using molecular biology techniques.

<400> SEQUENCE: 14

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Thr Gly Leu Glu Arg
            20                  25                  30

Glu Ala Ala Ala Lys Glu Ala Ala Ala Lys Glu Leu Ala Ala Asp Ile
        35                  40                  45

Gln Met Thr Gln Ser Pro Ser Ser Leu Ser Ala Ser Val Gly Asp Arg
50                  55                  60

Val Thr Ile Thr Cys Arg Ala Ser Gln Trp Ile Gly Ser Gln Leu Ser
65                  70                  75                  80

Trp Tyr Gln Gln Lys Pro Gly Lys Ala Pro Lys Leu Leu Ile Met Trp
                85                  90                  95

Arg Ser Ser Leu Gln Ser Gly Val Pro Ser Arg Phe Ser Gly Ser Gly
            100                 105                 110

Ser Gly Thr Asp Phe Thr Leu Thr Ile Ser Ser Leu Gln Pro Glu Asp
            115                 120                 125

Phe Ala Thr Tyr Tyr Cys Ala Gln Gly Ala Ala Leu Pro Arg Thr Phe
130                 135                 140

Gly Gln Gly Thr Lys Val Glu Ile Lys Arg
145                 150

<210> SEQ ID NO 15
<211> LENGTH: 147
<212> TYPE: PRT
<213> ORGANISM: Artificial Sequence
<220> FEATURE:
<223> OTHER INFORMATION: Source: Amino acid sequence of DMS7194 domain
      antibody made using molecular biology techniques.

<400> SEQUENCE: 15

His Gly Glu Gly Thr Phe Thr Ser Glu Phe Val Thr Tyr Leu Glu Gly
1               5                   10                  15

Gln Ala Ala Lys Glu Phe Ile Ala Trp Leu Val Lys Gly Lys Glu Ala
            20                  25                  30

Ala Ala Lys Glu Leu Ala Ala Asp Ile Gln Met Thr Gln Ser Pro Ser
        35                  40                  45

Ser Leu Ser Ala Ser Val Gly Asp Arg Val Thr Ile Thr Cys Arg Ala
50                  55                  60

```
Ser Gln Trp Ile Gly Ser Gln Leu Ser Trp Tyr Gln Lys Pro Gly
 65                  70                  75                  80

Lys Ala Pro Lys Leu Leu Ile Met Trp Arg Ser Ser Leu Gln Ser Gly
                 85                  90                  95

Val Pro Ser Arg Phe Ser Gly Ser Gly Ser Gly Thr Asp Phe Thr Leu
            100                 105                 110

Thr Ile Ser Ser Leu Gln Pro Glu Asp Phe Ala Thr Tyr Tyr Cys Ala
        115                 120                 125

Gln Gly Ala Ala Leu Pro Arg Thr Phe Gly Gln Gly Thr Lys Val Glu
130                 135                 140

Ile Lys Trp
145

<210> SEQ ID NO 16
<211> LENGTH: 142
<212> TYPE: PRT
<213> ORGANISM: Artificial Sequence
<220> FEATURE:
<223> OTHER INFORMATION: Source:  Amino acid sequence of DMS7148 domain
      antibody made using molecular biology techniques.

<400> SEQUENCE: 16

His Gly Glu Gly Thr Phe Thr Ser Asp Val Ser Ser Tyr Leu Glu Gly
  1               5                  10                  15

Gln Ala Ala Lys Glu Phe Ile Ala Asp Leu Val Glu Arg Gly Pro
                 20                  25                  30

Ser Ser Asp Ile Gln Met Thr Gln Ser Pro Ser Ser Leu Ser Ala Ser
             35                  40                  45

Val Gly Asp Arg Val Thr Ile Thr Cys Arg Ala Ser Gln Trp Ile Gly
 50                  55                  60

Ser Gln Leu Ser Trp Tyr Gln Gln Lys Pro Gly Lys Ala Pro Lys Leu
 65                  70                  75                  80

Leu Ile Met Trp Arg Ser Ser Leu Gln Ser Gly Val Pro Ser Arg Phe
                 85                  90                  95

Ser Gly Ser Gly Ser Gly Thr Asp Phe Thr Leu Thr Ile Ser Ser Leu
            100                 105                 110

Gln Pro Glu Asp Phe Ala Thr Tyr Tyr Cys Ala Gln Gly Ala Ala Leu
        115                 120                 125

Pro Arg Thr Phe Gly Gln Gly Thr Lys Val Glu Ile Lys Arg
130                 135                 140

<210> SEQ ID NO 17
<211> LENGTH: 142
<212> TYPE: PRT
<213> ORGANISM: Artificial Sequence
<220> FEATURE:
<223> OTHER INFORMATION: Source:  Amino acid sequence of DMS7149 domain
      antibody made using molecular biology techniques.

<400> SEQUENCE: 17

His Gly Glu Gly Thr Phe Thr Ser Glu Phe Val Thr Tyr Leu Glu Gly
  1               5                  10                  15

Gln Ala Ala Lys Glu Phe Ile Ala Trp Leu Val Lys Gly Arg Gly Pro
                 20                  25                  30

Ser Ser Asp Ile Gln Met Thr Gln Ser Pro Ser Ser Leu Ser Ala Ser
             35                  40                  45

Val Gly Asp Arg Val Thr Ile Thr Cys Arg Ala Ser Gln Trp Ile Gly
 50                  55                  60

Ser Gln Leu Ser Trp Tyr Gln Gln Lys Pro Gly Lys Ala Pro Lys Leu
```

```
                65                  70                  75                  80
Leu Ile Met Trp Arg Ser Ser Leu Gln Ser Gly Val Pro Ser Arg Phe
                    85                  90                  95

Ser Gly Ser Gly Ser Gly Thr Asp Phe Thr Leu Thr Ile Ser Ser Leu
                    100                 105                 110

Gln Pro Glu Asp Phe Ala Thr Tyr Tyr Cys Ala Gln Gly Ala Ala Leu
            115                 120                 125

Pro Arg Thr Phe Gly Gln Gly Thr Lys Val Glu Ile Lys Arg
        130                 135                 140

<210> SEQ ID NO 18
<211> LENGTH: 142
<212> TYPE: PRT
<213> ORGANISM: Artificial Sequence
<220> FEATURE:
<223> OTHER INFORMATION: Source: Amino acid sequence of DMS7150 domain
      antibody made using molecular biology techniques.

<400> SEQUENCE: 18

His Gly Glu Gly Thr Phe Thr Ser Asp Val Ser Ser Tyr Leu Glu Gly
  1               5                  10                  15

Met Thr Ser Arg Glu Phe Ile Ala Trp Leu Val Lys Gly Arg Gly Pro
                20                  25                  30

Ser Ser Asp Ile Gln Met Thr Gln Ser Pro Ser Ser Leu Ser Ala Ser
            35                  40                  45

Val Gly Asp Arg Val Thr Ile Thr Cys Arg Ala Ser Gln Trp Ile Gly
        50                  55                  60

Ser Gln Leu Ser Trp Tyr Gln Gln Lys Pro Gly Lys Ala Pro Lys Leu
65                  70                  75                  80

Leu Ile Met Trp Arg Ser Ser Leu Gln Ser Gly Val Pro Ser Arg Phe
                    85                  90                  95

Ser Gly Ser Gly Ser Gly Thr Asp Phe Thr Leu Thr Ile Ser Ser Leu
                    100                 105                 110

Gln Pro Glu Asp Phe Ala Thr Tyr Tyr Cys Ala Gln Gly Ala Ala Leu
            115                 120                 125

Pro Arg Thr Phe Gly Gln Gly Thr Lys Val Glu Ile Lys Arg
        130                 135                 140

<210> SEQ ID NO 19
<211> LENGTH: 142
<212> TYPE: PRT
<213> ORGANISM: Artificial Sequence
<220> FEATURE:
<223> OTHER INFORMATION: Source: Amino acid sequence of DMS7151 domain
      antibody made using molecular biology techniques.

<400> SEQUENCE: 19

His Gly Glu Gly Thr Phe Thr Ser Asp Val Ser Ser Tyr Leu Glu Gly
  1               5                  10                  15

Gln Ala Ala Lys Glu Phe Ile Ala Trp Leu Val Thr Gly Leu Glu Pro
                20                  25                  30

Ser Ser Asp Ile Gln Met Thr Gln Ser Pro Ser Ser Leu Ser Ala Ser
            35                  40                  45

Val Gly Asp Arg Val Thr Ile Thr Cys Arg Ala Ser Gln Trp Ile Gly
        50                  55                  60

Ser Gln Leu Ser Trp Tyr Gln Gln Lys Pro Gly Lys Ala Pro Lys Leu
65                  70                  75                  80

Leu Ile Met Trp Arg Ser Ser Leu Gln Ser Gly Val Pro Ser Arg Phe
                    85                  90                  95
```

```
Ser Gly Ser Gly Ser Gly Thr Asp Phe Thr Leu Thr Ile Ser Ser Leu
            100                 105                 110

Gln Pro Glu Asp Phe Ala Thr Tyr Tyr Cys Ala Gln Gly Ala Ala Leu
        115                 120                 125

Pro Arg Thr Phe Gly Gln Gly Thr Lys Val Glu Ile Lys Arg
    130                 135                 140

<210> SEQ ID NO 20
<211> LENGTH: 142
<212> TYPE: PRT
<213> ORGANISM: Artificial Sequence
<220> FEATURE:
<223> OTHER INFORMATION: Source: Amino acid sequence of DMS7152 domain
      antibody made using molecular biology techniques.

<400> SEQUENCE: 20

His Gly Glu Gly Thr Phe Thr Ser Asp Val Ser Ser Tyr Leu Glu Gly
  1               5                  10                  15

Gln Ala Ala Ser Glu Phe Ile Ala Trp Leu Val Val Asp Gly Gly Pro
             20                  25                  30

Ser Ser Asp Ile Gln Met Thr Gln Ser Pro Ser Ser Leu Ser Ala Ser
         35                  40                  45

Val Gly Asp Arg Val Thr Ile Thr Cys Arg Ala Ser Gln Trp Ile Gly
 50                  55                  60

Ser Gln Leu Ser Trp Tyr Gln Gln Lys Pro Gly Lys Ala Pro Lys Leu
65                  70                  75                  80

Leu Ile Met Trp Arg Ser Ser Leu Gln Ser Gly Val Pro Ser Arg Phe
                 85                  90                  95

Ser Gly Ser Gly Ser Gly Thr Asp Phe Thr Leu Thr Ile Ser Ser Leu
            100                 105                 110

Gln Pro Glu Asp Phe Ala Thr Tyr Tyr Cys Ala Gln Gly Ala Ala Leu
        115                 120                 125

Pro Arg Thr Phe Gly Gln Gly Thr Lys Val Glu Ile Lys Arg
    130                 135                 140

<210> SEQ ID NO 21
<211> LENGTH: 142
<212> TYPE: PRT
<213> ORGANISM: Artificial Sequence
<220> FEATURE:
<223> OTHER INFORMATION: Source: Amino acid sequence of DMS7161 domain
      antibody made using molecular biology techniques.

<400> SEQUENCE: 21

His Gly Glu Gly Thr Phe Thr Ser Asp Val Ser Ser Tyr Leu Glu Gly
  1               5                  10                  15

Gln Ala Ala Lys Glu Phe Ile Ala Asp Leu Val Glu Gly Arg Gly Pro
             20                  25                  30

Ser Ser Asp Ile Gln Met Thr Gln Ser Pro Ser Ser Leu Ser Ala Ser
         35                  40                  45

Val Gly Asp Arg Val Thr Ile Thr Cys Arg Ala Ser Gln Trp Ile Gly
 50                  55                  60

Ser Gln Leu Ser Trp Tyr Gln Gln Lys Pro Gly Lys Ala Pro Lys Leu
65                  70                  75                  80

Leu Ile Met Trp Arg Ser Ser Leu Gln Ser Gly Val Pro Ser Arg Phe
                 85                  90                  95

Ser Gly Ser Gly Ser Gly Thr Asp Phe Thr Leu Thr Ile Ser Ser Leu
            100                 105                 110
```

```
Gln Pro Glu Asp Phe Ala Thr Tyr Tyr Cys Ala Gln Gly Leu Arg His
        115                 120                 125
Pro Lys Thr Phe Gly Gln Gly Thr Lys Val Glu Ile Lys Arg
    130                 135                 140
```

```
<210> SEQ ID NO 22
<211> LENGTH: 108
<212> TYPE: PRT
<213> ORGANISM: Artificial Sequence
<220> FEATURE:
<223> OTHER INFORMATION: Source:  Amino acid sequence of DOM7h1410
      domain antibody made using molecular biology techniques.

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Ser Gln
            20                  25                  30

Leu Ser Trp Tyr Gln Lys Pro Gly Lys Ala Pro Lys Leu Leu Ile
        35                  40                  45

Met Trp Arg Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala Gln Gly Leu Arg His Pro Lys
                85                  90                  95

Thr Phe Gly Gln Gly Thr Lys Val Glu Ile Lys Arg
            100                 105
```

```
<210> SEQ ID NO 23
<211> LENGTH: 324
<212> TYPE: DNA
<213> ORGANISM: Artificial Sequence
<220> FEATURE:
<223> OTHER INFORMATION: Source:  Nucleic acid sequence made using
      molecular biology techniques and encoding the
      Amino acid sequence of the DOM7h1410 domain
      antibody.

<400> SEQUENCE: 23
gacatccaga tgacccagtc tccatcctcc ctgtctgcat ctgtaggaga ccgtgtcacc      60
atcacttgcc gggcaagtca gtggattggg tctcagttat cttggtacca gcagaaacca    120
gggaaagccc ctaagctcct gatcatgtgg cgttcctcgt tgcaaagtgg ggtcccatca    180
cgtttcagtg gcagtggatc tgggacagat ttcactctca ccatcagcag tctgcaacct    240
gaagattttg ctacgtacta ctgtgctcag ggtttgaggc atcctaagac gttcggccaa    300
gggaccaagg tggaaatcaa acgg                                           324
```

```
<210> SEQ ID NO 24
<211> LENGTH: 5
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 24

Gly Gly Gly Gly Ser
1               5
```